US010413539B2

(12) United States Patent
Govindan et al.

(10) Patent No.: US 10,413,539 B2
(45) Date of Patent: *Sep. 17, 2019

(54) THERAPY FOR METASTATIC UROTHELIAL CANCER WITH THE ANTIBODY-DRUG CONJUGATE, SACITUZUMAB GOVITECAN (IMMU-132)

(71) Applicant: Immunomedics, Inc., Morris Plains, NJ (US)

(72) Inventors: Serengulam V. Govindan, Summit, NJ (US); David M. Goldenberg, Mendham, NJ (US)

(73) Assignee: Immunomedics, Inc., Morris Plains, NJ (US)

( * ) Notice: Subject to any disclaimer, the term of this patent is extended or adjusted under 35 U.S.C. 154(b) by 113 days.

This patent is subject to a terminal disclaimer.

(21) Appl. No.: 15/820,708

(22) Filed: Nov. 22, 2017

(65) Prior Publication Data

US 2018/0110772 A1 Apr. 26, 2018

Related U.S. Application Data

(60) Continuation-in-part of application No. 15/069,208, filed on Mar. 14, 2016, now Pat. No. 10,137,196.

(Continued)

(51) Int. Cl.
| | | |
|---|---|---|
| *A61K 31/4745* | (2006.01) | |
| *A61K 31/675* | (2006.01) | |
| *C07K 16/30* | (2006.01) | |
| *A61K 47/68* | (2017.01) | |
| *A61K 31/713* | (2006.01) | |
| *A61K 31/454* | (2006.01) | |
| *C07K 16/28* | (2006.01) | |
| *A61K 31/337* | (2006.01) | |
| *A61K 31/4375* | (2006.01) | |
| *A61K 31/513* | (2006.01) | |
| *C07K 16/32* | (2006.01) | |
| *A61K 31/7088* | (2006.01) | |
| *A61K 31/4184* | (2006.01) | |
| *A61K 39/395* | (2006.01) | |

(Continued)

(52) U.S. Cl.
CPC .......... *A61K 31/4745* (2013.01); *A61K 31/00* (2013.01); *A61K 31/337* (2013.01); *A61K 31/4184* (2013.01); *A61K 31/4375* (2013.01); *A61K 31/454* (2013.01); *A61K 31/502* (2013.01); *A61K 31/513* (2013.01); *A61K 31/519* (2013.01); *A61K 31/52* (2013.01); *A61K 31/675* (2013.01); *A61K 31/7088* (2013.01); *A61K 31/713* (2013.01); *A61K 39/39558* (2013.01); *A61K 47/6803* (2017.08); *A61K 47/6851* (2017.08); *A61K 47/6853* (2017.08); *A61P 35/00* (2018.01); *A61P 35/04* (2018.01); *C07K 16/2803* (2013.01); *C07K 16/2833* (2013.01); *C07K 16/2887* (2013.01); *C07K 16/30* (2013.01); *C07K 16/303* (2013.01); *C07K 16/3007* (2013.01); *C07K 16/3015* (2013.01); *C07K 16/3023* (2013.01); *C07K 16/3061* (2013.01); *C07K 16/3092* (2013.01); *C07K 16/32* (2013.01); *A61B 6/481* (2013.01); *A61K 45/06* (2013.01); *A61K 2039/505* (2013.01); *A61K 2039/507* (2013.01); *A61K 2039/545* (2013.01); *A61K 2039/55* (2013.01); *C07K 2317/24* (2013.01); *C07K 2317/73* (2013.01); *C07K 2317/77* (2013.01); *C07K 2317/92* (2013.01); *C07K 2317/94* (2013.01)

(58) Field of Classification Search
CPC ............ A61K 47/6851; A61K 47/6803; A61K 47/6853; A61K 31/4745
USPC ...................................................... 424/181.1
See application file for complete search history.

(56) References Cited

U.S. PATENT DOCUMENTS

| | | | |
|---|---|---|---|
| 4,036,945 | A | 7/1977 | Haber |
| 4,046,722 | A | 9/1977 | Rowland |

(Continued)

FOREIGN PATENT DOCUMENTS

| | | |
|---|---|---|
| EP | 0253202 | 1/1988 |
| EP | 0306943 | 3/1989 |

(Continued)

OTHER PUBLICATIONS

US 6,558,648 B1, 05/2003, Griffiths et al. (withdrawn)
The FDA Guidance of clinical trial protocol for dosage determination (Feb. 1999, pp. 1-31).*
Samol et al. (Invest New Drugs, 2012, 30: 1493-1500).*
Bardia et al., "IMMU-132, a new antibody-drug conjugate (ADC) against Trop-2, as a novel therapeutic for patients with relapsed/refractory, metastatic, triple-negative breast cancer (TNBC): Results from Phase I/II clinical trial (NCT01631552)", Poster, San Antonio Breast Cancer Symposium, Dec. 9-13, 2014.

(Continued)

*Primary Examiner* — Yan Xiao
(74) *Attorney, Agent, or Firm* — Richard A. Nakashima

(57) ABSTRACT

The present invention relates to therapeutic ADCs comprising SN-38 attached to an anti-Trop-2 antibody or antigen-binding antibody fragment. The ADC may be administered at a dosage of between 4 mg/kg and 18 mg/kg, preferably 4, 6, 8, 9, 10, 12, 16 or 18 mg/kg, most preferably 8 to 10 mg/kg. When administered at specified dosages and schedules, the ADC can reduce solid tumors in size, reduce or eliminate metastases and is effective to treat cancers resistant to standard therapies, such as radiation therapy, chemotherapy or immunotherapy. Preferably, the ADC is administered in combination with one or more other therapeutic agents, such as a PARP inhibitor, a microtubule inhibitor, a Bruton kinase inhibitor or a PI3K inhibitor. Most preferably, the ADC is of use for treating a Trop-2 expressing cancer, such as metastatic urothelial cancer.

21 Claims, 10 Drawing Sheets

Specification includes a Sequence Listing.

Related U.S. Application Data which is a continuation-in-part of application No. 14/667,982, filed on Mar. 25, 2015, now Pat. No. 9,493,573, which is a division of application No. 13/948,732, filed on Jul. 23, 2013, now Pat. No. 9,028,833.

(60) Provisional application No. 61/736,684, filed on Dec. 13, 2012, provisional application No. 61/749,548, filed on Jan. 7, 2013, provisional application No. 62/133,654, filed on Mar. 16, 2015, provisional application No. 62/133,729, filed on Mar. 16, 2015, provisional application No. 62/138,092, filed on Mar. 25, 2015, provisional application No. 62/156,608, filed on May 4, 2015, provisional application No. 62/241,881, filed on Oct. 15, 2015, provisional application No. 62/428,655, filed on Dec. 1, 2016.

(51) Int. Cl.
*A61K 31/00* (2006.01)
*A61P 35/00* (2006.01)
*A61P 35/04* (2006.01)
*A61K 31/502* (2006.01)
*A61K 31/519* (2006.01)
*A61K 31/52* (2006.01)
*A61K 39/00* (2006.01)
*A61B 6/00* (2006.01)
*A61K 45/06* (2006.01)

(56) References Cited

U.S. PATENT DOCUMENTS

| | | |
|---|---|---|
| 4,200,690 A | 4/1980 | Root et al. |
| 4,331,647 A | 5/1982 | Goldenberg |
| 4,359,457 A | 11/1982 | Neville et al. |
| 4,699,784 A | 10/1987 | Shih et al. |
| 4,704,692 A | 11/1987 | Ladner |
| 4,816,567 A | 3/1989 | Cabilly et al. |
| 4,824,659 A | 4/1989 | Howthorne |
| 4,916,213 A | 4/1990 | Scannon et al. |
| 4,918,163 A | 4/1990 | Young et al. |
| 4,925,922 A | 5/1990 | Byers et al. |
| 4,932,412 A | 6/1990 | Goldenberg |
| 4,946,778 A | 8/1990 | Ladner et al. |
| 5,057,313 A | 10/1991 | Shih et al. |
| 5,106,955 A | 4/1992 | Endo et al. |
| 5,112,954 A | 5/1992 | Abrams et al. |
| 5,122,368 A | 6/1992 | Greenfield et al. |
| 5,134,075 A | 7/1992 | Hellstrom et al. |
| 5,171,665 A | 12/1992 | Hellstrom et al. |
| 5,196,337 A | 3/1993 | Ochi et al. |
| 5,204,095 A | 4/1993 | Goodall et al. |
| 5,229,275 A | 7/1993 | Goroff |
| 5,443,953 A | 8/1995 | Hansen et al. |
| 5,484,892 A | 1/1996 | Tedder et al. |
| 5,525,338 A | 6/1996 | Goldenberg |
| 5,565,215 A | 10/1996 | Gref et al. |
| 5,567,610 A | 10/1996 | Borrebaeck et al. |
| 5,593,676 A | 1/1997 | Bhat et al. |
| 5,618,920 A | 4/1997 | Robinson et al. |
| 5,620,708 A | 4/1997 | Amkraut et al. |
| 5,633,425 A | 5/1997 | Lonberg et al. |
| 5,679,640 A | 10/1997 | Gaeta et al. |
| 5,686,072 A | 11/1997 | Uhr et al. |
| 5,693,762 A | 12/1997 | Queen et al. |
| 5,698,178 A | 12/1997 | Goldenberg |
| 5,702,727 A | 12/1997 | Amkraut et al. |
| 5,708,146 A | 1/1998 | Willner et al. |
| 5,716,595 A | 2/1998 | Goldenberg |
| 5,736,119 A | 4/1998 | Goldenberg et al. |
| 5,750,105 A | 5/1998 | Newman et al. |
| 5,776,456 A | 7/1998 | Anderson et al. |
| 5,789,554 A | 8/1998 | Leung et al. |
| 5,792,845 A | 8/1998 | O'Reilly et al. |
| 5,795,967 A | 8/1998 | Aggarwal et al. |
| 5,798,554 A | 8/1998 | Grimaldi et al. |
| 5,817,307 A | 10/1998 | Cummins |
| 5,824,701 A | 10/1998 | Greenwald et al. |
| 5,874,540 A | 2/1999 | Hansen et al. |
| 5,922,302 A | 7/1999 | Goldenberg et al. |
| 6,051,228 A | 4/2000 | Aruffo et al. |
| 6,051,230 A | 4/2000 | Thorpe et al. |
| 6,056,973 A | 5/2000 | Allen et al. |
| 6,077,499 A | 6/2000 | Griffiths et al. |
| 6,096,289 A | 8/2000 | Goldenberg |
| 6,156,754 A | 12/2000 | Lerchen et al. |
| 6,165,440 A | 12/2000 | Esenaliev |
| 6,183,744 B1 | 2/2001 | Goldenberg |
| 6,187,287 B1 | 2/2001 | Leung et al. |
| 6,201,104 B1 | 3/2001 | MacDonald et al. |
| 6,214,345 B1 | 4/2001 | Firestone et al. |
| 6,254,868 B1 | 7/2001 | Leung et al. |
| 6,306,393 B1 | 10/2001 | Goldenberg |
| 6,331,175 B1 | 12/2001 | Goldenberg |
| 6,379,698 B1 | 4/2002 | Leamon |
| 6,387,350 B2 | 5/2002 | Goldenberg |
| 6,395,276 B1 | 5/2002 | Rybak et al. |
| 6,530,944 B2 | 3/2003 | West et al. |
| 6,562,318 B1 | 5/2003 | Filler |
| 6,653,104 B2 | 11/2003 | Goldenberg |
| 6,716,821 B2 | 4/2004 | Zhao et al. |
| 7,018,809 B1 | 5/2006 | Carter |
| 7,074,403 B1 | 7/2006 | Goldenberg et al. |
| 7,122,636 B1 | 10/2006 | Hsei et al. |
| 7,151,164 B2 | 12/2006 | Hansen et al. |
| 7,238,785 B2 | 7/2007 | Govindan et al. |
| 7,312,318 B2 | 12/2007 | Hansen et al. |
| 7,387,779 B2 | 6/2008 | Kalluri |
| 7,585,491 B2 | 9/2009 | Govindan et al. |
| 7,591,994 B2 | 9/2009 | Govindan et al. |
| 7,772,373 B2 | 8/2010 | Hansen et al. |
| 7,820,161 B1 | 10/2010 | Curd et al. |
| 7,910,103 B2 | 3/2011 | Goldenberg |
| 7,931,903 B2 | 4/2011 | Hansen et al. |
| 7,999,083 B2 | 8/2011 | Govindan et al. |
| 8,080,250 B1 | 12/2011 | Govindan et al. |
| 8,119,101 B2 | 2/2012 | Byrd et al. |
| 8,268,317 B2 | 9/2012 | Govindan et al. |
| 8,268,319 B2 | 9/2012 | Govindan et al. |
| 8,420,086 B2 | 4/2013 | Govindan et al. |
| 8,425,912 B2 | 4/2013 | Govindan et al. |
| 8,658,773 B2 | 2/2014 | Zeng et al. |
| 9,028,833 B2 | 5/2015 | Govindan et al. |
| 9,180,205 B2 | 11/2015 | Zeng et al. |
| 9,492,566 B2 | 11/2016 | Goldenberg et al. |
| 2001/0034363 A1 | 10/2001 | Li et al. |
| 2002/0018749 A1 | 2/2002 | Hudson et al. |
| 2003/0103979 A1 | 6/2003 | Leung et al. |
| 2003/0133972 A1 | 7/2003 | Danthi et al. |
| 2004/0001838 A1 | 1/2004 | Zhao et al. |
| 2004/0076683 A1 | 4/2004 | Hoarau et al. |
| 2006/0142506 A1 | 6/2006 | Breitenkamp et al. |
| 2006/0193865 A1 | 8/2006 | Govindan et al. |
| 2007/0142331 A1 | 6/2007 | Zhang et al. |
| 2007/0212350 A1 | 9/2007 | Govindan et al. |
| 2008/0166363 A1 | 7/2008 | Govindan et al. |
| 2010/0104589 A1 | 4/2010 | Govindan et al. |
| 2010/0196266 A1 | 8/2010 | Goldenberg et al. |
| 2011/0070156 A1 | 3/2011 | Govindan et al. |
| 2011/0160159 A1 | 6/2011 | Ryan |
| 2011/0256053 A1 | 10/2011 | Chang et al. |
| 2011/0274704 A1 | 11/2011 | Chang et al. |
| 2011/0305631 A1 | 12/2011 | Govindan et al. |
| 2012/0082617 A1 | 4/2012 | Govindan et al. |
| 2012/0328564 A1 | 12/2012 | Govindan et al. |
| 2013/0090458 A1 | 4/2013 | Govindan et al. |
| 2013/0177526 A1 | 7/2013 | Govindan et al. |
| 2013/0216561 A1 | 8/2013 | Govindan et al. |
| 2014/0004078 A1 | 1/2014 | Govindan et al. |

(56) References Cited

U.S. PATENT DOCUMENTS

| | | | |
|---|---|---|---|
| 2014/0178294 | A1 | 6/2014 | Zeng et al. |
| 2016/0032008 | A1 | 2/2016 | Zeng et al. |
| 2016/0303253 | A1 | 10/2016 | Govindan et al. |

FOREIGN PATENT DOCUMENTS

| | | |
|---|---|---|
| EP | 0332865 | 9/1989 |
| EP | 0510949 | 10/1992 |
| WO | 90/09196 | 8/1990 |
| WO | 91/11465 | 8/1991 |
| WO | 91/13974 | 9/1991 |
| WO | 94/27638 | 12/1994 |
| WO | 9509917 | 4/1995 |
| WO | 96/04925 | 2/1996 |
| WO | 98/04281 | 2/1998 |
| WO | 98/42378 | 10/1998 |
| WO | 98/50435 | 11/1998 |
| WO | 99/02567 | 1/1999 |
| WO | 99/54440 | 10/1999 |
| WO | 00/29584 | 5/2000 |
| WO | 00/67795 | 11/2000 |
| WO | 00/67796 | 11/2000 |
| WO | 0074718 | 12/2000 |
| WO | 0076551 | 12/2000 |
| WO | 0124763 | 4/2001 |
| WO | 2004054622 | 7/2004 |
| WO | 2007123995 | 11/2007 |
| WO | 2012151199 A1 | 11/2012 |

OTHER PUBLICATIONS

Bardia et al., "Therapy of refractory/relapsed metastatic triple-negative breast cancer (TNBC) with an anti-Trop-SN-38 antibody-drug conjugate (ADC), sacituzumab govitecan (IMMU-132): Phase I/II clinical experience", J Clin Oncol 33, 2015 (suppl; abstr 1016), Retrieved from http://meetinglibrary.asco.org/content/150673-156.

Dang et al., "Hypoxia-inducible factor-1 target genes as indicators of tumor vessel response to vascular endothelial growth factor inhibition", Cancer Res. Mar. 15, 2008;68(6):1872-80.

Declaration under 37 C.F.R. 1.132 by David M. Goldenberg, filed in U.S. Appl. No. 13/948,732 on Jun. 20, 2014.

Declaration under 37 C.F.R. 1.132 by David M. Goldenberg, filed in U.S. Appl. No. 14/204,698 on Jan. 7, 2015.

Dotan et al., "A new anti-CEA-SN-38 antibody-drug conjugate (ADC), IMMU-130, is active in controlling metastatic colorectal cancer (mCRC) in patients (pts) refractory or relapsing after irinotecan-containing chemotherapies: Initial results of a phase I/II study", J Clin Oncol 33, 2015 (suppl; abstr 2505), Retrieved from http://meetinglibrary.asco.org/content/148390-156.

Faltas et al., "Sacituzumab Govitecan, a Novel Antibody-Drug Conjugate, in Patients With Metastatic Platinum-Resistant Urothelial Carcinoma", Clin Genitourin Cancer. Feb. 2016;14(1):e75-9.

Goldenberg et al., "Selective in vivo therapeutic efficacies of SN-38 conjugates of an anti-CEACAM5 antibody in preclinical models of human colon carcinoma", Presentation, ASCO 2009 Gastrointestinal Cancers Symposium, San Francisco, CA, Jan. 15-17, 2009.

Goldenberg, D.M., "Challenging the Dogmas: Clinical Efficacy of SN-38-Conjugated Antibodies in Solid Tumors", 26th EORTC-NCI-AACR Symposium on Molecular Targets and Cancer Therapeutics, Barcelona, Spain, Nov. 18-21, 2014.

Goldenberg, D.M., "SN-38 Conjugates for Therapy of Advanced Solid Cancers", 5th Annual World ADC Summit in San Diego, CA, Oct. 26-29, 2014.

Goldenberg et al., "Therapy of human solid tumor xenografts with CD74-targeted milatuzumab-SN-38 immunoconjugates", Poster, 2012 ASCO Annual Meeting, Chicago, IL, Jun. 1-5, 2012.

Goldenberg et al., "Improved Therapeutic Index of IMMU-132 ADC vs. Irinotecan in Preclinical Studies", Presentation, AACR Annual Meeting, San Diego, CA, Apr. 5-9, 2014.

Goldenberg et al., "Tolerability in mice, monkeys, and rabbits of new antibody (MAb)-drug (SN-38) immunoconjugates", Proceedings of the 102nd Annual Meeting of the American Association for Cancer Research; Apr. 2-6, 2011; Orlando, FL. Cancer Res 2011;71(8 Suppl):Abstract # 3619.

Gorman, G., "Focused on Therapy: Cancer, Autoimmune & Other Serious Diseases", Presentation, Oppenheimer 23rd Annual Healthcare Conference, NYC, Dec. 12, 2012.

Govindan et al., "Targeted therapy of human colonic, lung, and pancreatic cancer xenografts, growing in nude mice, with potent antibody conjugates of SN-38", Poster, AACR 100th Annual Meeting, Denver, CO, Apr. 18-22, 2009.

Govindan et al., "Efficacious therapies of two human pancreatic cancer xenografts and an aggressive human lymphoma xenograft with redesigned antibody-SN-38 conjugates", Poster, AACR 101st Annual Meeting, Washington, DC, Apr. 17-21, 2010.

Govindan et al., "Improving the Therapeutic Index in Cancer Therapy by Using Antibody-Drug Conjugates Designed with a Moderately Cytotoxic Drug", Mol Pharm. Nov. 25, 2014. [Epub ahead of print].

Govindan et al., "Optimal cleavable linker for antibody-SN-38 conjugates for cancer therapy: Impact of linker's stability on efficacy", Poster, AACR 103rd Annual Meeting, Chicago, IL, Mar. 31-Apr. 4, 2012.

Govindan et al., "CEACAM5-targeted therapy of human colonic and pancreatic cancer xenografts with potent abetuzumab-SN-38 immunoconjugates", Clin Cancer Res. Oct. 1, 2009;15(19):6052-61.

Govindan et al., "IMMU-130, a unique antibody-drug conjugate (ADC) of SN-38 targeting CEACAM5 antigen: Preclinical basis for clinical activity in metastatic colorectal cancer (mCRC)", J Clin Oncol 33, 2015 (suppl 3; abstr 625), Retrieved from http://meetinglibrary.asco.org/content/139777-158.

Karacay et al., "Combining antibody-targeted radiation (radioimmunotherapy) and antibody-SN-38 conjugates (ADC) improves pancreatic cancer therapy", Poster, AACR 101st Annual Meeting, Washington, DC, Apr. 17-21, 2010.

Moon et al., "Cross-linker evaluation in the design of antibody-SN-38 conjugates for cancer therapy", Poster, AACR 101st Annual Meeting, Washington, DC, Apr. 17-21, 2010.

Reagan-Shaw et al., "Dose translation from animal to human studies revisited", FASEB J. Mar. 2008;22(3):659-61.

Segal et al., "IMMU-130, an SN-38 antibody-drug conjugate (ADC) targeting CEACAM5, is therapeutically active in metastatic colorectal cancer (mCRC): Initial clinical results of two Phase I studies", Presentation, AACR Annual Meeting, San Diego, CA, Apr. 5-9, 2014.

Segal et al., "IMMU-130, an SN-38 antibody-drug conjugate (ADC) targeting CEACAM5, is therapeutically active in metastatic colorectal cancer (mCRC): Initial clinical results of two Phase I studies", 2014 AACR Meeting Apr. 5-9, 2-14, San Diego, CA (Abstract No. CT211).

Seruga et al., "Failures in Phase III: Causes and Consequences", Clin Cancer Res. Oct. 15, 2015;21(20):4552-60.

Starodub et al., "IMMU-132, an SN-38 antibody-drug conjugate (ADC) targeting Trop-2, as a novel platform for the therapy of diverse metastatic solid cancers: Clinical results", Poster, the 2014 Annual Meeting of the American Society of Clinical Oncology (ASCO), May 30-Jun. 3, 2014.

Tahara et al. "The Use of Olaparib (AZD2281) Potentiates SN-38 Cytotoxicity in Colon Cancer Cells by Indirect Inhibition of Rad51-Mediated Repair of DNA Double-Strand Breaks", Mol Cancer Ther; 13(5); 1170-80 (2014).

Bambury et al., "The safety and efficacy of single-agent pemetrexed in platinum-resistant advanced urothelial carcinoma: a large single-institution experience", Oncologist. May 2015;20(5):508-15.

Beer et al., "Southwest Oncology Group phase II study of irinotecan in patients with advanced transitional cell carcinoma of the urothelium that progressed after platinum-based chemotherapy", Clin Genitourin Cancer. Mar. 2008;6(1):36-9.

Bellmunt et al., "Phase III trial of vinflunine plus best supportive care compared with best supportive care alone after a platinum-

(56) References Cited

OTHER PUBLICATIONS containing regimen in patients with advanced transitional cell carcinoma of the urothelial tract", J Clin Oncol. Sep. 20, 2009;27(27):4454-61.
Birchard et al., "Early changes in tumor size in patients treated for advanced stage nonsmall cell lung cancer do not correlate with survival", Cancer. Feb. 1, 2009;115(3):581-6.
Chaudhary et al., "A phase II study of gemcitabine and irinotecan in patients with locally advanced or metastatic bladder cancer", Am J Clin Oncol. Apr. 2014;37(2):188-93.
Clininal Trial NCT01631552 (Jun. 28, 2012, pp. 1-5).
Da Roit et al., "Ibrutinib interferes with the cell-mediated anti-tumor activities of therapeutic CD20 antibodies: implications for combination therapy", Haematologica. Jan. 2015; 100(1): 77-86.
Galsky et al., "Phase II trial of pemetrexed as second-line therapy in patients with metastatic urothelial carcinoma", Invest New Drugs. Jun. 2007;25(3):265-70.
Liu et al., "A randomized phase 2 study of combination cediranib and olaparib versus olaparib alone as recurrence therapy in platinum-sensitive ovarian cancer", Lancet Oncol. Oct. 2014; 15(11): 1207-1214.
Loehrer et al., "A randomized comparison of cisplatin alone or in combination with methotrexate, vinblastine, and doxorubicin in patients with metastatic urothelial carcinoma: a cooperative group study", J Clin Oncol. Jul. 1992;10(7):1066-73.
Logothetis et al., "A prospective randomized trial comparing MVAC and CISCA chemotherapy for patients with metastatic urothelial tumors", J Clin Oncol. Jun. 1990;8(6):1050-5.
Petrylak et al., "Randomized phase II study of docetaxel with or without ramucirumab (IMC-1121B) or icrucumab (IMC-18F1) in patients with urothelial transitional cell carcinoma (TCC) following progression on first-line platinum-based therapy", J Clin Oncol. 2012;30 (abstract TPS4675).
Sonpavde et al., "Improved prognostic classification of patients receiving salvage systemic therapy for advanced urothelial carcinoma", J Clin Oncol. 2015; 33(7):311.
Stepan et al., "Expression of Trop2 cell surface glycoprotein in normal and tumor tissues: potential implications as a cancer therapeutic target", J Histochem Cytochem. Jul. 2011;59(7):701-10.
Sweeney et al., "Phase II study of pemetrexed for second-line treatment of transitional cell cancer of the urothelium", J Clin Oncol. Jul. 20, 2006;24(21):3451-7.
Tagawa et al., "Sacituzumab govitecan (IMMU-132) for patients with pretreated metastatic urothelial uancer (UC): interim results", Annals of Oncology (2017) 28 (suppl_5): v295-v329.
Von Der Maase et al., "Long-term survival results of a randomized trial comparing gemcitabine plus cisplatin, with methotrexate, vinblastine, doxorubicin, plus cisplatin in patients with bladder cancer", J Clin Oncol. Jul. 20, 2005;23(21):4602-8.
Bardia et al., "Safety and efficacy of anti-Trop-2 antibody drug conjugate, sacituzumab govitecan (IMMU-132), in heavily pretreated patients with TNBC", Poster presented at San Antonio Breast Cancer Symposium, Dec. 10, 2015, San Antonio, TX.
Bardia et al., "Safety and tumor responses of the anti-Trop-2 antibody drug conjugate, sacituzumab govitecan (IMMU-132), in refractory, metastatic, triple-negative breast cancer (TNBC): An ongoing Phase II trial", Poster presented at AACR-NCI-EORTC International Conference: Molecular Targets and Cancer Therapeutics, Nov. 8, 2015, Boston, MA.
Basu et al., "The epithelial/carcinoma antigen EGP-1, recognized by monoclonal antibody RS7-3G11, is phosphorylated on serine 303", Int J Cancer. Aug. 9, 1995;62(4):472-9.
Basu et al., "Epithelial glycoprotein EGP-1 recognized by MAb RS7-3G11 is phosphorylated on serine 303", Proc. Amer. Assoc. Cancer Res. 36: 439 (Abstr. #2621), 1995.
Camidge et al., "Therapy of Advanced Metastatic Lung Cancers with an Anti-Trop-2-SN-38 Antibody-Drug Conjugate, IMMU-132: Interim Phase II Clinical Results", Oral presentation at 16th World Conference on Lung Cancer (WCLC), Sep. 7, 2015, Denver, CO.

Cardillo et al., "A novel immunotoxin comprising quadruple RNase tethered to an internalizing anti-TROP-2 humanized MAb shows potent cytotoxicity against diverse solid tumors in vitro", Proc. Amer. Assoc. Cancer Res. Annual Meeting, 51:1296 (Abstr. #5346), 2010.
Cardillo et al., "Combining an anti-Trop-2 antibody-SN-38 conjugate (sacituzumab govitecan) with microtubule inhibitors (paclitaxel and eribulin mesylate) or PARP inhibitor (olaparib) significantly improves therapeutic outcome in experimental triple-negative breast cancer (TNBC)", Mol Cancer Ther 2015;14(12 Suppl 2):Abstract nr C166.
Cardillo et al., "Synthetic lethality in TNBC mediated by an anti-Trop-2 antibody-drug conjugate, sacituzumab govitecan (IMMU-132), when combined with paclitaxel or the PARP inhibitor, olaparib", Poster presented at San Antonio Breast Cancer Symposium, Dec. 10, 2015, San Antonio, TX.
Cardillo et al., "Sacituzumab Govitecan (IMMU-132), an Anti-Trop-2/SN-38 Antibody-Drug Conjugate: Characterization and Efficacy in Pancreatic, Gastric, and Other Cancers", Bioconjug Chem. May 20, 2015;26(5):919-31, Epub May 8, 2015.
Chang et al., "In vitro and in vivo evaluation of a novel recombinant immunotoxin of ranpirnase fused to a humanized anti-EGP-1 antobody, HRS7, for the potential treatment of prostate and lung cancers", Proc. Amer. Assoc. Cancer Res. Annual Meeting, 48: (Abstr. #4795), 2007.
Goldenberg et al., Tolerability in mice, monkeys, and rabbits of new antibody (MAb)-drug (SN-38) immunoconjugates. Proc. Amer. Assoc. Cancer Res. 102nd Annual Meeting, 52: 865 (Abstr. #3619), 2011.
Goldenberg et al., "SN-38 antibody-drug conjugates as a novel platform for solid cancer therapy: preclinical science", American Association for Cancer Research (AACR) 2014 Annual Meeting, Abstr. #2904, Apr. 7, 2014.
Goldenberg et al., "Characterization of an anti-Trop-2-SN-38 antibody-drug conjugate (IMMU-132) with potent activity against solid cancers", American Society of Clinical Oncology (ASCO) 50th Annual Meeting. J Clin Oncol 32:5s, 2014 (suppl; abstr #3107), 2014.
Goldenberg et al., "IMMU-132, a potential new antibody-drug conjugate (ADC) for the treatment of triple-negative breast cancer (TNBC): Preclinical and initial clinical results", Poster P5-19-08 presented at San Antonio Breast Cancer Symposium, Dec. 9-13, 2014.
Goldenberg et al., "Trop-2 is a novel target for solid cancer therapy with sacituzumab govitecan (IMMU-132), an antibody-drug conjugate (ADC)", Oncotarget. Jun. 18, 2015. [Epub ahead of print].
Govindan et al., "Optimal cleavable linker for antibody-SN-38 conjugates for cancer therapy: Impact of linker's stability on efficacy", Proc. Amer. Assoc. Cancer Res. 103rd Annual Meeting, 53: 611 (Abstr. #2526), 2012.
Govindan et al., "Preclinical therapy of breast cancer with a radioiodinated humanized anti-EGP-1 monoclonal antibody: advantage of a residualizing iodine radiolabel", Breast Cancer Res Treat. Mar. 2004;84(2):173-82.
Govindan et al., "Conjugation of SN-38 to an anti-EGP-1 MAB, HRS7, via a cleavable linker shows selective therapeutic activity in a preclinical model of non-small cell lung cancer (NSCLC)", Proc. Eleventh Conf. on Cancer Therapy, Cancer Biotherapy & Radiopharmaceuticals, 21(4):401 (Abstr. #56), 2006.
Govindan et al., "Therapy of human colonic and lung cancer xenografts with SN-38 conjugates of anti-CEACAM5 and anti-EGP-1 humanized monoclonal antibodies", Proc. AACR Molecular Targets and Cancer Therapeutics, 347-348 (Abstr. #C287), 2007.
Govindan et al., "Efficacious therapies of two human pancreatic cancer xenografts and an aggressive human lymphoma xenograft with redesigned antibody-SN-38 conjugates", Proc. Amer. Assoc. Cancer Res. Annual Meeting, 51:591 (Abstr. #2438), 2010.
Guarino et al., "Therapy of advanced metastatic lung cancer with an anti-Trop-2-SN-38 antibody-drug conjugate (ADC), sacituzumab govitecan (IMMU-132): Phase I/II clinical experience", J Clin Oncol 33, 2015 (suppl; abstr 2504), Retrieved from http://meetinglibrary.asco.org/content/148373-156.

(56) References Cited

OTHER PUBLICATIONS

Liu et al., "Novel immunoRNases comprising multiple copies of ranpirnase display potent cytotoxicity in human breast cancer cell lines expressing Trop-2", Proc. Amer. Assoc. Cancer Res. 103rd Annual Meeting, 53: 1124 (Abstr. #4636), 2012.
NCT01270698 (Jan. 3, 2011, pp. 1-4).
NCT01605318 (May 22, 2012, pp. 1-4).
Ocean et al., "Interim results of IMMU-132 (sacituzumab govitecan), an anti-trop-2 antibody-drug conjugate (ADC) in patients with metastatic gastrointestinal (GI) cancers", Poster presented at ESMO's 17th World Congress on Gastrointestinal Cancer, Jul. 4, 2015.
Picozzi et al., "IMMU-132, a new antibody-drug conjugate (ADC), evaluated in patients with advanced, metastatic, pancreatic ductal adenocarcinoma (mPC): Results of a Phase I/II trial", Poster presented at American Association for Cancer Research (AACR) Special Conference on Pancreatic Cancer:Innovations in Research and Treatment, Abstr. #B99, May 18-21, 2014.
Sharkey et al., "Enhanced Delivery of SN-38 to Human Tumor Xenografts with an Anti-Trop-2-SN-38 Antibody Conjugate (Sacituzumab Govitecan)", Clin Cancer Res. Jun. 23, 2015. pii: clincanres.0670.2015. [Epub ahead of print].
Shih et al., "Radioimmunodetection and radioimmunotherapy of xenografted human breast cancer with monoclonal antibody RS7", J. Immunother. 16: 169 (Abstr. #85), 1994.
Starodub et al., "Advanced solid cancer therapy with a novel antibody-drug conjugate (ADC), sacituzumab govitecan (IMMU-132): key preclinical and clinical results", Abstract CT236. Presented at American Association for Cancer Research (AACR) 2015 Annual Meeting, Philadelphia, PA, Apr. 20, 2015.
Starodub et al., "Safety, efficacy, and pharmacokinetics of a new humanized anti-Trop-2 antibody-SN-38 conjugate (IMMU-132) for the treatment of diverse epithelial cancers: Phase I clinical experience", AACR-NCI-EORTC International Conference on Molecular Targets and Cancer Therapeutics Meeting. (Abstr. #C67), Oct. 22, 2013.
Starodub et al., "SN-38 antibody-drug conjugate (ADC) targeting Trop-2, IMMU-132, as a novel platform for the therapy of diverse metastatic solid cancers: Initial clinical results", American Association for Cancer Research (AACR) 2014 Annual Meeting, Abstr. #CT206, Apr. 7, 2014.
Starodub et al., "Therapy of gastrointestinal malignancies with an anti-Trop-2-SN-38 antibody drug conjugate (ADC) (sacituzumab govitecan): Phase I/II clinical experience", 2015 American Society of Clinical Oncology (ASCO) Annual Meeting, J Clin Oncol 33, 2015 (suppl; abstr 3546), Board 38, Jun. 1, 2015.
Starodub et al., "First-in-Human Trial of a Novel Anti-Trop-2 Antibody-SN-38 Conjugate, Sacituzumab Govitecan, for the Treatment of Diverse Metastatic Solid Tumors", Clin Cancer Res. May 5, 2015. [Epub ahead of print].
Starodub et al., "Phase I/II trial of IMMU-132 (isactuzumab govitecan), an anti-Trop-2-SN-38 antibody drug conjugate (ADC): Results in patients with metastatic gastrointestinal (GI) cancers", J Clin Oncol 33, 2015 (suppl 3; abstr 703), Retrieved from http://meetinglibrary.asco.org/content/140198-158.
Stein et al., "Therapy of a breast cancer xenograft using humanized RS7 labeled with residualizing iodine", Proc. Amer. Assoc. Cancer Res. 43: 88 (Abstr. #443), 2002.
Stein et al., "Radioimmunotherapy of lung cancer with MAb RS7-3G11", Proc. Amer. Assoc. Cancer Res. 33: 318 (Abstr. #1897), 1992.
Stein et al., "Radioimmunotherapy with MAb RS7-3G11 in an animal model", Antib. Immunoconj. Radiopharm. 5: 358 (Abstr. #100), 1992.
Stein et al., "Specificity and properties of MAb RS7-3G11 and the antigen defined by this pancarcinoma monoclonal antibody", Int J Cancer. Dec. 2, 1993;55(6):938-46.
Stein et al., "Comparative biodistribution and radioimmunotherapy of monoclonal antibody RS7 and its F(ab')2 in nude mice bearing human tumor xenografts", Cancer. Feb. 1, 1994;73(3 Suppl):816-23.
Stein et al., "Murine monoclonal antibodies raised against human non-small cell carcinoma of the lung: specificity and tumor targeting", Cancer Res. Feb. 15, 1990;50(4):1330-6.
Stein et al., "Effects of radiolabeling monoclonal antibodies with a residualizing iodine radiolabel on the accretion of radioisotope in tumors", Cancer Res. Jul. 15, 1995;55(14):3132-9.
Stein et al., "Successful therapy of a human lung cancer xenograft using MAb RS7 labeled with residualizing radioiodine", Rev Oncol Hematol. Jul.-Aug. 2001;39(1-2):173-80.
Stein et al., "Assessment of combined radioimmunotherapy and chemotherapy for treatment of medullary thyroid cancer", Clin Cancer Res. 5(10 Suppl):3199s-206s, 1999.
Stein et al., Characterization of the epithelial/carcinoma antigen recognized by MAb RS7. Proc. Amer. Assoc. Cancer Res. 35: 501 (Abstr. #2986), 1994.
Stein et al., A novel tumor-associated antigen defined by MAb RS7-3G11: Characterization and internalization properties. Proc. Amer. Assoc. Cancer Res. 33: 341, 1992.
Stein et al., "Characterization of cluster 13: the epithelial/carcinoma antigen recognized by MAb RS7", Int J Cancer Suppl. 1994;8:98-102.
Stein et al., "Targeting and therapy of human non small cell carcinoma of the lung xenografts using 131 I labeled monoclonal antibody RS7 3G11", Proc. Amer. Assoc. Cancer Res. 32: 260, 1991.
Van Rij et al., "Imaging of prostate cancer with immuno-PET and immuno-SPECT using a radiolabeled anti-EGP-1 monoclonal antibody", J Nucl Med. 52(10):1601-7, 2011.
Van Rij et al., "Pretargeting of prostate cancer with an internalizing anti-EGP-1 x anti-HSG bispecific antibody", Annual Congress of the European Association of Nuclear Medicine, Birmingham, UK, Eur J Nucl Med Mol Imaging 38 (Suppl 2):S212 (Abstr. #OP582), 2011.
Vanama et al., Construction, characterization, and mammalian expression of an immunotoxin consisting of ranpimase (Rap) fused to a humanized anti-EGP-1 antibody, hRS7, as a potential therapeutic for prostate cancer. Proc. Amer. Assoc. Cancer Res., 96th Annual Meeting, 160 (Abstr. #679), 2005.
Beckman et al., "Antibody constructs in cancer therapy: protein engineering strategies to improve exposure in solid tumors", Cancer. Jan. 15, 2007;109(2):170-9.
Berenbaum, MC., "Synergy, additivism and antagonism in immunosuppression. A critical review", Clin Exp Immunol. Apr. 1977;28(1):1-18.
Berenbaum, MC., "What is synergy?", Pharmacol Rev. Jun. 1989;41(2):93-141.
Cespedes et al., "Mouse models in oncogenesis and cancer therapy", Clin Transl Oncol. May 2006;8(5):318-29.
Dennis, C., "Cancer: off by a whisker", Nature. Aug. 17, 2006;442(7104):739-41.
Foran, JM., "Antibody-based therapy of non-Hodgkin's lymphoma", Best Pract Res Clin Haematol. Sep. 2002;15(3):449-65.
Fujimori et al., "A modeling analysis of monoclonal antibody percolation through tumors: a binding-site barrier", J Nucl Med. Jul. 1990;31(7):1191-8.
Lundberg et al., "Conjugation of an anti-B-cell lymphoma monoclonal antibody, LL2, to long-circulating drug-carrier lipid emulsions", J. Pharm. Pharmacol. 51(10):1099-105 (1999).
Mack et al., "A small bispecific antibody construct expressed as a functional single-chain molecule with high tumor cell cytotoxicity", Proc. Natl. Acad. Sci. USA 92:7021-7025 (1995).
Maloney et al., "Phase I clinical trial using escalating single-dose infusion of chimeric anti-CD20 monoclonal antibody (IDEC-C2B8) in patients with recurrent B-cell lymphoma", Blood 84(8):2457-66 (1994).
Maloney et al., "IDEC-C2B8 (Rituximab) anti-CD20 monoclonal antibody therapy in patients with relapsed low-grade non-Hodgkin's lymphoma", Blood. Sep. 15, 1997;90(6):2188-95.
Mason et al., "Value of monoclonal anti-CD22 (p135) antibodies for the detection of normal and neoplastic B lymphoid cells", Blood. Mar. 1987;69(3):836-40.

(56) References Cited

OTHER PUBLICATIONS

Mills et al., "Diagnostic imaging of non-Hodgkin's lymphoma with anti-lymphomas antibody labeled with Tc-99m", Proc Am Assoc Cancer Res 1993; 34:479, Abstract #2857.
Mole S. E., "Epitope Mapping", Methods in Molecular Biology, vol. 10: Immunochemical Protocols, Manson (Ed.), Humana Press, Inc. (1992).
Morrison et al., "Chimeric human antibody molecules: mouse antigen-binding domains with human constant region domains", Proc Natl Acad Sci USA Nov. 1984;81(21):6851-5.
Murthy et al., "Lymphoma imaging with a new technetium-99m labelled antibody, LL2", Eur J Nucl Med. 1992;19(6):394-401.
Ochakovskaya et al., Therapy of Disseminated B-Cell Lymphoma Xenografts in Severe Combined Immunodeficient Mice with an Anti-CD74 Antibody Conjugated with (111)Indium, (67)Gallium, or (90)Yttrium, Clin. Cancer Res. 7(6):1505-1510 (2001).
Orlandi et al., "Cloning immunoglobulin variable domains for expression by the polymerase chain reaction", Proc. Natl. Acad. Sci. USA 86:3833-3837 (1989).
Pastan et al., "Immunotoxins", Cell 47:641-648 (1986).
Pawlak-Byczkowska et al., "Two new monoclonal antibodies, EPB-1 and EPB-2, reactive with human lymphoma", Cancer Res. 49(16):4568-77 (1989).
Perrota et al., "Response of chronic relapsing ITP of 10 years duration to Rituximab", Blood, vol. 92(10 Suppl.), p. 88b, 1998, Abstract# 3360.
Press et al., "Radiolabeled-antibody therapy of B-cell lymphoma with autologous bone marrow support", N. Engl. J. Med. 329(17):1219-24 (1993).
Press et al., "Phase II trial of 131I-B1 (anti-CD20) antibody therapy with autologous stem cell transplantation for relapsed B cell lymphomas", Lancet 346:336-40 (1995).
Press et al., "Prospects for the management of non-Hodgkin's lymphomas with monoclonal antibodies and immunoconjugates", Cancer J. Sci. Am. 4(Suppl 2):S19-26 (1998).
Protheroe et al., "Remission of inflammatory arthropathy in association with anti-CD20 therapy for non-Hodgkin's lymphoma", Rheumatology (Oxford) 38(11):1150-2 (1999).
Qu et al., "Carbohydrates engineered at antibody constant domains can be used for site-specific conjugation of drugs and chelates", J. Immunol. Methods 213(2):131-44 (1998).
Qu et al., "Internalization and cytotoxic effects of a humanized anti-CD74 antibody, LL1", Proc Am Assoc Cancer Res 2002;43:255, Abstract # 1269.
Queen et al., "A humanized antibody that binds to the interleukin 2 receptor", Proc Natl Acad Sci U S A. Dec. 1989;86(24):10029-33.
Renner et al., "Monoclonal antibodies in the treatment of non-Hodgkin's lymphoma: recent results and future prospects", Leukemia 11(Suppl 2):S55-9 (1997).
Riechmann et al., "Reshaping human antibodies for therapy", Nature 332(6162):323-7 (1988).
Roche et al., "Cell surface HLA-DR-invariant chain complexes are targeted to endosomes by rapid internalization", Proc Natl Acad Sci U S A. Sep. 15, 1993;90(18):8581-5.
Rowan et al., "Cross-linking of the CAMPATH-1 antigen (CD52) mediates growth inhibition in human B- and T-lymphoma cell lines, and subsequent emergence of CD52-deficient cells", Immunology 95(3):427-36 (1998).
Rudikoff et al., "Single amino acid substitution altering antigen-binding specificity", Proc. Natl. Acad. Sci. USA 79(6):1979-83 (1982).
Rudnick et al., "Affinity and avidity in antibody-based tumor targeting", Cancer Biother Radiopharm. Apr. 2009;24(2):155-61.
Saltzman et al., "Transport rates of proteins in porous materials with known microgeometry", Biophys. J. 55(1):163-71 (1989).
Sandhu, J. S., "Protein engineering of antibodies", Crit. Rev. Biotechnol. 12(5-6):437-62 (1992).
Schwarts-Albiez et al., "The carbohydrate moiety of the CD22 antigen can be modulated by inhibitors of the glycosylation pathway", Leukocyte Typing IV. White Cell Differentiation Antigens, Knapp et al., (Eds.), p. 65-67, Oxford University Press, 1989.
Sherwood et al., "Controlled antibody delivery systems", Biotechnology 10(11):1446-9 (1992).
Shin et al., "Internalization and intracellular processing of an anti-B-cell lymphoma monoclonal antibody, LL2", Int J Cancer 56(4):538-45 (1994).
Singer et al., "Optimal humanization of 1B4, an anti-CD18 murine monoclonal antibody, is achieved by correct choice of human V-region framework sequences", J. Immunol. 150(7):2844-57 (1993).
Stein et al., "Epitope specificity of the anti-(B cell lymphoma) monoclonal antibody, LL2", Cancer Immunol. Immunother. 37(5):293-8 (1993).
Tallarida, RJ., Drug Synergism and Dose Effect Analysis, Ed. Chapman & Hall, 2000, pp. 1-8; 10-13; 57-71.
Taylor et al., "Human immunoglobulin transgenes undergo rearrangement, somatic mutation and class switching in mice that lack endogenous IgM", Int Immunol. Apr. 1994;6(4):579-91.
Theocharis et al., "Characterization of in vivo mutated T cell clones from patients with systemic lupus erythematosus", Clin. Immunol. Immunopathol. 74(2):135-42 (1995).
Tsang et al.,"Reactive oxygen species mediate doxorubicin induced p53-independent apoptosis", Life Sci. Sep. 5, 2003;73(16):2047-58.
Vuist et al., "Potentiation by interleukin 2 of Burkitt's lymphoma therapy with anti-pan B (anti-CD19) monoclonal antibodies in a mouse xenotransplantation model", Cancer Res. 49(14):3783-8 (1989).
Wilson et al., "cDNA cloning of the B cell membrane protein CD22: a mediator of B—B cell interactions", J Exp Med. Jan. 1, 1991;173(1):137-46.
Wilson et al., "Genomic structure and chromosomal mapping of the human CD22 gene", J Immunol. Jun. 1, 1993;150(11):5013-24.
Wosnik et al., "Rapid construction of large synthetic genes: total chemical synthesis of two different versions of the bovine prochymosin gene", Gene. 1987;60(1):115-27.
Wurflein et al., "Evaluating antibodies for their capacity to induce cell-mediated lysis of malignant B cells", Cancer Res. Jul. 15, 1998;58(14):3051-8.
Ausubel et al., (eds.), Current Protocols in Molecular Biology, pp. 8.2.8-8.2.13, John Wiley & Sons, Inc. (1990).
Ausubel et al., (eds.), Short Protocols in Molecular Biology, pp. 8.8-8.10, John Wiley & Sons, Inc. (1995).
Baines et al., "Purification of Immunoglobulin G (IgG)", Methods in Molecular Biology, vol. 10, pp. 79-104, Manson et al., (eds.), The Human Press (1992).
Bambot et al., "Efficient total gene synthesis of 1.35-kb hybrid alpha-lytic protease gene using the polymerase chain reaction", PCR Methods Appl. Feb. 1993;2(3):266-71.
Baum et al., "Initial clinical results with technetium-99m-labeled LL2 monoclonal antibody fragment in the radioimmunodetection of B-cell lymphomas", Cancer Feb. 1, 1994;73(3 Suppl):896-9.
Beers et al., The Merck Manual of Diagnosis and Therapy, Ch. 180, p. 1474-1476; 17th Ed., Whitehouse Station, NJ, Merck Research Labs (1999).
Belisle et al., "Epitope specificity of the anti-B-cell lymphoma monoclonal antibody, LL2", Proc Am Assoc Cancer Res 1993; 34:481, Abstr #2873.
Bendig, M., "Humanization of Rodent Monoclonal Antibodies by CDR Grafting", Academic Press Inc., New York, NY, vol. 8, (1995), pp. 83-93.
Bhat et al., "Human antilipid A monoclonal antibodies bind to human B cells and the i antigen on cord red blood cells", J Immunol. Nov. 1, 1993;151(9):5011-21.
Carter et al., "Humanization of an anti-p185HER2 antibody for human cancer therapy", Proc. Natl. Acad. Sci. USA 89(10):4285-9 (1992).
Coligan et al., (Eds.), Current Protocols in Immunology, vol. 1, pp. 2.5.1-2.6.7; pp. 2.7.1.-2.7.12; pp. 2.8.1-2.8.10; pp. 2.9.1-2.9.3; pp. 2.10.-2.10.4; John Wiley & Sons, Inc., 1991.
Coloma et al., "Design and production of novel tetravalent bispecific antibodies", Nat. Biotechnol. 15(2):159-63(1997).
Dillon et al., "Use of Polymerase Chain Reaction for the Rapid Construction of Synthetic Genes", Methods in Molecular Biology,

(56) References Cited

OTHER PUBLICATIONS vol. 15: PCR Protocols: Current Methods and Applications, White (Ed.), pp. 263-268, Humana Press, Inc. (1993).

Ellis et al., "Engineered anti-CD38 monoclonal antibodies for immunotherapy of multiple myeloma", J Immunol. Jul. 15, 1995;155(2):925-37.

Flavell et al., "Systemic therapy with 3BIT, a triple combination cocktail of anti-CD19, -CD22, and -CD38-saporin immunotoxins, is curative of human B-cell lymphoma in severe combined immunodeficient mice", Cancer Res. 57:4824-9 (1997).

Foy et al., "In vivo CD40-gp39 interactions are essential for thymus-dependent humoral immunity. II. Prolonged suppression of the humoral immune response by an antibody to the ligand for CD40, gp39", J Exp Med. Nov. 1, 1993;178(5):1567-75.

French et al., "Response of B-cell lymphoma to a combination of bispecific antibodies and saporin", Leuk. Res. 20(7):607-17 (1996).

Ghetie et al., "Evaluation of ricin A chain-containing immunotoxins directed against CD19 and CD22 antigens on normal and malignant human B-cells as potential reagents for in vivo therapy", Cancer Res. 48(9):2610-7 (1988).

Goldenberg et al., "Targeting, dosimetry, and radioimmunotherapy of B-cell lymphomas with iodine-131-labeled LL2 monoclonal antibody", J Clin Oncol. Apr. 1991;9(4):548-64.

Goldenberg, D. M., "New Developments in Monoclonal Antibodies for Cancer Detection and Therapy", CA Cancer J. Clin. 44(1):43-64 (1994).

Goldenberg et al., "Epratuzumab (Humanized Anti-CD22 MAb) Conjugated with SN-38, a New Antibody-Drug Conjugate (ADC) for the Treatment of Hematologic Tumors: Preclinical Studies Alone and In Combination with Veltuzumab, a Humanized Anti-CD20 MAb", Blood (ASH Annual Meeting Abstracts) 2010 116: Abstract 3941.

Gondo et al., "HLA class II antigen associated invariant chain gene expression in malignant lymphoma", Br. J. Haematol. 67(4):413-7 (1987).

Green et al., "Antigen-specific human monoclonal antibodies from mice engineered with human Ig heavy and light chain YACs", Nature Genetics 7:13-21 (1994).

Gussow et al., "Humanization of monoclonal antibodies", Methods Enzymol. 1991;203:99-121.

Hansen et al., "Internalization and catabolism of radiolabelled antibodies to the MHC class-II invariant chain by B-cell lymphomas", Biochem. J. 1996, 320:293-300.

Hashida et al., "More useful maleimide compounds for the conjugation of Fab' to horseradish peroxidase through thiol groups in the hinge", J Appl Biochem. Feb.-Apr. 1984;6(1-2):56-63.

Hekman et al., "Initial experience with treatment of human B cell lymphoma with anti-CD19 monoclonal antibody", Cancer Immunol. Immunother. 1991;32(6):364-72.

Hess et al., "Specificity of effector T lymphocytes in autologous graft-versus-host disease: role of the major histocompatibility complex class II invariant chain peptide", Blood 89(6):2203-9 (1997).

Hildebrandt et al., "Expression of CD 21, CD 22, and the mouse erythrocyte receptor on peripheral B lymphocytes in rheumatoid arthritis", Ann Rheum Dis. Jul. 1988;47(7):588-94.

Imuran patient information leaflet, GlaxoSmithKline 7076598/5093, Oct. 2004.

Inaoki et al., "CD19-regulated signaling thresholds control peripheral tolerance and autoantibody production in B lymphocytes", J Exp Med. Dec. 1, 1997;186(11):1923-31.

Jones et al., "Replacing the complementarity-determining regions in a human antibody with those from a mouse" Nature 321(6069):522-5 (1986).

Juweid et al., "99Tcm-LL1: a potential new bone marrow imaging agent", Nucl. Med. Commun. 18(2):142-8 (1997).

Juweid et al., "Treatment of non-Hodgkin's lymphoma with radiolabeled murine, chimeric, or humanized LL2, an anti-CD22 monoclonal antibody", Cancer Res. 55(23 Suppl):5899s-5907s (1995).

Kaminski et al., "Radioimmunotherapy of B-cell lymphoma with [131I]anti-B1 (anti-CD20) antibody", N. Engl. J. Med. 329(7):459-65 (1993).

Kiener et al., "Stimulation of CD40 with purified soluble gp39 induces proinflammatory responses in human monocytes", J Immunol. Nov. 15, 1995;155(10):4917-25.

Kiesel et al., "Removal of cells from a malignant B-cell line from bone marrow with immunomagnetic beads and with complement and immunoglobulin switch variant mediated cytolysis", Leuk. Res. 11(12):1119-25 (1987).

Kohler et al., "Continuous cultures of fused cells secreting antibody of predefined specificity", Nature 256:495-7(1975).

Kreitman et al., "Pseudomonas exotoxin-based immunotoxins containing the antibody LL2 or LL2-Fab' induce regression of subcutaneous human B-cell lymphoma in mice", Cancer Res. 53(4):819-25 (1993).

Leonard et al., "Epratuzumab, a new Anti-CD22, humanized, monoclonal antibody for the therapy of non-Hodgkin's lymphoma (NHL): phase I/II trial results", Blood 94:92a-93a, Abstract # 404, (1999).

Leung et al., "Chimerization and humanization of a B-cell Lymphoma specific antibody, LL2", Proc Am Assoc Cancer Res 1993; 34:481, Abstr #2872.

Leung et al., "Chimerization of LL2, a Rapidly Internalizing Antibody Specific for B Cell Lymphoma", Hybridoma 13(6):469-476 (1994).

Leung et al., "Construction and characterization of a humanized, internalizing, b-cell (CD22)-specific, leukemia/lymphma antibody, LL2", Mol. Immunol. 32(17/18):1413-1427 (1995).

Levine et al., "IgM antibody-related polyneuropathies: B-cell depletion chemotherapy using Rituximab", Neurology 52(8):1701-4 (1999).

Li et al., "The epitope specificity and tissue reactivity of four murine monoclonal anti-CD22 antibodies", Cell Immunol. 118(1):85-99 (1989).

Lonberg et al., "Antigen-specific human antibodies from mice comprising four distinct genetic modifications", Nature 368:856-9 (1994).

Longo, D. L., "Immunotherapy for non-Hodgkin's lymphoma", Curr. Opin. Oncol. 8(5):353-9 (1996).

Losman et al., "Baboon anti-idiotype antibodies mimic a carcinoembryonic antigen epitope", Int J Cancer. Aug. 15, 1990;46(2):310-4.

Lundberg, B., "Preparation of drug-carrier emulsions stabilized with phosphatidylcholine-surfactant mixtures", J. Pharm. Sci. 83(1):72-5 (1994).

Lundberg et al., "Submicron lipid emulsions containing amphipathic polyethylene glycol for use as drug-carriers with prolonged circulation time", Int. J. Pharm. 134:119-127 (1996).

Anbalagan et al., "Peptidomimetic Src/pretubulin inhibitor KX-01 alone and in combination with paclitaxel suppresses growth, metastasis in human ER/PR/HER2-negative tumor xenografts", Mol Cancer Ther. Sep. 2012;11(9):1936-47.

Bennouna et al., "Therapeutic strategies for colorectal cancer in Europe and the United States: focus on chemotherapy for advanced colorectal cancer" Int. J. Clin. Oncol. (2002) 7:236-244.

Burkard et al., "Validating cancer drug targets through chemical genetics", Biochim Biophys Acta. Dec. 2010;1806(2):251-7.

Burke et al., "Design, synthesis, and biological evaluation of antibody-drug conjugates comprised of potent camptothecin analogues", Bioconjug Chem. Jun. 2009;20(6):1242-50.

Burnham et al., "Invasion of HeLa cells by group B *Streptococcus* requires the phosphoinositide-3-kinase signalling pathway and modulates phosphorylation of host-cell Akt and glycogen synthase kinase-3", Microbiology. Dec. 2007;153(Pt 12):4240-52.

Cao et al., "Bispecific Antibodies as Novel Bioconjugates" Bioconj. Chem. Nov.-Dec. 1998;9(6):635-44.

Cardillo et al., "Humanized anti-Trop-2 IgG-SN-38 conjugate for effective treatment of diverse epithelial cancers: preclinical studies in human cancer xenograft models and monkeys", Clin Cancer Res. May 15, 2011;17(10):3157-69.

Carter et al., Chemotherapy of Cancer; 2nd Edition; John Wiley & Sons, New York, 1981; Appendix C.

(56) References Cited

OTHER PUBLICATIONS

Chari et al., "Immunoconjugates Containing Novel Maytansinoids: Promising Anticancer Drugs" Cancer Res. Jan. 1, 1992;52(1):127-31.
Feldmann et al., "Design of effective immunotherapy for human autoimmunity", Nature. Jun. 2, 2005;435(7042):612-9.
Fukuda et al., "Evaluation of novel platinum complexes, inhibitors of topoisomerase I and II in non-small cell lung cancer (NSCLC) sublines resistant to cisplatin", Anticancer Res. Mar.-Apr. 1995;15(2):393-8.
Garcia-Giron et al., "Phase II trial of fortnightly irinotecan (CPT-11) in the treatment of colorectal cancer patients resistant to previous fluoropyrimidine-based chemotherapy", Clin Transl Oncol. Jul. 2005;7(6):244-9.
Gomez-Manzano et al., "Delta-24 increases the expression and activity of topoisomerase I and enhances the antiglioma effect of irinotecan", Clin Cancer Res. Jan. 15, 2006;12(2):556-62.
Govindan et al., "Milatuzumab-SN-38 conjugates for the treatment of CD74+ cancers", Mol Cancer Ther. Jun. 2013;12(6):968-78.
Gueritte-Voegelein et al., "Relationships between the Structure of Taxol Analogues and Their Antimitotic Activity" J. Med. Chem. 1991, 34, 992-998.
Guillemard et al., "Taxane-Antibody Conjugates Afford Potent Cytotoxicity, Enhanced Solubility, and Tumor Target Selectivity" Cancer Res. 61, 694-699, Jan. 15, 2001.
Gura, T., "Systems for identifying new drugs are often faulty", Science. Nov. 7, 1997;278(5340):1041-2.
Hatzakis et al., "Synthesis and single enzyme activity of a clicked lipase-BSA hetero-dimer" Chem. Commun., 2006, 2012-2014.
He et al., "Synthesis and biological evaluation of bis and monocarbonate prodrugs of 10-hydroxycamptothecins", Bioorg Med Chem. Aug. 1, 2004;12(15):4003-8.
Heindel et al., "A Novel Heterobifunctional Linker for Formyl to Thiol Coupling" Bioconjugate Chem. 1991, 2, 427-430.
Horwitz et al., "Antiviral action of camptothecin", Antimicrob Agents Chemother. Nov. 1972;2(5):395-401.
Huang et al., "The Rana catesbeiana rcr Gene Encoding a Cytotoxic Ribonuclease" J. Biol. Chem. 273(11):6395-6401 (1998).
Kaiser, J., "Cancer. First pass at cancer genome reveals complex landscape", Science. Sep. 8, 2006;313(5792):1370.
King et al., "Monoclonal Antibody Conjugates of Doxorubicin Prepared with Branched Linkers: A Novel Method for Increasing the Potency of Doxorubicin Immunoconjugates" Bioconjugate Chem. 1999, 10, 279-288.
Kreitman et al., "Pseudomonas Exotoxin-based Immunotoxins Containing the Antibody LL2 or LL2-Fab' Induce Regression of Subcutaneous Human B-Cell Lymphoma in Mice" Cancer Res. 53, 819-825, Feb. 15, 1993.
Krontiris and Capizzi, Internal Medicine, Chapters 71-72, pp. 699-729; 4th Edition, Jay Stein (Ed.), Elsevier Science, 1994.
Kufe et al., Non-Intercalating Topoisomerase-Targeting Drugs, Holland-Frei Cancer Medicine, Hamilton (ON), BC Decker (2003).
Kufe et al., Topoisomerase Biology, 6th Ed., Holland-Frei Cancer Medicine, Hamilton (ON), BC Decker (2003).
Mahato et al., "Prodrugs for improving tumor targetability and efficiency", Adv Drug Deliv Rev. Jul. 18, 2011;63(8):659-70.
Matsumura, Y., Preclinical and clinical studies of NK012, an SN-38-incorporating polymeric micelles, which is designed based on EPR effect, Adv Drug Deliv Rev. Mar. 18, 2011;63(3):184-92.
Miller et al., "Development of Taxoids with Enhanced Toxicity and Solubility" Poster Presentation, 224th ACS Nat. Meeting, Aug. 18-22, 2002, Boston, MA.
Mine Safety and Health Administration (Special Hazards of Acetylene, Sep. 16, 2011).
Moon et al., "Antibody Conjugates of 7-Ethyl-10-hydroxycamptothecin (SN-38) for Targeted Cancer Chemotherapy" J. Med. Chem. 2008, 51, 6916-6926.
Newton et al., "Potent and specific antitumor effects of an anti-CD22-targeted cytotoxic ribonuclease: potential for the treatment of non-Hodgkin lymphoma" Blood, 97(2):528-35 (2001).
Paul, W., ed., Fundamental Immunology, 3rd Ed., Raven Press, New York, 1993, p. 292-295.
Perez et al., "Inhibition by the anti-mitotic drug doxorubicin of platelet-activating-factor-induced late eosinophil accumulation in rats" Eur. J. Pharmacol. Sep. 4, 1998;356(2-3):239-43.
Reddy et al., "Elimination of Fc Receptor-Dependent Effector Functions of a Modified IgG4 Monoclonal Antibody to Human CD4", J. Immunol. 164:1925-1933 (2000).
Rowlinson-Busza et al., "Targeted delivery of biologic and other antineoplastic agents" Curr. Opin. Oncol. Dec. 1992;4(6):1142-1148.
Sharkey et al., "Epratuzumab-SN-38: a new antibody-drug conjugate for the therapy of hematologic malignancies", Mol Cancer Ther. Jan. 2012;11(1):224-34.
Sharkey et al., "Combination radioimmunotherapy and chemoimmunotherapy involving different or the same targets improves therapy of human pancreatic carcinoma xenograft models", Mol Cancer Ther. Jun. 2011;10(6):1072-81.
Shih et al., "The Processing and Fate of Antibodies and Their Radiolabels Bound to the Surface of Tumor Cells In Vitro: A Comparison of Nine Radiolabels" J. Nucl. Med. 1994; 35:899-908.
Shih et al., "In vitro and in vivo reactivity of an internalizing antibody, RS7, with human breast cancer", Cancer Res. Dec. 1, 1995;55(23 Suppl):5857s-5863s.
Stanford University Environmental Health and Safety (Information on Azide Compounds, Dec. 2, 2008).
Suzawa et al., "Synthesis of a Novel Duocarmycin Derivative DU-257 and its Application to Immunoconjugate Using Poly(ethylene glycol)-dipeptidyl Linker Capable of Tumor Specific Activation" Bioorg. Med. Chem. 8(8):2175-84 (2000).
Suzawa et al., "Enhanced tumor cell selectivity of adriamycin-monoclonal antibody conjugate via a poly(ethylene glycol)-based cleavable linker" J. Control. Release 79:229-242 (2002).
Trail et al., "Carcinoma Reactive Doxorubicin (DOX) Conjugates: Comparison of BR64-DOX Conjugates Prepared With Disulfide or Thioether Linkers", Proc. Amer. Assoc. Cancer Res., vol. 34, Mar. 1993, #2858, p. 479.
Talmadge et al., "Murine models to evaluate novel and conventional therapeutic strategies for cancer", Am J Pathol. Mar. 2007;170(3):793-804.
Thurber et al., "Antibody tumor penetration: transport opposed by systemic and antigen-mediated clearance", Adv Drug Deliv Rev. Sep. 2008;60(12):1421-34.
Van Noort and Amor, "Cell Biology of Autoimmune Disease", vol. 178, pp. 127-206; International Rev. of Cytology, 1998.
Walker et al., "Synthesis of an Immunoconjugate of Camptothecin" Bioorg. Med. Chem. Lett. 12(2):217-219 (2002).

\* cited by examiner

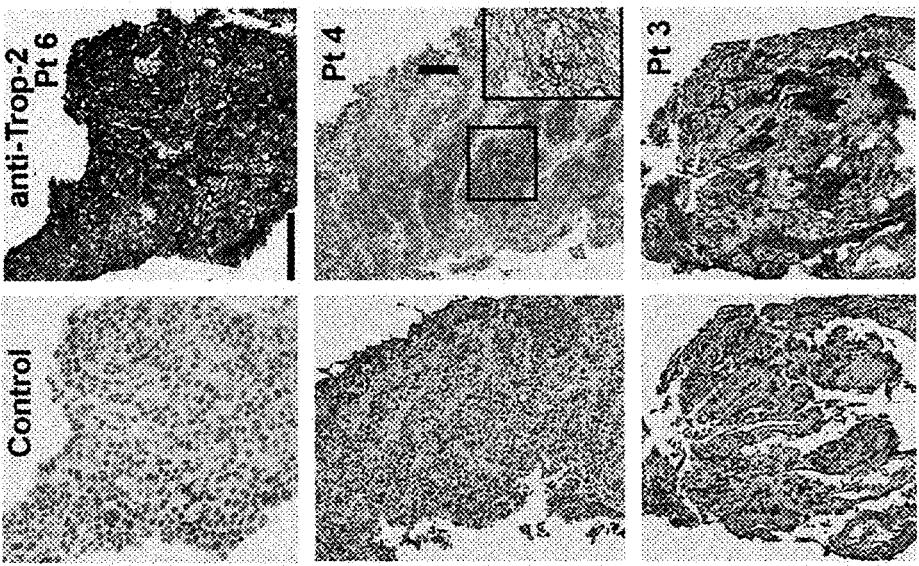
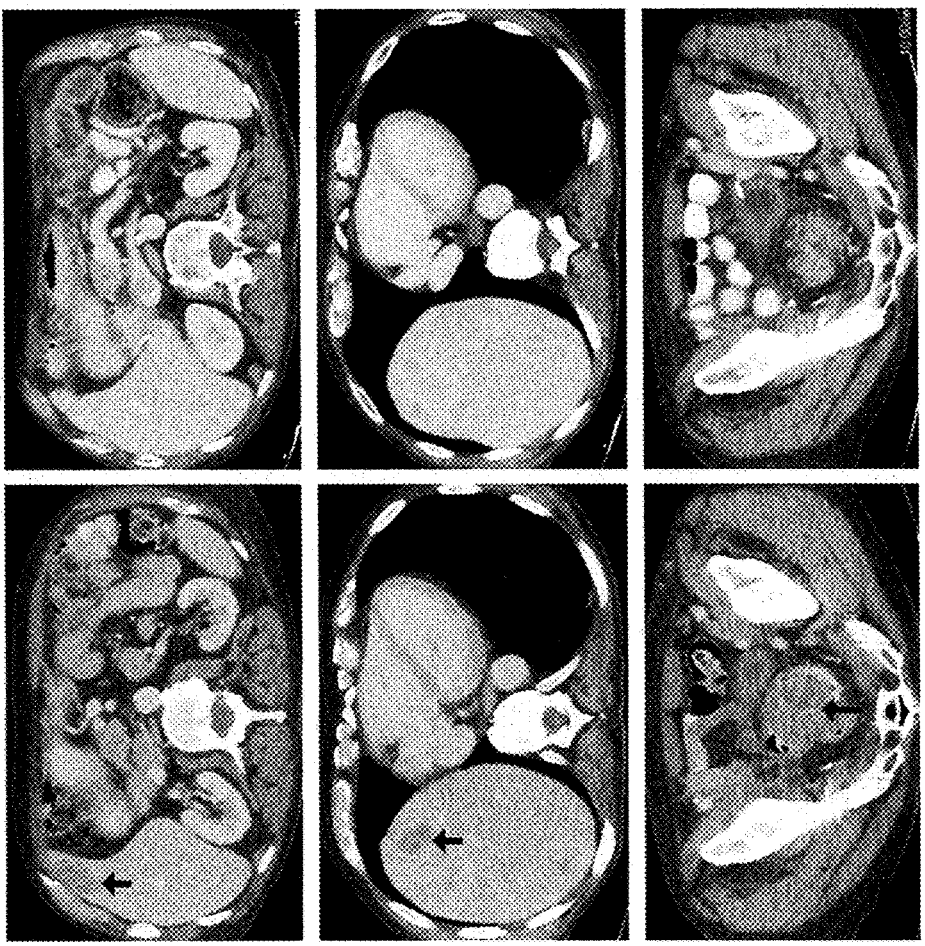

Progression-free Survival
mTNBC Post-Taxane >2 Prior Lines

THERAPY FOR METASTATIC UROTHELIAL CANCER WITH THE ANTIBODY-DRUG CONJUGATE, SACITUZUMAB GOVITECAN (IMMU-132)

RELATED APPLICATIONS

This application is a continuation-in-part of U.S. patent application Ser. No. 15/069,208, filed Mar. 14, 2016, which was a continuation-in-part of U.S. patent application Ser. No. 14/667,982 (now issued U.S. Pat. No. 9,493,573), filed Mar. 25, 2015, which was a divisional of U.S. application Ser. No. 13/948,732 (now U.S. Pat. No. 9,028,833), filed Jul. 23, 2013, which claimed the benefit under 35 U.S.C. 119(e) of U.S. Provisional Patent Applications 61/736,684, filed Dec. 13, 2012, and 61/749,548, filed Jan. 7, 2013. application Ser. No. 15/069,208 claimed the benefit under 35 U.S.C. 119(e) of U.S. Provisional Patent Applications 62/133,654, filed Mar. 16, 2015, 62/133,729, filed Mar. 16, 2015, 62/138,092, filed Mar. 25, 2015, 62/156,608, filed May 4, 2015, and 62/241,881, filed Dec. 15, 2015. The present application claims the benefit under 35 U.S.C. 119(e) of U.S. Provisional Patent Application 62/428,655, filed Dec. 1, 2016. The text of each priority application is incorporated herein by reference in its entirety.

GOVERNMENT SUPPORT

This invention was made with government support under Grant No. CA171388 awarded by the National Institutes of Health. The government has certain rights in the invention.

SEQUENCE LISTING

The instant application contains a Sequence Listing which has been submitted in ASCII format via EFS-Web and is hereby incorporated by reference in its entirety. Said ASCII copy, created on Nov. 13, 2017, is named IMM356US2_SL.txt and is 8,215 bytes in size.

FIELD OF THE INVENTION

The present invention relates to therapeutic use of immunoconjugates of antibodies or antigen-binding antibody fragments and camptothecins, such as SN-38, with improved ability to target various cancer cells in human subjects. In preferred embodiments, the antibodies and therapeutic moieties are linked via an intracellularly-cleavable linkage that increases therapeutic efficacy. In more preferred embodiments, the immunoconjugates are administered at specific dosages and/or specific schedules of administration that optimize the therapeutic effect. The optimized dosages and schedules of administration of SN-38-conjugated antibodies for human therapeutic use disclosed herein show unexpected superior efficacy that could not have been predicted from animal model studies, allowing effective treatment of cancers that are resistant to standard anti-cancer therapies, including irinotecan (CPT-11), the parent compound of SN-38. Most preferably, the methods and compositions are of use to treat Trop-2 positive cancer, particularly urothelial cancer, using an anti-Trop-2 hRS7-SN-38 immunoconjugate. In specific embodiments, the immunoconjugate may be administered to a human subject with a Trop-2 positive cancer at a dosage of between 3 and 18 mg/kg, more preferably between 4 and 12 mg/kg, most preferably between 8 and 10 mg/kg. In other preferred embodiments, the methods and compositions may be used to treat Trop-2 positive cancer that is relapsed from or refractory to other standard anti-cancer therapies, such as chemotherapeutic drugs. Surprisingly, the anti-Trop-2-SN38 antibody drug conjugates (ADCs) are effective to treat Trop-2 positive cancers in patients who had relapsed from or shown resistance to therapy with standard anti-cancer agents, including irinotecan. In other preferred embodiments, an anti-Trop-2-SN-38 ADC, such as IMMU-132, may be administered in combination with one or more other therapeutic agents that may exhibit a synergistic effect with the ADC, such as microtubule inhibitors, PARP inhibitors, Bruton kinase inhibitors or PI3K inhibitors.

BACKGROUND OF THE INVENTION

For many years it has been an aim of scientists in the field of specifically targeted drug therapy to use monoclonal antibodies (MAbs) for the specific delivery of toxic agents to human cancers. Conjugates of tumor-associated MAbs and suitable toxic agents have been developed, but have had mixed success in the therapy of cancer in humans. The toxic agent is most commonly a chemotherapeutic drug, although particle-emitting radionuclides, or bacterial or plant toxins, have also been conjugated to MAbs, especially for the therapy of cancer (Sharkey and Goldenberg, *CA Cancer J Clin.* 2006 July-August; 56(4):226-243).

The advantages of using MAb-chemotherapeutic drug conjugates are that (a) the chemotherapeutic drug itself is structurally well defined; (b) the chemotherapeutic drug is linked to the MAb protein using very well-defined conjugation chemistries, often at specific sites remote from the MAbs' antigen binding regions; (c) MAb-chemotherapeutic drug conjugates can be made more reproducibly and usually with less immunogenicity than chemical conjugates involving MAbs and bacterial or plant toxins, and as such are more amenable to commercial development and regulatory approval; and (d) the MAb-chemotherapeutic drug conjugates are orders of magnitude less toxic systemically than radionuclide MAb conjugates, particularly to the radiation-sensitive bone marrow.

Camptothecin (CPT) and its derivatives are a class of potent antitumor agents. Irinotecan (also referred to as CPT-11) and topotecan are CPT analogs that are approved cancer therapeutics (Iyer and Ratain, *Cancer Chemother. Phamacol.* 42: S31-S43 (1998)). CPTs act by inhibiting topoisomerase I enzyme by stabilizing topoisomerase I-DNA complex (Liu, et al. in *The Camptothecins: Unfolding Their Anticancer Potential,* Liehr J. G., Giovanella, B. C. and Verschraegen (eds), NY Acad Sci., NY 922:1-10 (2000)). CPTs present specific issues in the preparation of conjugates. One issue is the insolubility of most CPT derivatives in aqueous buffers. Second, CPTs provide specific challenges for structural modification for conjugating to macromolecules. For instance, CPT itself contains only a tertiary hydroxyl group in ring-E. The hydroxyl functional group in the case of CPT must be coupled to a linker suitable for subsequent protein conjugation; and in potent CPT derivatives, such as SN-38, the active metabolite of the chemotherapeutic CPT-11, and other C-10-hydroxyl-containing derivatives such as topotecan and 10-hydroxy-CPT, the presence of a phenolic hydroxyl at the C-10 position complicates the necessary C-20-hydroxyl derivatization. Third, the lability under physiological conditions of the δ-lactone moiety of the E-ring of camptothecins results in greatly reduced antitumor potency. Therefore, the conjugation protocol is performed such that it is carried out at a pH of 7 or lower to avoid the lactone ring opening. However, conjugation of a bifunctional CPT possessing an amine-reactive group such as an active ester would typically require a pH of 8 or greater. Fourth, an intracellularly-cleavable moiety preferably is incorporated in the linker/spacer connecting the CPTs and the antibodies or other binding moieties.

A need exists for more effective methods of preparing and administering antibody-CPT conjugates, such as antibody-SN-38 conjugates. Preferably, the methods comprise optimized dosing and administration schedules that maximize efficacy and minimize toxicity of the antibody-CPT conjugates for therapeutic use in human patients.

SUMMARY OF THE INVENTION

As used herein, the abbreviation "CPT" may refer to camptothecin or any of its derivatives, such as SN-38, unless expressly stated otherwise. The present invention resolves an unfulfilled need in the art by providing improved methods and compositions for preparing and administering CPT-antibody immunoconjugates. Preferably, the camptothecin is SN-38. The disclosed methods and compositions are of use for the treatment of a variety of diseases and conditions which are refractory or less responsive to other forms of therapy, and can include diseases against which suitable antibodies or antigen-binding antibody fragments for selective targeting can be developed, or are available or known. Preferred diseases or conditions that may be treated with the subject immunoconjugates include Trop-2 positive cancers, such as metastatic urothelial cancer.

Preferably, the targeting moiety is an antibody, antibody fragment, bispecific or other multivalent antibody, or other antibody-based molecule or compound. The antibody can be of various isotypes, preferably human IgG1, IgG2, IgG3 or IgG4, more preferably comprising human IgG1 hinge and constant region sequences. The antibody or fragment thereof can be a chimeric human-mouse, a chimeric human-primate, a humanized (human framework and murine hypervariable (CDR) regions), or fully human antibody, as well as variations thereof, such as half-IgG4 antibodies (referred to as "unibodies"), as described by van der Neut Kolfschoten et al. (*Science* 2007; 317:1554-1557). More preferably, the antibody or fragment thereof may be designed or selected to comprise human constant region sequences that belong to specific allotypes, which may result in reduced immunogenicity when the immunoconjugate is administered to a human subject. Preferred allotypes for administration include a non-G1m1 allotype (nG1m1), such as G1m3, G1m3,1, G1m3,2 or G1m3,1,2. More preferably, the allotype is selected from the group consisting of the nG1m1, G1m3, nG1m1,2 and Km3 allotypes.

Antibodies of use may bind to any disease-associated antigen known in the art. Where the disease state is cancer, for example, many antigens expressed by or otherwise associated with tumor cells are known in the art, including but not limited to, carbonic anhydrase IX, alpha-fetoprotein (AFP), α-actinin-4, A3, antigen specific for A33 antibody, ART-4, B7, Ba 733, BAGE, BrE3-antigen, CA125, CAMEL, CAP-1, CASP-8/m, CCL19, CCL21, CD1, CD1a, CD2, CD3, CD4, CD5, CD8, CD11A, CD14, CD15, CD16, CD18, CD19, CD20, CD21, CD22, CD23, CD25, CD29, CD30, CD32b, CD33, CD37, CD38, CD40, CD40L, CD44, CD45, CD46, CD52, CD54, CD55, CD59, CD64, CD66a-e, CD67, CD70, CD70L, CD74, CD79a, CD80, CD83, CD95, CD126, CD132, CD133, CD138, CD147, CD154, CDC27, CDK-4/m, CDKN2A, CTLA-4, CXCR4, CXCR7, CXCL12, HIF-1α, colon-specific antigen-p (CSAp), CEA (CEACAM5), CEACAM6, c-Met, DAM, EGFR, EGFRvIII, Trop-2, EGP-2, ELF2-M, Ep-CAM, fibroblast growth factor (FGF), Flt-1, Flt-3, folate receptor, G250 antigen, GAGE, gp100, GRO-β, HLA-DR, HM1.24, human chorionic gonadotropin (HCG) and its subunits, HER2/neu, HMGB-1, hypoxia inducible factor (HIF-1), HSP70-2M, HST-2, Ia, IGF-1R, IFN-γ, IFN-α, IFN-β, IFN-λ, IL-4R, IL-6R, IL-13R, IL-15R, IL-17R, IL-18R, IL-2, IL-6, IL-8, IL-12, IL-15, IL-17, IL-18, IL-23, IL-25, insulin-like growth factor-1 (IGF-1), KC4-antigen, KS-1-antigen, KS1-4, Le-Y, LDR/FUT, macrophage migration inhibitory factor (MIF), MAGE, MAGE-3, MART-1, MART-2, NY-ESO-1, TRAG-3, mCRP, MCP-1, MIP-1A, MIP-1B, MIF, MUC1, MUC2, MUC3, MUC4, MUC5ac, MUC13, MUC16, MUM-1/2, MUM-3, NCA66, NCA95, NCA90, PAM4 antigen, pancreatic cancer mucin, PD-1 receptor, placental growth factor, p53, PLAGL2, prostatic acid phosphatase, PSA, PRAIVIE, PSMA, PlGF, ILGF, ILGF-1R, IL-6, IL-25, RS5, RANTES, T101, SAGE, S100, survivin, survivin-2B, TAC, TAG-72, tenascin, TRAIL receptors, TNF-α, Tn antigen, Thomson-Friedenreich antigens, tumor necrosis antigens, VEGFR, ED-B fibronectin, WT-1, 17-1A-antigen, complement factors C3, C3a, C3b, C5a, C5, an angiogenesis marker, bcl-2, bcl-6, Kras, an oncogene marker and an oncogene product (see, e.g., Sensi et al., *Clin Cancer Res* 2006, 12:5023-32; Parmiani et al., *J Immunol* 2007, 178:1975-79; Novellino et al. *Cancer Immunol Immunother* 2005, 54:187-207). Preferably, the antibody binds to CEACAM5, CEACAM6, Trop-2, AFP, MUC5ac, CD74, CD19, CD20, CD22 or HLA-DR. Most preferably, the antibody binds to Trop-2.

Exemplary anti-cancer antibodies that may be utilized include, but are not limited to, hR1 (anti-IGF-1R, U.S. Pat. No. 9,441,043), hPAM4 (anti-MUC-5ac, U.S. Pat. No. 7,282,567), hA20 (anti-CD20, U.S. Pat. No. 7,151,164), hA19 (anti-CD19, U.S. Pat. No. 7,109,304), hIMMU31 (anti-AFP, U.S. Pat. No. 7,300,655), hLL1 (anti-CD74, U.S. Pat. No. 7,312,318), hLL2 (anti-CD22, U.S. Pat. No. 5,789,554), hMu-9 (anti-CSAp, U.S. Pat. No. 7,387,772), hL243 (anti-HLA-DR, U.S. Pat. No. 7,612,180), hMN-14 (anti-CEACAM5, U.S. Pat. No. 6,676,924), hMN-15 (anti-CEACAM6, U.S. Pat. No. 8,287,865), hRS7 (anti-Trop-2, U.S. Pat. No. 7,238,785), hMN-3 (anti-CEACAM6, U.S. Pat. No. 7,541,440), Ab124 and Ab125 (anti-CXCR4, U.S. Pat. No. 7,138,496), the Examples section of each cited patent or application incorporated herein by reference. More preferably, the antibody is IMMU-31 (anti-AFP), hRS7 (anti-Trop-2), hMN-14 (anti-CEACAM5), hMN-3 (anti-CEACAM6), hMN-15 (anti-CEACAM6), hLL1 (anti-CD74), hLL2 (anti-CD22), hL243 or IMMU-114 (anti-HLA-DR), hA19 (anti-CD19) or hA20 (anti-CD20). In a particularly preferred embodiment, the antibody is hRS7 (anti-Trop-2).

Alternative antibodies of use include, but are not limited to, abciximab (anti-glycoprotein IIb/IIIa), alemtuzumab (anti-CD52), bevacizumab (anti-VEGF), cetuximab (anti-EGFR), gemtuzumab (anti-CD33), ibritumomab (anti-CD20), panitumumab (anti-EGFR), rituximab (anti-CD20), tositumomab (anti-CD20), trastuzumab (anti-ErbB2), lambrolizumab (anti-PD-1 receptor), nivolumab (anti-PD-1 receptor), ipilimumab (anti-CTLA-4), abagovomab (anti-CA-125), adecatumumab (anti-EpCAM), atlizumab (anti-IL-6 receptor), benralizumab (anti-CD125), obinutuzumab (GA101, anti-CD20), CC49 (anti-TAG-72), AB-PGI-XG1-026 (anti-PSMA, U.S. patent application Ser. No. 11/983,372, deposited as ATCC PTA-4405 and PTA-4406), D2/B (anti-PSMA, WO 2009/130575), tocilizumab (anti-IL-6 receptor), basiliximab (anti-CD25), daclizumab (anti- CD25), efalizumab (anti-CD11a), GA101 (anti-CD20; Glycart Roche), muromonab-CD3 (anti-CD3 receptor), natalizumab (anti-α4 integrin), omalizumab (anti-IgE); anti-TNF-α antibodies such as CDP571 (Ofei et al., 2011, *Diabetes* 45:881-85), MTNFAI, M2TNFAI, M3TNFAI, M3TNFABI, M302B, M303 (Thermo Scientific, Rockford, Ill.), infliximab (Centocor, Malvern, Pa.), certolizumab pegol (UCB, Brussels, Belgium), anti-CD40L (UCB, Brussels, Belgium), adalimumab (Abbott, Abbott Park, Ill.), Benlysta (Human Genome Sciences); antibodies for therapy of Alzheimer's disease such as Alz 50 (Ksiezak-Reding et al., 1987, *J Biol Chem* 263:7943-47), gantenerumab, solanezumab and infliximab; anti-fibrin antibodies like 59D8, T2G1s, MH1; anti-CD38 antibodies such as MOR03087 (MorphoSys AG), MOR202 (Celgene), HuMax-CD38 (Genmab) or daratumumab (Johnson & Johnson).

In a preferred embodiment, the chemotherapeutic moiety is selected from camptothecin (CPT) and its analogs and derivatives and is more preferably SN-38. However, other chemotherapeutic moieties that may be utilized include taxanes (e.g., baccatin III, taxol), epothilones, anthracyclines (e.g., doxorubicin (DOX), epirubicin, morpholinodoxorubicin (morpholino-DOX), cyanomorpholino-doxorubicin (cyanomorpholino-DOX), 2-pyrrolinodoxorubicin (2-PDOX) or a prodrug form of 2-PDOX (pro-2-PDOX); see, e.g., Priebe W (ed.), ACS symposium series 574, published by American Chemical Society, Washington D.C., 1995 (332 pp) and Nagy et al., *Proc. Natl. Acad. Sci. USA* 93:2464-2469, 1996), benzoquinoid ansamycins exemplified by geldanamycin (DeBoer et al., *Journal of Antibiotics* 23:442-447, 1970; Neckers et al., *Invest. New Drugs* 17:361-373, 1999), and the like. Preferably, the antibody or fragment thereof links to at least one chemotherapeutic moiety; preferably 1 to about 5 chemotherapeutic moieties; more preferably 6 or more chemotherapeutic moieties, most preferably about 6 to about 12 chemotherapeutic moieties.

An example of a water soluble CPT derivative is CPT-11. Extensive clinical data are available concerning CPT-11's pharmacology and its in vivo conversion to the active SN-38 (Iyer and Ratain, *Cancer Chemother Pharmacol.* 42:S31-43 (1998); Mathijssen et al., *Clin Cancer Res.* 7:2182-2194 (2002); Rivory, *Ann NY Acad Sci.* 922:205-215, 2000)). The active form SN-38 is about 2 to 3 orders of magnitude more potent than CPT-11. In specific preferred embodiments, the immunoconjugate may be an hMN-14-SN-38, hMN-3-SN-38, hMN-15-SN-38, IMMU-31-SN-38, hRS7-SN-38, hA20-SN-38, hL243-SN-38, hLL1-SN-38 or hLL2-SN-38 conjugate.

Various embodiments may concern use of the subject methods and compositions to treat a cancer, including but not limited to non-Hodgkin's lymphomas, B-cell acute and chronic lymphoid leukemias, Burkitt lymphoma, Hodgkin's lymphoma, acute large B-cell lymphoma, hairy cell leukemia, acute myeloid leukemia, chronic myeloid leukemia, acute lymphocytic leukemia, chronic lymphocytic leukemia, T-cell lymphomas and leukemias, multiple myeloma, Waldenstrom's macroglobulinemia, carcinomas, melanomas, sarcomas, gliomas, bone, and skin cancers. The carcinomas may include carcinomas of the oral cavity, esophagus, gastrointestinal tract, pulmonary tract, lung, stomach, colon, breast, ovary, prostate, uterus, endometrium, cervix, urinary bladder, pancreas, bone, brain, connective tissue, liver, gall bladder, urinary bladder, kidney, skin, central nervous system and testes. Preferably, the cancer is urothelial cancer, more preferably metastatic urothelial cancer, most preferably metastatic urothelial cancer that is relapsed from or refractory to standard anti-cancer therapy, such as treatment with chemotherapeutic drugs.

In certain embodiments involving treatment of cancer, the ADCs may be used in combination with surgery, radiation therapy, chemotherapy, immunotherapy with naked antibodies, radioimmunotherapy, immunomodulators, vaccines, and the like. These combination therapies can allow lower doses of each therapeutic to be given in such combinations, thus reducing certain severe side effects, and potentially reducing the courses of therapy required. When there is no or minimal overlapping toxicity, full doses of each can also be given. Surprisingly, combination therapy with antibody-SN38 immunoconjugates and microtubule inhibitors or PARP inhibitors shows unexpected synergistic effects.

Preferred optimal dosing of ADCs may include a dosage of between 3 mg/kg and 18 mg/kg, preferably given either weekly, twice weekly or every other week. The optimal dosing schedule may include treatment cycles of two consecutive weeks of therapy followed by one, two, three or four weeks of rest, or alternating weeks of therapy and rest, or one week of therapy followed by two, three or four weeks of rest, or three weeks of therapy followed by one, two, three or four weeks of rest, or four weeks of therapy followed by one, two, three or four weeks of rest, or five weeks of therapy followed by one, two, three, four or five weeks of rest, or administration once every two weeks, once every three weeks or once a month. Treatment may be extended for any number of cycles, preferably at least 2, at least 4, at least 6, at least 8, at least 10, at least 12, at least 14, or at least 16 cycles. The dosage may be up to 24 mg/kg. Exemplary dosages of use may include 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, and 18 mg/kg. Preferred dosages are 4, 6, 8, 9, 10, 12, 14, 16 or 18 mg/kg. The person of ordinary skill will realize that a variety of factors, such as age, general health, specific organ function or weight, as well as effects of prior therapy on specific organ systems (e.g., bone marrow) may be considered in selecting an optimal dosage of immunoconjugate, and that the dosage and/or frequency of administration may be increased or decreased during the course of therapy. The dosage may be repeated as needed, with evidence of tumor shrinkage observed after as few as 4 to 8 doses. The optimized dosages and schedules of administration disclosed herein show unexpected superior efficacy and reduced toxicity in human subjects, which could not have been predicted from animal model studies. Surprisingly, the superior efficacy allows treatment of tumors that were previously found to be resistant to one or more standard anti-cancer therapies, including the parental compound, CPT-11, from which SN-38 is derived in vivo.

The subject methods may include use of CT and/or PET/CT, or MRI, to measure tumor response at regular intervals. Blood levels of tumor markers, such as CEA (carcinoembryonic antigen), CA19-9, AFP, CA 15.3, or PSA, may also be monitored. Dosages and/or administration schedules may be adjusted as needed, according to the results of imaging and/or marker blood levels.

A surprising result with the instant claimed compositions and methods is the unexpected tolerability of high doses of antibody-drug conjugate, even with repeated infusions, with only relatively low-grade toxicities of nausea and vomiting observed, or manageable neutropenia. A further surprising result is the lack of accumulation of the antibody-drug conjugate, unlike other products that have conjugated SN-38 to albumin, PEG or other carriers. The lack of accumulation is associated with improved tolerability and lack of serious toxicity even after repeated or increased dosing. These surprising results allow optimization of dosage and delivery schedule, with unexpectedly high efficacies and low toxicities. The claimed methods provide for shrinkage of solid tumors, in individuals with previously resistant cancers, of 15% or more, preferably 20% or more, preferably 30% or more, more preferably 40% or more in size (as measured by longest diameter). The person of ordinary skill will realize that tumor size may be measured by a variety of different techniques, such as total tumor volume, maximal tumor size in any dimension or a combination of size measurements in several dimensions. This may be with standard radiological procedures, such as computed tomography, ultrasonography, and/or positron-emission tomography. The means of measuring size is less important than observing a trend of decreasing tumor size with immunoconjugate treatment, preferably resulting in elimination of the tumor.

While the immunoconjugate may be administered as a periodic bolus injection, in alternative embodiments the immunoconjugate may be administered by continuous infusion of antibody-drug conjugates. In order to increase the Cmax and extend the PK of the immunoconjugate in the blood, a continuous infusion may be administered for example by indwelling catheter. Such devices are known in the art, such as HICKMAN®, BROVIAC® or PORT-A-CATH® catheters (see, e.g., Skolnik et al., *Ther Drug Monit* 32:741-48, 2010) and any such known indwelling catheter may be used. A variety of continuous infusion pumps are also known in the art and any such known infusion pump may be used. The dosage range for continuous infusion may be between 0.1 and 3.0 mg/kg per day. More preferably, these immunoconjugates can be administered by intravenous infusions over relatively short periods of 2 to 5 hours, more preferably 2-3 hours.

In particularly preferred embodiments, the immunoconjugates and dosing schedules may be efficacious in patients resistant to standard therapies. For example, an anti-Trop-2 hRS7-SN-38 immunoconjugate may be administered to a patient who has not responded to prior therapy with irinotecan, the parent agent of SN-38. Surprisingly, the irinotecan-resistant patient may show a partial or even a complete response to hRS7-SN-38. The ability of the immunoconjugate to specifically target the tumor tissue may overcome tumor resistance by improved targeting and enhanced delivery of the therapeutic agent. The ADC may also be efficacious to treat cancers resistant to other therapeutic agents, such as platinum-based anti-cancer agents. A specific preferred subject may be a metastatic colon cancer patient, a triple-negative breast cancer patient, a HER+, ER+, progesterone+ breast cancer patient, a metastatic non-small-cell lung cancer (NSCLC) patient, a metastatic pancreatic cancer patient, a metastatic renal cell carcinoma patient, a metastatic gastric cancer patient, a metastatic prostate cancer patient, a metastatic urothelial cancer patient or a metastatic small-cell lung cancer patient.

In certain preferred embodiments, an antibody or immunoconjugate, such as sacituzumab govitecan, may be used in combination therapy with at least one microtubule inhibitor. A number of microtubule inhibitors are known in the art, such as vinca alkaloids (e.g., vincristine, vinblastine), taxanes (e.g., paclitaxel), maytansinoids (e.g., mertansine) and auristatins. Other known microtubule inhibitors include demecolcine, nocodazole, epothilone, docetaxel, discodermolide, colchicine, combrestatin, podophyllotoxin, CI-980, phenylahistins, steganacins, curacins, 2-methoxy estradiol, E7010, methoxy benzenesuflonamides, vinorelbine, vinflunine, vindesine, dolastatins, spongistatin, rhizoxin, tasidotin, halichondrins, hemiasterlins, cryptophycin 52, MMAE and eribulin mesylate (see, e.g., Dumontet & Jordan, 2010, Nat Rev Drug Discov 9:790-803). Any such known microtubule inhibitor may be used in combination with an antibody or antibody-drug conjugate (ADC). Preferably, the microtubule inhibitor is one that exhibits synergistic effects when used in combination with an antibody or ADC. One potent example is SN-38-conjugated antibody, such as sacituzumab govitecan or labetuzumab govitecan (targeting CEACAM5) expressed by many solid cancers. Most preferably, the microtubule inhibitor is paclitaxel or eribulin mesylate.

In other preferred embodiments, the antibody or ADC may be used in combination therapy with at least one PARP inhibitor. A number of PARP inhibitors are known in the art, such as olaparib, talazoparib (BMN-673), rucaparib, veliparib, niraparib, iniparib, CEP 9722, MK 4827, BGB-290, ABT-888, AG014699, BSI-201, CEP-8983 and 3-aminobenzamide (see, e.g., Rouleau et al., 2010, Nat Rev Cancer 10:293-301, Bao et al., 2015, Oncotarget [Epub ahead of print, Sep. 22, 2015]). Any such known PARP inhibitor may be used in combination with an antibody or ADC, such as, for example, an SN-38-antibody conjugate. Preferably, the PARP inhibitor is one that exhibits synergistic effects when used in combination with the antibody or ADC. This has been validated when using an SN-38-conjugated antibody, such as sacituzumab govitecan. Most preferably, the PARP inhibitor is olaparib or rucaparib.

In still other embodiments, an antibody or immunoconjugate may be used in combination with a Bruton kinase inhibitor or PI3K inhibitor. Exemplary Bruton kinase inhibitors include, but are not limited to, ibrutinib (PCI-32765), PCI-45292, CC-292 (AVL-292), ONO-4059, GDC-0834, LFM-A13 or RN486. Exemplary PI3K inhibitors include, but are not limited to, idelalisib, Wortmannin, demethoxyviridin, perifosine, PX-866, IPI-145 (duvelisib), BAY 80-6946, BEZ235, RP6530, TGR1202, SF1126, INK1117, GDC-0941, BKM120, XL147, XL765, Palomid 529, GSK1059615, ZSTK474, PWT33597, IC87114, TG100-115, CAL263, PI-103, GNE477, CUDC-907, AEZS-136 or LY294002. Any Bruton kinase or PI3K inhibitors known in the art may be utilized in the claimed combination therapy.

BRIEF DESCRIPTION OF THE FIGURES

FIG. 2A. Assessment of target lesions on computed tomography (CT) scans using response evaluation criteria in solid tumors, version 1.1, in patient (Pt) 6 before and after sacituzumab govitecan treatment. Patient 6 initially presented with 4 target lesions (2 Liver, 1 Sigmoid Colon, 1 Peritoneum of Pelvis), with a sum of the largest diameters of 138 mm. Additional nontarget lesions were present in the liver and lymph node in the pelvis. Treatment was initiated at a dose level of 8 mg/kg. White arrows highlight target lesions 1-3 in axial slices obtained at baseline. Axial slices of the same region 6 months later after 9 cycles of sacituzumab govitecan treatment demonstrated reduction in sum diameter of target lesions to 86 mm (−38%) and stable disease in nontarget lesions.

FIG. 2B. Expression of Trop-2 (TACSTD2) obtained from three patients with urothelial carcinoma treated with sacituzumab govitecan (patients 3, 4, and 6). Control slides were incubated with normal goat IgG. Corresponding sections incubated with goat anti-Trop-2 antibody demonstrated strong Trop-2 expression. Enlarged inset of Trop-2-expressing cells (patient 6) demonstrated localization of Trop-2 to cell membranes. Scale bars=0.1 mm.

DETAILED DESCRIPTION OF THE INVENTION

DEFINITIONS

Figure 1:
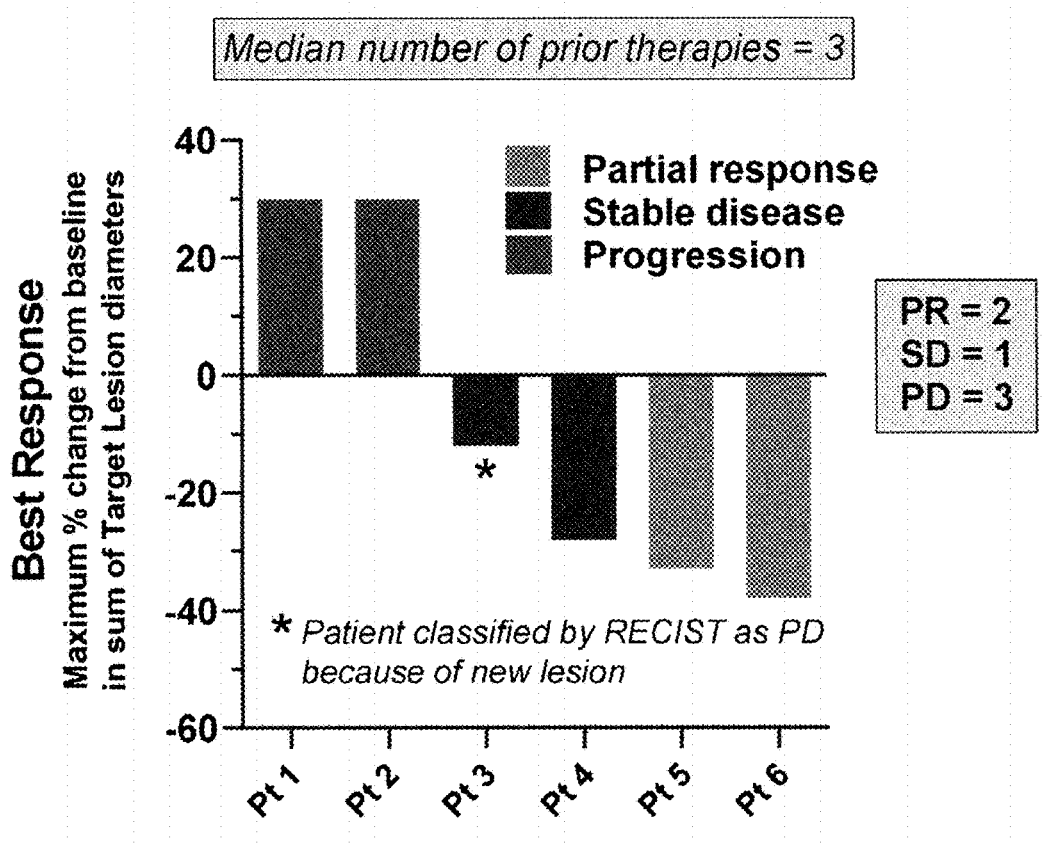
FIG. 1. Waterfall Plot of Best Responses in 6 Patients With Urothelial Carcinoma Treated With Sacituzumab Govitecan. Clinical trial with IMMU-132 was performed as described in Example 1 below. The abbreviations used were: PD=progressive disease; PR=partial response; Pt=patient; RECIST=Response Evaluation Criteria in Solid Tumors; SD=stable disease.

In the description that follows, a number of terms are used and the following definitions are provided to facilitate understanding of the claimed subject matter. Terms that are not expressly defined herein are used in accordance with their plain and ordinary meanings.

Unless otherwise specified, a or an means "one or more."

The term about is used herein to mean plus or minus ten percent (10%) of a value. For example, "about 100" refers to any number between 90 and 110.

An antibody, as used herein, refers to a full-length (i.e., naturally occurring or formed by normal immunoglobulin gene fragment recombinatorial processes) immunoglobulin molecule (e.g., an IgG antibody) or an antigen-binding portion of an immunoglobulin molecule, such as an antibody fragment. An antibody or antibody fragment may be conjugated or otherwise derivatized within the scope of the claimed subject matter. Such antibodies include but are not limited to IgG1, IgG2, IgG3, IgG4 (and IgG4 subforms), as well as IgA isotypes. As used below, the abbreviation "MAb" may be used interchangeably to refer to an antibody, antibody fragment, monoclonal antibody or multispecific antibody.

An antibody fragment is a portion of an antibody such as F(ab')$_2$, F(ab)$_2$, Fab', Fab, Fv, scFv (single chain Fv), single domain antibodies (DABs or VHHs) and the like, including the half-molecules of IgG4 cited above (van der Neut Kolfschoten et al. (Science 2007; 317(14 September):1554-1557). Regardless of structure, an antibody fragment of use binds with the same antigen that is recognized by the intact antibody. The term "antibody fragment" also includes synthetic or genetically engineered proteins that act like an antibody by binding to a specific antigen to form a complex. For example, antibody fragments include isolated fragments consisting of the variable regions, such as the "Fv" fragments consisting of the variable regions of the heavy and light chains and recombinant single chain polypeptide molecules in which light and heavy variable regions are connected by a peptide linker ("scFv proteins"). The fragments may be constructed in different ways to yield multivalent and/or multispecific binding forms.

A naked antibody is generally an entire antibody that is not conjugated to a therapeutic agent. A naked antibody may exhibit therapeutic and/or cytotoxic effects, for example by Fc-dependent functions, such as complement fixation (CDC) and ADCC (antibody-dependent cell cytotoxicity). However, other mechanisms, such as apoptosis, anti-angiogenesis, anti-metastatic activity, anti-adhesion activity, inhibition of heterotypic or homotypic adhesion, and interference in signaling pathways, may also provide a therapeutic effect. Naked antibodies include polyclonal and monoclonal antibodies, naturally occurring or recombinant antibodies, such as chimeric, humanized or human antibodies and fragments thereof. In some cases a "naked antibody" may also refer to a "naked" antibody fragment. As defined herein, "naked" is synonymous with "unconjugated," and means not linked or conjugated to a therapeutic agent.

A chimeric antibody is a recombinant protein that contains the variable domains of both the heavy and light antibody chains, including the complementarity determining regions (CDRs) of an antibody derived from one species, preferably a rodent antibody, more preferably a murine antibody, while the constant domains of the antibody molecule are derived from those of a human antibody. For veterinary applications, the constant domains of the chimeric antibody may be derived from that of other species, such as a primate, cat or dog.

A humanized antibody is a recombinant protein in which the CDRs from an antibody from one species; e.g., a murine antibody, are transferred from the heavy and light variable chains of the murine antibody into human heavy and light variable domains (framework regions). The constant domains of the antibody molecule are derived from those of a human antibody. In some cases, specific residues of the framework region of the humanized antibody, particularly those that are touching or close to the CDR sequences, may be modified, for example replaced with the corresponding residues from the original murine, rodent, subhuman primate, or other antibody.

A human antibody is an antibody obtained, for example, from transgenic mice that have been "engineered" to produce human antibodies in response to antigenic challenge. In this technique, elements of the human heavy and light chain loci are introduced into strains of mice derived from embryonic stem cell lines that contain targeted disruptions of the endogenous heavy chain and light chain loci. The transgenic mice can synthesize human antibodies specific for various antigens, and the mice can be used to produce human antibody-secreting hybridomas. Methods for obtaining human antibodies from transgenic mice are described by Green et al., *Nature Genet.* 7:13 (1994), Lonberg et al., *Nature* 368:856 (1994), and Taylor et al., *Int. Immun.* 6:579 (1994). A fully human antibody also can be constructed by genetic or chromosomal transfection methods, as well as phage display technology, all of which are known in the art. See for example, McCafferty et al., *Nature* 348:552-553 (1990) for the production of human antibodies and fragments thereof in vitro, from immunoglobulin variable domain gene repertoires from unimmunized donors. In this technique, human antibody variable domain genes are cloned in-frame into either a major or minor coat protein gene of a filamentous bacteriophage, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. In this way, the phage mimics some of the properties of the B cell. Phage display can be performed in a variety of formats, for their review, see e.g. Johnson and Chiswell, *Current Opinion in Structural Biology* 3:5564-571 (1993). Human antibodies may also be generated by in vitro activated B cells. See U.S. Pat. Nos. 5,567,610 and 5,229, 275, the Examples section of each of which is incorporated herein by reference.

A therapeutic agent is an atom, molecule, or compound that is useful in the treatment of a disease. Examples of therapeutic agents include, but are not limited to, antibodies, antibody fragments, immunoconjugates, drugs, cytotoxic agents, pro-apopoptotic agents, toxins, nucleases (including DNAses and RNAses), hormones, immunomodulators, chelators, boron compounds, photoactive agents or dyes, radionuclides, oligonucleotides, interference RNA, siRNA, RNAi, anti-angiogenic agents, chemotherapeutic agents, cyokines, chemokines, prodrugs, enzymes, binding proteins or peptides or combinations thereof.

An immunoconjugate is an antibody, antigen-binding antibody fragment, antibody complex or antibody fusion protein that is conjugated to a therapeutic agent. Conjugation may be covalent or non-covalent. Preferably, conjugation is covalent. A particular form of immunoconjugate, in which the antibody component is conjugated to a drug, is referred to herein as an antibody-drug conjugate (ADC).

As used herein, the term antibody fusion protein is a recombinantly-produced antigen-binding molecule in which one or more natural antibodies, single-chain antibodies or antibody fragments are linked to another moiety, such as a protein or peptide, a toxin, a cytokine, a hormone, etc. In certain preferred embodiments, the fusion protein may comprise two or more of the same or different antibodies, antibody fragments or single-chain antibodies fused together, which may bind to the same epitope, different epitopes on the same antigen, or different antigens.

An immunomodulator is a therapeutic agent that when present, alters, suppresses or stimulates the body's immune system. Typically, an immunomodulator of use stimulates immune cells to proliferate or become activated in an immune response cascade, such as macrophages, dendritic cells, B-cells, and/or T-cells. However, in some cases an immunomodulator may suppress proliferation or activation of immune cells. An example of an immunomodulator as described herein is a cytokine, which is a soluble small protein of approximately 5-20 kDa that is released by one cell population (e.g., primed T-lymphocytes) on contact with specific antigens, and which acts as an intercellular mediator between cells. As the skilled artisan will understand, examples of cytokines include lymphokines, monokines, interleukins, and several related signaling molecules, such as tumor necrosis factor (TNF) and interferons. Chemokines are a subset of cytokines. Certain interleukins and interferons are examples of cytokines that stimulate T cell or other immune cell proliferation. Exemplary interferons include interferon-α, interferon-β, interferon-γ and interferon-λ.

CPT is an abbreviation for camptothecin, and as used in the present application CPT represents camptothecin itself or an analog or derivative of camptothecin, such as SN-38.

Anti-Trop-2 Antibodies

Preferably, the subject ADCs include at least one antibody or fragment thereof that binds to Trop-2. In a specific preferred embodiment, the anti-Trop-2 antibody may be a humanized RS7 antibody (see, e.g., U.S. Pat. No. 7,238,785, incorporated herein by reference in its entirety), comprising the light chain CDR sequences CDR1 (KASQDVSIAVA, SEQ ID NO:1); CDR2 (SASYRYT, SEQ ID NO:2); and CDR3 (QQHYITPLT, SEQ ID NO:3) and the heavy chain CDR sequences CDR1 (NYGMN, SEQ ID NO:4); CDR2 (WINTYTGEPTYTDDFKG, SEQ ID NO:5) and CDR3 (GGFGSSYWYFDV, SEQ ID NO:6).

The RS7 antibody was a murine IgG$_1$ raised against a crude membrane preparation of a human primary squamous cell lung carcinoma. (Stein et al., Cancer Res. 50: 1330, 1990) The RS7 antibody recognizes a 46-48 kDa glycoprotein, characterized as cluster 13. (Stein et al., Int. J. Cancer Supp. 8:98-102, 1994) The antigen was designated as EGP-1 (epithelial glycoprotein-1), but is also referred to as Trop-2.

Trop-2 is a type-I transmembrane protein and has been cloned from both human (Fornaro et al., Int J Cancer 1995; 62:610-8) and mouse cells (Sewedy et al., Int J Cancer 1998; 75:324-30). In addition to its role as a tumor-associated calcium signal transducer (Ripani et al., Int J Cancer 1998; 76:671-6), the expression of human Trop-2 was shown to be necessary for tumorigenesis and invasiveness of colon cancer cells, which could be effectively reduced with a polyclonal antibody against the extracellular domain of Trop-2 (Wang et al., Mol Cancer Ther 2008; 7:280-5).

The growing interest in Trop-2 as a therapeutic target for solid cancers (Cubas et al., Biochim Biophys Acta 2009; 1796:309-14) is attested by further reports that documented the clinical significance of overexpressed Trop-2 in breast (Huang et al., Clin Cancer Res 2005; 11:4357-64), colorectal (Ohmachi et al., Clin Cancer Res 2006; 12:3057-63; Fang et al., Int J Colorectal Dis 2009; 24:875-84), and oral squamous cell carcinomas (Fong et al., Modern Pathol 2008; 21:186-91). The latest evidence that prostate basal cells expressing high levels of Trop-2 are enriched for in vitro and in vivo stem-like activity is particularly noteworthy (Goldstein et al., Proc Natl Acad Sci USA 2008; 105:20882-7).

Flow cytometry and immunohistochemical staining studies have shown that the RS7 MAb detects antigen on a variety of tumor types, with limited binding to normal human tissue (Stein et al., 1990). Trop-2 is expressed primarily by carcinomas such as carcinomas of the lung, stomach, urinary bladder, breast, ovary, uterus, and prostate. Localization and therapy studies using radiolabeled murine RS7 MAb in animal models have demonstrated tumor targeting and therapeutic efficacy (Stein et al., 1990; Stein et al., 1991). Strong RS7 staining has been demonstrated in tumors from the lung, breast, bladder, ovary, uterus, stomach, and prostate (Stein et al., Int. J. Cancer 55:938, 1993). The lung cancer cases comprised both squamous cell carcinomas and adenocarcinomas (Stein et al., Int. J. Cancer 55:938, 1993). Both cell types stained strongly, indicating that the RS7 antibody does not distinguish between histologic classes of non-small-cell carcinoma of the lung.

The RS7 MAb is rapidly internalized into target cells (Stein et al., 1993). The internalization rate constant for RS7 MAb is intermediate between the internalization rate constants of two other rapidly internalizing MAbs, which have been demonstrated to be useful for immunoconjugate production. (Id.) It is well documented that internalization of immunoconjugates is a requirement for anti-tumor activity. (Pastan et al., Cell 47:641, 1986) Internalization of drug immunoconjugates has been described as a major factor in anti-tumor efficacy (Yang et al., Proc. Nat'l Acad. Sci. USA 85: 1189, 1988).Thus, the RS7 antibody exhibits several important properties for therapeutic applications.

While the hRS7 antibody is preferred, other anti-Trop-2 antibodies are known and/or publicly available and in alternative embodiments may be utilized in the subject ADCs. While humanized or human antibodies are preferred for reduced immunogenicity, in alternative embodiments a chimeric antibody may be of use. As discussed below, methods of antibody humanization are well known in the art and may be utilized to convert an available murine or chimeric antibody into a humanized form.

Anti-Trop-2 antibodies are commercially available from a number of sources and include LS-C126418, LS-C178765, LS-C126416, LS-C126417 (LifeSpan BioSciences, Inc., Seattle, Wash.); 10428-MM01, 10428-MM02, 10428-R001, 10428-R030 (Sino Biological Inc., Beijing, China); MR54 (eBioscience, San Diego, Calif.); sc-376181, sc-376746, Santa Cruz Biotechnology (Santa Cruz, Calif.); MM0588-49D6, (Novus Biologicals, Littleton, Colo.); ab79976, and ab89928 (ABCAM®, Cambridge, Mass.).

Other anti-Trop-2 antibodies have been disclosed in the patent literature. For example, U.S. Publ. No. 2013/0089872 discloses anti-Trop-2 antibodies K5-70 (Accession No. FERM BP-11251), K5-107 (Accession No. FERM BP-11252), K5-116-2-1 (Accession No. FERM BP-11253), T6-16 (Accession No. FERM BP-11346), and T5-86 (Accession No. FERM BP-11254), deposited with the International Patent Organism Depositary, Tsukuba, Japan. U.S. Pat. No. 5,840,854 disclosed the anti-Trop-2 monoclonal antibody BR110 (ATCC No. HB11698). U.S. Pat. No. 7,420,040 disclosed an anti-Trop-2 antibody produced by hybridoma cell line AR47A6.4.2, deposited with the IDAC (International Depository Authority of Canada, Winnipeg, Canada) as accession number 141205-05. U.S. Pat. No. 7,420,041 disclosed an anti-Trop-2 antibody produced by hybridoma cell line AR52A301.5, deposited with the IDAC as accession number 141205-03. U.S. Publ. No. 2013/0122020 disclosed anti-Trop-2 antibodies 3E9, 6G11, 7E6, 15E2, 18B1. Hybridomas encoding a representative antibody were deposited with the American Type Culture Collection (ATCC), Accession Nos. PTA-12871 and PTA-12872. Immunoconjugate PF 06263507, comprising an anti-5T4 (anti-Trop-2) antibody attached to the tubulin inhibitor monomethylauristatin F (MMAF) is available from Pfizer, Inc. (Groton, CT) (see, e.g., Sapra et al., 2013, Mol Cancer Ther 12:38-47). U.S. Pat. No. 8,715,662 discloses anti-Trop-2 antibodies produced by hybridomas deposited at the AID-ICLC (Genoa, Italy) with deposit numbers PD 08019, PD 08020 and PD 08021. U.S. Patent Application Publ. No. 20120237518 discloses anti-Trop-2 antibodies 77220, KM4097 and KM4590. U.S. Pat. No. 8,309,094 (Wyeth) discloses antibodies A1 and A3, identified by sequence listing. The Examples section of each patent or patent application cited above in this paragraph is incorporated herein by reference. Non-patent publication Lipinski et al. (1981, Proc Natl. Acad Sci USA, 78:5147-50) disclosed anti-Trop-2 antibodies 162-25.3 and 162-46.2.

Numerous anti-Trop-2 antibodies are known in the art and/or publicly available. As discussed below, methods for preparing antibodies against known antigens were routine in the art. The sequence of the human Trop-2 protein was also known in the art (see, e.g., GenBank Accession No. CAA54801.1). Methods for producing humanized, human or chimeric antibodies were also known. The person of ordinary skill, reading the instant disclosure in light of general knowledge in the art, would have been able to make and use the genus of anti-Trop-2 antibodies in the subject ADCs.

Camptothecin Conjugates

Non-limiting methods and compositions for preparing immunoconjugates comprising a camptothecin therapeutic agent attached to an antibody or antigen-binding antibody fragment are described below. In preferred embodiments, the solubility of the drug is enhanced by placing a defined polyethyleneglycol (PEG) moiety (i.e., a PEG containing a defined number of monomeric units) between the drug and the antibody, wherein the defined PEG is a low molecular weight PEG, preferably containing 1-30 monomeric units, more preferably containing 1-12 monomeric units, most preferably containing 6-8 monomeric units.

Preferably, a first linker connects the drug at one end and may terminate with an acetylene or an azide group at the other end. This first linker may comprise a defined PEG moiety with an azide or acetylene group at one end and a different reactive group, such as carboxylic acid or hydroxyl group, at the other end. Said bifunctional defined PEG may be attached to the amine group of an amino alcohol, and the hydroxyl group of the latter may be attached to the hydroxyl group on the drug in the form of a carbonate. Alternatively, the non-azide (or acetylene) moiety of said defined bifunctional PEG is optionally attached to the N-terminus of an L-amino acid or a polypeptide, with the C-terminus attached to the amino group of amino alcohol, and the hydroxy group of the latter is attached to the hydroxyl group of the drug in the form of carbonate or carbamate, respectively.

A second linker, comprising an antibody-coupling group and a reactive group complementary to the azide (or acetylene) group of the first linker, namely acetylene (or azide), may react with the drug-(first linker) conjugate via acetylene-azide cycloaddition reaction to furnish a final bifunctional drug product that is useful for conjugating to disease-targeting antibodies. The antibody-coupling group is preferably either a thiol or a thiol-reactive group.

Methods for selective regeneration of the 10-hydroxyl group in the presence of the C-20 carbonate in preparations of drug-linker precursor involving CPT analogs such as SN-38 are provided below. Other protecting groups for reactive hydroxyl groups in drugs such as the phenolic hydroxyl in SN-38, for example t-butyldimethylsilyl or t-butyldiphenylsilyl, may also be used, and these are deprotected by tetrabutylammonium fluoride prior to linking of the derivatized drug to an antibody-coupling moiety. The 10-hydroxyl group of CPT analogs is alternatively protected as an ester or carbonate, other than 'BOC', such that the bifunctional CPT is conjugated to an antibody without prior deprotection of this protecting group. The protecting group is readily deprotected under physiological pH conditions after the bioconjugate is administered.

In the acetylene-azide coupling, referred to as 'click chemistry', the azide part may be on L2 with the acetylene part on L3. Alternatively, L2 may contain acetylene, with L3 containing azide. 'Click chemistry' refers to a copper (+1)-catalyzed cycloaddition reaction between an acetylene moiety and an azide moiety (Kolb H C and Sharpless K B, *Drug Discov Today* 2003; 8: 1128-37), although alternative forms of click chemistry are known and may be used. Click chemistry takes place in aqueous solution at near-neutral pH conditions, and is thus amenable for drug conjugation. The advantage of click chemistry is that it is chemoselective, and complements other well-known conjugation chemistries such as the thiol-maleimide reaction.

An exemplary preferred embodiment is directed to a conjugate of a drug derivative and an antibody of the general formula (1) shown below.

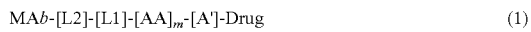

MAb-[L2]-[L1]-[AA]$_m$-[A']-Drug     (1)

where MAb is a disease-targeting antibody; L2 is a component of the cross-linker comprising an antibody-coupling moiety and one or more of acetylene (or azide) groups; L1 comprises a defined PEG with azide (or acetylene) at one end, complementary to the acetylene (or azide) moiety in L2, and a reactive group such as carboxylic acid or hydroxyl group at the other end; AA is an L-amino acid; m is an integer with values of 0, 1, 2, 3, or 4; and A' is an additional spacer, selected from the group of ethanolamine, 4-hydroxybenzyl alcohol, 4-aminobenzyl alcohol, or substituted or unsubstituted ethylenediamine. The L amino acids of 'AA' are selected from alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine. If the A' group contains hydroxyl, it is linked to the hydroxyl group or amino group of the drug in the form of a carbonate or carbamate, respectively.

In a preferred embodiment of formula 1, A' is a substituted ethanolamine derived from an L-amino acid, wherein the carboxylic acid group of the amino acid is replaced by a hydroxymethyl moiety. A' may be derived from any one of the following L-amino acids: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine.

In an example of the conjugate of the preferred embodiment of formula 1, m is 0, A' is L-valinol, and the drug is exemplified by SN-38. In another example of formula 1, m is 1 and represented by a derivatized L-lysine, A' is L-valinol, and the drug is exemplified by SN-38. In this embodiment, an amide bond is first formed between the carboxylic acid of an amino acid such as lysine and the amino group of valinol, using orthogonal protecting groups for the lysine amino groups. The protecting group on the N-terminus of lysine is removed, keeping the protecting group on the side chain of lysine intact, and the N-terminus is coupled to the carboxyl group on the defined PEG with azide (or acetylene) at the other end. The hydroxyl group of valinol is then attached to the 20-chloroformate derivative of 10-hydroxy-protected SN-38, and this intermediate is coupled to an L2 component carrying the antibody-binding moiety as well as the complementary acetylene (or azide) group involved in the click cycloaddition chemistry. Finally, removal of protecting groups at both lysine side chain and SN-38 gives the product of this example.

While not wishing to be bound by theory, the small MW SN-38 product, namely valinol-SN-38 carbonate, generated after intracellular proteolysis, has the additional pathway of liberation of intact SN-38 through intramolecular cyclization involving the amino group of valinol and the carbonyl of the carbonate.

In another preferred embodiment, A' of the general formula 1 is A-OH, whereby A-OH is a collapsible moiety such as 4-aminobenzyl alcohol or a substituted 4-aminobenzyl alcohol substituted with a $C_1$-$C_{10}$ alkyl group at the benzylic position, and the latter, via its amino group, is attached to an L-amino acid or a polypeptide comprising up to four L-amino acid moieties; wherein the N-terminus is attached to a cross-linker terminating in the antibody-binding group.

In another example of a preferred embodiment, the A-OH of A' of general formula 1 is derived from a substituted 4-aminobenzyl alcohol, and 'AA' is comprised of a single L-amino acid with m=1 in the general formula 1, and the drug is exemplified with SN-38. Single amino acid of AA may be selected from any one of the following L-amino acids: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine. The substituent R on 4-aminobenzyl alcohol moiety (A-OH embodiment of A') is hydrogen or an alkyl group selected from C1-C10 alkyl groups. An example of this formula, wherein the single amino acid AA is L-lysine and R=H, and the drug is exemplified by SN-38 is referred to as MAb-CL2A-SN-38 (shown below). The structure differs from the linker MAb-CL2-SN-38 in the substitution of a single lysine residue for a Phe-Lys dipeptide found in the CL2 linker. The Phe-Lys dipeptide was designed as a cathepsin B cleavage site for lysosomal enzyme, which was considered to be important for intracellular release of bound drug. Surprisingly, despite the elimination of the cathepsin-cleavage site, immunoconjugates comprising a CL2A linker are apparently more efficacious in vivo than those comprising a CL2 linker.

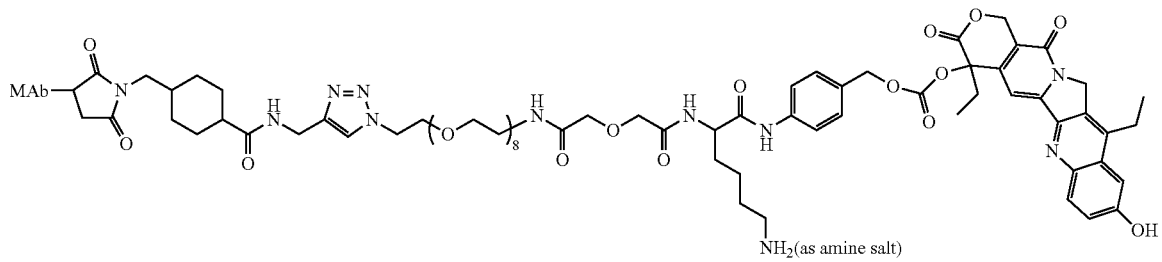

MAb-CL2A-SN-38

In a preferred embodiment, AA comprises a polypeptide moiety, preferably a di, tri or tetrapeptide, that is cleavable by intracellular peptidase. Examples are: Ala-Leu, Leu-Ala-Leu, and Ala-Leu-Ala-Leu (SEQ ID NO: 7) (Trouet et al., 1982).

In another preferred embodiment, the L1 component of the conjugate contains a defined polyethyleneglycol (PEG) spacer with 1-30 repeating monomeric units. In a further preferred embodiment, PEG is a defined PEG with 1-12 repeating monomeric units. The introduction of PEG may involve using heterobifunctionalized PEG derivatives which are available commercially. The heterobifunctional PEG may contain an azide or acetylene group.

In a preferred embodiment, L2 has a plurality of acetylene (or azide) groups, ranging from 2-40, but preferably 2-20, and more preferably 2-5, and a single antibody-binding moiety. In a representative example, the 12' component is appended to 2 acetylenic groups, resulting in the attachment of two azide-appended SN-38 molecules. The bonding to MAb may involve a succinimide.

In preferred embodiments, when the bifunctional drug contains a thiol-reactive moiety as the antibody-binding group, the thiols on the antibody are generated on the lysine groups of the antibody using a thiolating reagent. Methods for introducing thiol groups onto antibodies by modifications of MAb's lysine groups are well known in the art (Wong in *Chemistry of protein conjugation and cross-linking*, CRC Press, Inc., Boca Raton, Fla. (1991), pp 20-22). Alternatively, mild reduction of interchain disulfide bonds on the antibody (Willner et al., *Bioconjugate Chem.* 4:521-527 (1993)) using reducing agents such as dithiothreitol (DTT) can generate 7-to-10 thiols on the antibody; which has the advantage of incorporating multiple drug moieties in the interchain region of the MAb away from the antigen-binding region. In a more preferred embodiment, attachment of SN-38 to reduced disulfide sulfhydryl groups results in formation of an antibody-SN-38 immunoconjugate with 6 SN-38 moieties covalently attached per antibody molecule. Other methods of providing cysteine residues for attachment of drugs or other therapeutic agents are known, such as the use of cysteine engineered antibodies (see U.S. Pat. No. 7,521,541, the Examples section of which is incorporated herein by reference.)

In alternative preferred embodiments, the chemotherapeutic moiety is selected from the group consisting of doxorubicin (DOX), epirubicin, morpholinodoxorubicin (morpholino-DOX), cyanomorpholino-doxorubicin (cyanomorpholino-DOX), 2-pyrrolino-doxorubicin (2-PDOX), Pro-2PDOX, CPT, 10-hydroxy camptothecin, SN-38, topotecan, lurtotecan, 9-aminocamptothecin, 9-nitrocamptothecin, taxanes, geldanamycin, ansamycins, and epothilones. In a more preferred embodiment, the chemotherapeutic moiety is SN-38. Preferably, in the conjugates of the preferred embodiments, the antibody links to at least one chemotherapeutic moiety; preferably 1 to about 12 chemotherapeutic moieties; most preferably about 6 to about 12 chemotherapeutic moieties.

Furthermore, in a preferred embodiment, the linker component 'L2' comprises a thiol group that reacts with a thiol-reactive residue introduced at one or more lysine side chain amino groups of said antibody. In such cases, the antibody is pre-derivatized with a thiol-reactive group such as a maleimide, vinylsulfone, bromoacetamide, or iodoacetamide by procedures well described in the art.

In the context of this work, a process was surprisingly discovered by which CPT drug-linkers can be prepared wherein CPT additionally has a 10-hydroxyl group. This process involves, but is not limited to, the protection of the 10-hydroxyl group as a t-butyloxycarbonyl (BOC) derivative, followed by the preparation of the penultimate intermediate of the drug-linker conjugate. Usually, removal of the BOC group requires treatment with strong acid such as trifluoroacetic acid (TFA). Under these conditions, the CPT 20-O-linker carbonate, containing protecting groups to be removed, is also susceptible to cleavage, thereby giving rise to unmodified CPT. In fact, the rationale for using a mildly removable methoxytrityl (MMT) protecting group for the lysine side chain of the linker molecule, as enunciated in the art, was precisely to avoid this possibility (Walker et al., 2002). It was discovered that selective removal of phenolic BOC protecting group is possible by carrying out reactions for short durations, optimally 3-to-5 minutes. Under these conditions, the predominant product was that in which the 'BOC' at 10-hydroxyl position was removed, while the carbonate at '20' position was intact.

An alternative approach involves protecting the CPT analog's 10-hydroxy position with a group other than 'BOC', such that the the final product is ready for conjugation to antibodies without a need for deprotecting the 10-OH protecting group. The 10-hydroxy protecting group, which converts the 10-OH into a phenolic carbonate or a phenolic ester, is readily deprotected by physiological pH conditions or by esterases after in vivo administration of the conjugate. The faster removal of a phenolic carbonate at the 10 position vs. a tertiary carbonate at the 20 position of 10-hydroxycamptothecin under physiological condition has been described by He et al. (He et al., *Bioorganic & Medicinal Chemistry* 12: 4003-4008 (2004)). A 10-hydroxy protecting group on SN-38 can be 'COR' where R can be a substituted alkyl such as "$N(CH_3)_2$—$(CH_2)_n$—" where n is 1-10 and wherein the terminal amino group is optionally in the form of a quaternary salt for enhanced aqueous solubility, or a simple alkyl residue such as "$CH_3$—$(CH_2)_n$—" where n is 0-10, or it can be an alkoxy moiety such as "$CH_3$—$(CH_2)_n$—O—" where n is 0-10, or "$N(CH_3)_2$—$(CH_2)_n$—O—" where n is 2-10, or "$R_1O$—$(CH_2$—$CH_2$—$O)_n$—$CH_2$—$CH_2$—O—" where $R_1$ is ethyl or methyl and n is an integer with values of 0-10. These 10-hydroxy derivatives are readily prepared by treatment with the chloroformate of the chosen reagent, if the final derivative is to be a carbonate. Typically, the 10-hydroxy-containing camptothecin such as SN-38 is treated with a molar equivalent of the chloroformate in dimethylformamide using triethylamine as the base. Under these conditions, the 20-OH position is unaffected. For forming 10-O-esters, the acid chloride of the chosen reagent is used.

In a preferred process of the preparation of a conjugate of a drug derivative and an antibody of the general formula 1, wherein the descriptors L2, L1, AA and A-X are as described in earlier sections, the bifunctional drug moiety, [L2]-[L1]-[AA]$_m$-[A-X]-Drug is first prepared, followed by the conjugation of the bifunctional drug moiety to the antibody (indicated herein as "MAb").

In a preferred process of the preparation of a conjugate of a drug derivative and an antibody of the general formula 1, wherein the descriptors L2, L1, AA and A-OH are as described in earlier sections, the bifunctional drug moiety is prepared by first linking A-OH to the C-terminus of AA via an amide bond, followed by coupling the amine end of AA to a carboxylic acid group of L1. If AA is absent (i.e. m=0), A-OH is directly attached to L1 via an amide bond. The cross-linker, [L1]-[AA]$_m$-[A-OH], is attached to drug's hydroxyl or amino group, and this is followed by attachment to the L1 moiety, by taking recourse to the reaction between azide (or acetylene) and acetylene (or azide) groups in L1 and L2 via click chemistry.

In one embodiment, the antibody is a monoclonal antibody (MAb). In other embodiments, the antibody may be a multivalent and/or multispecific MAb. The antibody may be a murine, chimeric, humanized, or human monoclonal antibody, and said antibody may be in intact, fragment (Fab, Fab', F(ab)$_2$, F(ab')$_2$), or sub-fragment (single-chain constructs) form, or of an IgG1, IgG2a, IgG3, IgG4, IgA isotype, or submolecules therefrom.

In a preferred embodiment, the antibody binds to an antigen or epitope of an antigen expressed on a cancer or malignant cell. The cancer cell is preferably a cell from a hematopoietic tumor, carcinoma, sarcoma, melanoma or a glial tumor. In a most preferred embodiment, the antibody moiety is an anti-Trop-2 and the anti-Trop-2-SN-38 ADC is of use to treat any Trop-2-expressing cancer. In another preferred embodiment, the intracellularly-cleavable moiety may be cleaved after it is internalized into the cell upon binding by the MAb-drug conjugate to a receptor thereof.

General Antibody Techniques

Techniques for preparing monoclonal antibodies against virtually any target antigen are well known in the art. See, for example, Köhler and Milstein, *Nature* 256: 495 (1975); and Coligan et al. (eds.), CURRENT PROTOCOLS IN IMMUNOLOGY, VOL. 1, pages 2.5.1-2.6.7 (John Wiley & Sons 1991). Briefly, monoclonal antibodies can be obtained by injecting mice with a composition comprising an antigen, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures. The person of ordinary skill will realize that where antibodies are to be administered to human subjects, the antibodies will bind to human antigens.

MAbs can be isolated and purified from hybridoma cultures by a variety of well-established techniques. Such isolation techniques include affinity chromatography with Protein-A or Protein-G Sepharose, size-exclusion chromatography, and ion-exchange chromatography. See, for example, Coligan at pages 2.7.1-2.7.12 and pages 2.9.1-2.9.3. Also, see Baines et al., "Purification of Immunoglobulin G (IgG)," in METHODS IN MOLECULAR BIOLOGY, VOL. 10, pages 79-104 (The Humana Press, Inc. 1992).

After the initial raising of antibodies to the immunogen, the antibodies can be sequenced and subsequently prepared by recombinant techniques. Humanization and chimerization of murine antibodies and antibody fragments are well known to those skilled in the art, as discussed below.

The skilled artisan will realize that the claimed methods and compositions may utilize any of a wide variety of antibodies known in the art. Antibodies of use may be commercially obtained from a wide variety of known sources. For example, a variety of antibody secreting hybridoma lines are available from the American Type Culture Collection (ATCC, Manassas, Va.). A large number of antibodies against various disease targets, including but not limited to tumor-associated antigens, have been deposited at the ATCC and/or have published variable region sequences and are available for use in the claimed methods and compositions. See, e.g., U.S. Pat. Nos. 7,312,318; 7,282,567; 7,151,164; 7,074,403; 7,060,802; 7,056,509; 7,049,060; 7,045,132; 7,041,803; 7,041,802; 7,041,293; 7,038,018; 7,037,498; 7,012,133; 7,001,598; 6,998,468; 6,994,976; 6,994,852; 6,989,241; 6,974,863; 6,965,018; 6,964,854; 6,962,981; 6,962,813; 6,956,107; 6,951,924; 6,949,244; 6,946,129; 6,943,020; 6,939,547; 6,921,645; 6,921,645; 6,921,533; 6,919,433; 6,919,078; 6,916,475; 6,905,681; 6,899,879; 6,893,625; 6,887,468; 6,887,466; 6,884,594; 6,881,405; 6,878,812; 6,875,580; 6,872,568; 6,867,006; 6,864,062; 6,861,511; 6,861,227; 6,861,226; 6,838,282; 6,835,549; 6,835,370; 6,824,780; 6,824,778; 6,812,206; 6,793,924; 6,783,758; 6,770,450; 6,767,711; 6,764,688; 6,764,681; 6,764,679; 6,743,898; 6,733,981; 6,730,307; 6,720,155; 6,716,966; 6,709,653; 6,693,176; 6,692,908; 6,689,607; 6,689,362; 6,689,355; 6,682,737; 6,682,736; 6,682,734; 6,673,344; 6,653,104; 6,652,852; 6,635,482; 6,630,144; 6,610,833; 6,610,294; 6,605,441; 6,605,279; 6,596,852; 6,592,868; 6,576,745; 6,572,856; 6,566,076; 6,562,618; 6,545,130; 6,544,749; 6,534,058; 6,528,625; 6,528,269; 6,521,227; 6,518,404; 6,511,665; 6,491,915; 6,488,930; 6,482,598; 6,482,408; 6,479,247; 6,468,531; 6,468,529; 6,465,173; 6,461,823; 6,458,356; 6,455,044; 6,455,040; 6,451,310; 6,444,206; 6,441,143; 6,432,404; 6,432,402; 6,419,928; 6,413,726; 6,406,694; 6,403,770; 6,403,091; 6,395,276; 6,395,274; 6,387,350; 6,383,759; 6,383,484; 6,376,654; 6,372,215; 6,359,126; 6,355,481; 6,355,444; 6,355,245; 6,355,244; 6,346,246; 6,344,198; 6,340,571; 6,340,459; 6,331,175; 6,306,393; 6,254,868; 6,187,287; 6,183,744; 6,129,914; 6,120,767; 6,096,289; 6,077,499; 5,922,302; 5,874,540; 5,814,440; 5,798,229; 5,789,554; 5,776,456; 5,736,119; 5,716,595; 5,677,136; 5,587,459; 5,443,953; 5,525,338, the Examples section of each of which is incorporated herein by reference. These are exemplary only and a wide variety of other antibodies and their hybridomas are known in the art. The skilled artisan will realize that antibody sequences or antibody-secreting hybridomas against almost any disease-associated antigen may be obtained by a simple search of the ATCC, NCBI and/or USPTO databases for antibodies against a selected disease-associated target of interest. The antigen binding domains of the cloned antibodies may be amplified, excised, ligated into an expression vector, transfected into an adapted host cell and used for protein production, using standard techniques well known in the art. Isolated antibodies may be conjugated to therapeutic agents, such as camptothecins, using the techniques disclosed herein.

Chimeric and Humanized Antibodies

A chimeric antibody is a recombinant protein in which the variable regions of a human antibody have been replaced by the variable regions of, for example, a mouse antibody, including the complementarity-determining regions (CDRs) of the mouse antibody. Chimeric antibodies exhibit decreased immunogenicity and increased stability when administered to a subject. Methods for constructing chimeric antibodies are well known in the art (e.g., Leung et al., 1994, *Hybridoma* 13:469).

A chimeric monoclonal antibody may be humanized by transferring the mouse CDRs from the heavy and light variable chains of the mouse immunoglobulin into the corresponding variable domains of a human antibody. The mouse framework regions (FR) in the chimeric monoclonal antibody are also replaced with human FR sequences. To preserve the stability and antigen specificity of the humanized monoclonal, one or more human FR residues may be replaced by the mouse counterpart residues. Humanized monoclonal antibodies may be used for therapeutic treatment of subjects. Techniques for production of humanized monoclonal antibodies are well known in the art. (See, e.g., Jones et al., 1986, *Nature,* 321:522; Riechmann et al., *Nature,* 1988, 332:323; Verhoeyen et al., 1988, *Science,*

239:1534; Carter et al., 1992, *Proc. Nat'l Acad. Sci. USA*, 89:4285; Sandhu, *Crit. Rev. Biotech.*, 1992, 12:437; Tempest et al., 1991, *Biotechnology* 9:266; Singer et al., *J. Immun.*, 1993, 150:2844.)

Other embodiments may concern non-human primate antibodies. General techniques for raising therapeutically useful antibodies in baboons may be found, for example, in Goldenberg et al., WO 91/11465 (1991), and in Losman et al., *Int. J. Cancer* 46: 310 (1990). In another embodiment, an antibody may be a human monoclonal antibody. Such antibodies may be obtained from transgenic mice that have been engineered to produce specific human antibodies in response to antigenic challenge, as discussed below.

Human Antibodies

Methods for producing fully human antibodies using either combinatorial approaches or transgenic animals transformed with human immunoglobulin loci are known in the art (e.g., Mancini et al., 2004, *New Microbiol.* 27:315-28; Conrad and Scheller, 2005, *Comb. Chem. High Throughput Screen.* 8:117-26; Brekke and Loset, 2003, *Curr. Opin. Phamacol.* 3:544-50; each incorporated herein by reference). Such fully human antibodies are expected to exhibit even fewer side effects than chimeric or humanized antibodies and to function in vivo as essentially endogenous human antibodies. In certain embodiments, the claimed methods and procedures may utilize human antibodies produced by such techniques.

In one alternative, the phage display technique may be used to generate human antibodies (e.g., Dantas-Barbosa et al., 2005, *Genet. Mol. Res.* 4:126-40, incorporated herein by reference). Human antibodies may be generated from normal humans or from humans that exhibit a particular disease state, such as cancer (Dantas-Barbosa et al., 2005). The advantage to constructing human antibodies from a diseased individual is that the circulating antibody repertoire may be biased towards antibodies against disease-associated antigens.

In one non-limiting example of this methodology, Dantas-Barbosa et al. (2005) constructed a phage display library of human Fab antibody fragments from osteosarcoma patients. Generally, total RNA was obtained from circulating blood lymphocytes (Id.) Recombinant Fab were cloned from the μ, γ and κ chain antibody repertoires and inserted into a phage display library (Id.) RNAs were converted to cDNAs and used to make Fab cDNA libraries using specific primers against the heavy and light chain immunoglobulin sequences (Marks et al., 1991, *J. Mol. Biol.* 222:581-97, incorporated herein by reference). Library construction was performed according to Andris-Widhopf et al. (2000, In: *Phage Display Laboratory Manual*, Barbas et al. (eds), 1$^{st}$ edition, Cold Spring Harbor Laboratory Press, Cold Spring Harbor, N.Y. pp. 9.1 to 9.22, incorporated herein by reference). The final Fab fragments were digested with restriction endonucleases and inserted into the bacteriophage genome to make the phage display library. Such libraries may be screened by standard phage display methods. The skilled artisan will realize that this technique is exemplary only and any known method for making and screening human antibodies or antibody fragments by phage display may be utilized.

In another alternative, transgenic animals that have been genetically engineered to produce human antibodies may be used to generate antibodies against essentially any immunogenic target, using standard immunization protocols as discussed above. Methods for obtaining human antibodies from transgenic mice are described by Green et al., *Nature Genet.* 7:13 (1994), Lonberg et al., *Nature* 368:856 (1994), and Taylor et al., *Int. Immun.* 6:579 (1994). A non-limiting example of such a system is the XENOMOUSE® (e.g., Green et al., 1999, *J. Immunol. Methods* 231:11-23, incorporated herein by reference) from Abgenix (Fremont, Calif.), in which). In the XENOMOUSE® and similar animals, the mouse antibody genes have been inactivated and replaced by functional human antibody genes, while the remainder of the mouse immune system remains intact.

The transgenic mice were transformed with germline-configured YACs (yeast artificial chromosomes) that contained portions of the human IgH and Ig kappa loci, including the majority of the variable region sequences, along accessory genes and regulatory sequences. The human variable region repertoire may be used to generate antibody producing B cells, which may be processed into hybridomas by known techniques. A XENOMOUSE® immunized with a target antigen will produce human antibodies by the normal immune response, which may be harvested and/or produced by standard techniques discussed above. A variety of strains of genetically engineered mice are available, each of which is capable of producing a different class of antibody. Transgenically produced human antibodies have been shown to have therapeutic potential, while retaining the pharmacokinetic properties of normal human antibodies (Green et al., 1999). The skilled artisan will realize that the claimed compositions and methods are not limited to use of the XENOMOUSE® system but may utilize any transgenic animal that has been genetically engineered to produce human antibodies.

Production of Antibody Fragments

Some embodiments of the claimed methods and/or compositions may concern antibody fragments. Such antibody fragments may be obtained, for example, by pepsin or papain digestion of whole antibodies by conventional methods. For example, antibody fragments may be produced by enzymatic cleavage of antibodies with pepsin to provide a 5S fragment denoted F(ab')$_2$. This fragment may be further cleaved using a thiol reducing agent and, optionally, a blocking group for the sulfhydryl groups resulting from cleavage of disulfide linkages, to produce 3.5S Fab' monovalent fragments. Alternatively, an enzymatic cleavage using pepsin produces two monovalent Fab fragments and an Fc fragment. The two Fab fragments may be covalently conjugated to generate a F(ab)$_2$ antibody fragment. Exemplary methods for producing antibody fragments are disclosed in U.S. Pat. No. 4,036,945; U.S. Pat. No. 4,331,647; Nisonoff et al., 1960, Arch. Biochem. Biophys., 89:230; Porter, 1959, Biochem. J., 73:119; Edelman et al., 1967, METHODS IN ENZYMOLOGY, page 422 (Academic Press), and Coligan et al. (eds.), 1991, CURRENT PROTOCOLS IN IMMUNOLOGY, (John Wiley & Sons).

Other methods of cleaving antibodies, such as separation of heavy chains to form monovalent light-heavy chain fragments, further cleavage of fragments or other enzymatic, chemical or genetic techniques also may be used, so long as the fragments bind to the antigen that is recognized by the intact antibody. For example, Fv fragments comprise an association of V$_H$ and V$_L$ chains. This association can be noncovalent, as described in Inbar et al., 1972, *Proc. Nat'l. Acad. Sci. USA*, 69:2659. Alternatively, the variable chains may be linked by an intermolecular disulfide bond or cross-linked by chemicals such as glutaraldehyde. See Sandhu, 1992, *Crit. Rev. Biotech.*, 12:437.

Preferably, the Fv fragments comprise V$_H$ and V$_L$ chains connected by a peptide linker. These single-chain antigen binding proteins (scFv) are prepared by constructing a structural gene comprising DNA sequences encoding the V$_H$ and V$_L$ domains, connected by an oligonucleotides linker sequence. The structural gene is inserted into an expression vector that is subsequently introduced into a host cell, such as E. coli. The recombinant host cells synthesize a single polypeptide chain with a linker peptide bridging the two V domains. Methods for producing scFvs are well-known in the art. See Whitlow et al., 1991, *Methods: A Companion to Methods in Enzymology* 2:97; Bird et al., 1988, *Science*, 242:423; U.S. Pat. No. 4,946,778; Pack et al., 1993, *Bio/Technology*, 11:1271, and Sandhu, 1992, *Crit. Rev. Biotech.*, 12:437.

Another form of an antibody fragment is a single-domain antibody (dAb), sometimes referred to as a single chain antibody. Techniques for producing single-domain antibodies are well known in the art (see, e.g., Cossins et al., *Protein Expression and Purification*, 2007, 51:253-59; Shuntao et al., *Molec Immunol* 2006, 43:1912-19; Tanha et al., *J. Biol. Chem.* 2001, 276:24774-780). Other types of antibody fragments may comprise one or more complementarity-determining regions (CDRs). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See Larrick et al., 1991, *Methods: A Companion to Methods in Enzymology* 2:106; Ritter et al. (eds.), 1995, MONOCLONAL ANTIBODIES: PRODUCTION, ENGINEERING AND CLINICAL APPLICATION, pages 166-179 (Cambridge University Press); Birch et al., (eds.), 1995, MONOCLONAL ANTIBODIES: PRINCIPLES AND APPLICATIONS, pages 137-185 (Wiley-Liss, Inc.)

Antibody Variations

In certain embodiments, the sequences of antibodies, such as the Fc portions of antibodies, may be varied to optimize the physiological characteristics of the conjugates, such as the half-life in serum. Methods of substituting amino acid sequences in proteins are widely known in the art, such as by site-directed mutagenesis (e.g. Sambrook et al., *Molecular Cloning, A laboratory manual*, 2$^{nd}$ Ed, 1989). In preferred embodiments, the variation may involve the addition or removal of one or more glycosylation sites in the Fc sequence (e.g., U.S. Pat. No. 6,254,868, the Examples section of which is incorporated herein by reference). In other preferred embodiments, specific amino acid substitutions in the Fc sequence may be made (e.g., Hornick et al., 2000, *J Nucl Med* 41:355-62; Hinton et al., 2006, *J Immunol* 176:346-56; Petkova et al. 2006, *Int Immunol* 18:1759-69; U.S. Pat. No. 7,217,797; each incorporated herein by reference).

Target Antigens and Exemplary Antibodies

In a preferred embodiment, antibodies are used that recognize and/or bind to antigens that are expressed at high levels on target cells and that are expressed predominantly or exclusively on diseased cells versus normal tissues. More preferably, the antibodies internalize rapidly following binding. An exemplary rapidly internalizing antibody is the LL1 (anti-CD74) antibody, with a rate of internalization of approximately $8 \times 10^6$ antibody molecules per cell per day (e.g., Hansen et al., 1996, *Biochem* 1 320:293-300). Thus, a "rapidly internalizing" antibody may be one with an internalization rate of about $1 \times 10^6$ to about $1 \times 10^7$ antibody molecules per cell per day. Antibodies of use in the claimed compositions and methods may include MAbs with properties as recited above. Exemplary antibodies of use for therapy of, for example, cancer include but are not limited to LL1 (anti-CD74), LL2 or RFB4 (anti-CD22), veltuzumab (hA20, anti-CD20), rituximab (anti-CD20), obinutuzumab (GA101, anti-CD20), lambrolizumab (anti-PD-1 receptor), nivolumab (anti-PD-1 receptor), ipilimumab (anti-CTLA-4), RS7 (anti-Trop-2), PAM4 or KC4 (both anti-mucin), MN-14 (anti-carcinoembryonic antigen (CEA, also known as CD66e or CEACAM5)), MN-15 or MN-3 (anti-CEACAM6), Mu-9 (anti-colon-specific antigen-p), Immu 31 (an anti-alpha-fetoprotein), R1 (anti-IGF-1R), A19 (anti-CD19), TAG-72 (e.g., CC49), Tn, J591 or HuJ591 (anti-PSMA (prostate-specific membrane antigen)), AB-PG1-XG1-026 (anti-PSMA dimer), D2/B (anti-PSMA), G250 (an anti-carbonic anhydrase IX MAb), L243 (anti-HLA-DR) alemtuzumab (anti-CD52), bevacizumab (anti-VEGF), cetuximab (anti-EGFR), gemtuzumab (anti-CD33), ibritumomab tiuxetan (anti-CD20); panitumumab (anti-EGFR); tositumomab (anti-CD20); PAM4 (aka clivatuzumab, anti-MUC5ac) and trastuzumab (anti-ErbB2). Such antibodies are known in the art (e.g., U.S. Pat. Nos. 5,686,072; 5,874,540; 6,107,090; 6,183,744; 6,306,393; 6,653,104; 6,730.300; 6,899,864; 6,926,893; 6,962,702; 7,074,403; 7,230,084; 7,238,785; 7,238,786; 7,256,004; 7,282,567; 7,300,655; 7,312,318; 7,585,491; 7,612,180; 7,642,239; and U.S. Patent Application Publ. No. 20050271671; 20060193865; 20060210475; 20070087001; the Examples section of each incorporated herein by reference.) Specific known antibodies of use include hPAM4 (U.S. Pat. No. 7,282,567), hA20 (U.S. Pat. No. 7,151,164), hA19 (U.S. Pat. No. 7,109,304), hIMMU-31 (U.S. Pat. No. 7,300,655), hLL1 (U.S. Pat. No. 7,312,318), hLL2 (U.S. Pat. No. 5.789,554), hMu-9 (U.S. Pat. No. 7,387,772), hL243 (U.S. Pat. No. 7,612,180), hMN-14 (U.S. Pat. No. 6,676,924), hMN-15 (U.S. Pat. No. 8,287,865), hR1 (U.S. Pat. No. 9,441,043), hRS7 (U.S. Pat. No. 7,238,785), hMN-3 (U.S. Pat. No. 7,541,440), AB-PG1-XG1-026 (U.S. patent application Ser. No. 11/983,372, deposited as ATCC PTA-4405 and PTA-4406) and D2/B (WO 2009/130575) the text of each recited patent or application is incorporated herein by reference with respect to the Figures and Examples sections. In a particularly preferred embodiment, the antibody is hRS7.

Other useful antigens that may be targeted using the described conjugates include carbonic anhydrase IX, B7, CCL19, CCL21, CSAp, HER-2/neu, BrE3, CD1, CD1a, CD2, CD3, CD4, CD5, CD8, CD11A, CD14, CD15, CD16, CD18, CD19, CD20 (e.g., C2B8, hA20, 1F5 MAbs), CD21, CD22, CD23, CD25, CD29, CD30, CD32b, CD33, CD37, CD38, CD40, CD40L, CD44, CD45, CD46, CD52, CD54, CD55, CD59, CD64, CD67, CD70, CD74, CD79a, CD80, CD83, CD95, CD126, CD133, CD138, CD147, CD154, CEACAM5, CEACAM6, CTLA-4, alpha-fetoprotein (AFP), VEGF (e.g., bevacizumab, fibronectin splice variant), ED-B of fibronectin (e.g., L19), Trop-2, EGP-2 (e.g., 17-1A), EGF receptor (ErbB1) (e.g., cetuximab), ErbB2, ErbB3, Factor H, FHL-1, Flt-3, folate receptor, Ga 733, GRO-β, HMGB-1, hypoxia inducible factor (HIF), HM1.24, HER-2/neu, insulin-like growth factor (ILGF), IFN-γ, IFN-α, IFN-β, IFN-λ, IL-2R, IL-4R, IL-6R, IL-13R, IL-15R, IL-17R, IL-18R, IL-2, IL-6, IL-8, IL-12, IL-15, IL-17, IL-18, IL-25, IP-10, IGF-1R, Ia, HM1.24, gangliosides, HCG, the HLA-DR antigen to which L243 binds, CD66 antigens, i.e., CD66a-d or a combination thereof, MAGE, mCRP, MCP-1, MIP-1A, MIP-1B, macrophage migration-inhibitory factor (MIF), MUC1, MUC2, MUC3, MUC4, MUC5ac, placental growth factor (PIGF), PSA (prostate-specific antigen), PSMA, PAM4 antigen, PD-1, PD-L1, NCA-95, NCA-90, A3, A33, Ep-CAM, KS-1, Le(y), mesothelin, S100, tenascin, TAC, Tn antigen, Thomas-Friedenreich antigens, tumor necrosis antigens, tumor angiogenesis antigens, TNF-α, TRAIL receptor (R1 and R2), Trop-2, VEGFR, RANTES, T101, as well as cancer stem cell antigens, complement factors C3, C3a, C3b, C5a, C5, and an oncogene product.

A comprehensive analysis of suitable antigen (Cluster Designation, or CD) targets on hematopoietic malignant cells, as shown by flow cytometry and which can be a guide to selecting suitable antibodies for drug-conjugated immunotherapy, is Craig and Foon, *Blood* prepublished online Jan. 15, 2008; DOL 10.1182/blood-2007-11-120535.

The CD66 antigens consist of five different glycoproteins with similar structures, CD66a-e, encoded by the carcinoembryonic antigen (CEA) gene family members, BCG, CGM6, NCA, CGM1 and CEA, respectively. These CD66 antigens (e.g., CEACAM6) are expressed mainly in granulocytes, normal epithelial cells of the digestive tract and tumor cells of various tissues. Also included as suitable targets for cancers are cancer testis antigens, such as NY-ESO-1 (Theurillat et al., *Int. J Cancer* 2007; 120(11):2411-7), as well as CD79a in myeloid leukemia (Kozlov et al., *Cancer Genet. Cytogenet.* 2005; 163(1):62-7) and also B-cell diseases, and CD79b for non-Hodgkin's lymphoma (Poison et al., *Blood* 110(2):616-623). A number of the aforementioned antigens are disclosed in U.S. Provisional Application Ser. No. 60/426,379, entitled "Use of Multispecific, Non-covalent Complexes for Targeted Delivery of Therapeutics," filed Nov. 15, 2002. Cancer stem cells, which are ascribed to be more therapy-resistant precursor malignant cell populations (Hill and Perris, *J. Natl. Cancer Inst.* 2007; 99:1435-40), have antigens that can be targeted in certain cancer types, such as CD133 in prostate cancer (Maitland et al., *Ernst Schering Found. Sympos. Proc.* 2006; 5:155-79), non-small-cell lung cancer (Donnenberg et al., *J. Control Release* 2007; 122(3):385-91), and glioblastoma (Beier et al., *Cancer Res.* 2007; 67(9):4010-5), and CD44 in colorectal cancer (Dalerba et al., *Proc. Natl. Acad. Sci. USA* 2007; 104(24)10158-63), pancreatic cancer (Li et al., *Cancer Res.* 2007; 67(3):1030-7), and in head and neck squamous cell carcinoma (Prince et al., *Proc. Natl. Acad. Sci. USA* 2007; 104(3)973-8). Another useful target for breast cancer therapy is the LIV-1 antigen described by Taylor et al. (*Biochem. J.* 2003; 375:51-9). The CD47 antigen is a further useful target for cancer stem cells (see, e.g., Naujokat et al., 2014, Immunotherapy 6:290-308; Goto et al., 2014, Eur J Cancer 50:1836-46; Unanue, 2013, Proc Natl Acad Sci USA 110:10886-7).

For multiple myeloma therapy, suitable targeting antibodies have been described against, for example, CD38 and CD138 (Stevenson, *Mol Med* 2006; 12(11-12):345-346; Tassone et al., *Blood* 2004; 104(12):3688-96), CD74 (Stein et al., ibid.), CS 1 (Tai et al., *Blood* 2008; 112(4):1329-37, and CD40 (Tai et al., 2005; *Cancer Res.* 65(13):5898-5906).

Checkpoint inhibitor antibodies have been used in cancer therapy. Immune checkpoints refer to inhibitory pathways in the immune system that are responsible for maintaining self-tolerance and modulating the degree of immune system response to minimize peripheral tissue damage. However, tumor cells can also activate immune system checkpoints to decrease the effectiveness of immune response against tumor tissues. Exemplary checkpoint inhibitor antibodies against cytotoxic T-lymphocyte antigen 4 (CTLA4, also known as CD152), programmed cell death protein 1 (PD-1, also known as CD279) and programmed cell death 1 ligand 1 (PD-L1, also known as CD274), may be used in combination with one or more other agents to enhance the effectiveness of immune response against disease cells, tissues or pathogens. Exemplary anti-PD-1 antibodies include lambrolizumab (MK-3475, MERCK), nivolumab (BMS-936558, BRISTOL-MYERS SQUIBB), AMP-224 (MERCK), and pidilizumab (CT-011, CURETECH LTD.). Anti-PD-1 antibodies are commercially available, for example from ABCAM® (AB137132), BIOLEGEND® (EH12.2H7, RMP1-14) and AFFYMETRIX EBIOSCIENCE (J105, J116, MIH4). Exemplary anti-PD-L1 antibodies include MDX-1105 (MEDAREX), MEDI4736 (MEDIMMUNE) MPDL3280A (GENENTECH) and BMS-936559 (BRISTOL-MYERS SQUIBB). Anti-PD-L1 antibodies are also commercially available, for example from AFFYMETRIX EBIOSCIENCE (MIH1). Exemplary anti-CTLA4 antibodies include ipilimumab (Bristol-Myers Squibb) and tremelimumab (PFIZER). Anti-PD1 antibodies are commercially available, for example from ABCAM® (AB134090), SINO BIOLOGICAL INC. (11159-H03H, 11159-H08H), and THERMO SCIENTIFIC PIERCE (PAS-29572, PA5-23967, PA5-26465, MA1-12205, MA1-35914). Ipilimumab has recently received FDA approval for treatment of metastatic melanoma (Wada et al., 2013, J Transl Med 11:89).

Macrophage migration inhibitory factor (MIF) is an important regulator of innate and adaptive immunity and apoptosis. It has been reported that CD74 is the endogenous receptor for MIF (Leng et al., 2003, *J Exp Med* 197:1467-76). The therapeutic effect of antagonistic anti-CD74 antibodies on MIF-mediated intracellular pathways may be of use for treatment of a broad range of disease states, such as cancers of the bladder, prostate, breast, lung, colon and chronic lymphocytic leukemia (e.g., Meyer-Siegler et al., 2004, *BMC Cancer* 12:34; Shachar & Haran, 2011, *Leuk Lymphoma* 52:1446-54); autoimmune diseases such as rheumatoid arthritis and systemic lupus erythematosus (Morand & Leech, 2005, *Front Biosci* 10:12-22; Shachar & Haran, 2011, *Leuk Lymphoma* 52:1446-54); kidney diseases such as renal allograft rejection Lan, 2008, *Nephron Exp Nephrol.* 109:e79-83); and numerous inflammatory diseases (Meyer-Siegler et al., 2009, *Mediators Inflamm* epub Mar. 22, 2009; Takahashi et al., 2009, *Respir Res* 10:33; Milatuzumab (hLL1) is an exemplary anti-CD74 antibody of therapeutic use for treatment of MIF-mediated diseases.

Anti-TNF-α antibodies are known in the art and may be of use to treat various diseases. Known antibodies against TNF-α include the human antibody CDP571 (Ofei et al., 2011, *Diabetes* 45:881-85); murine antibodies MTNFAI, M2TNFAI, M3TNFAI, M3TNFABI, M302B and M303 (Thermo Scientific, Rockford, Ill.); infliximab (Centocor, Malvern, Pa.); certolizumab pegol (UCB, Brussels, Belgium); and adalimumab (Abbott, Abbott Park, Ill.). These and many other known anti-TNF-α antibodies may be used in the claimed methods and compositions.

In another preferred embodiment, antibodies are used that internalize rapidly and are then re-expressed, processed and presented on cell surfaces, enabling continual uptake and accretion of circulating conjugate by the cell. An example of a most-preferred antibody/antigen pair is LL1, an anti-CD74 MAb (invariant chain, class II-specific chaperone, Ii) (see, e.g., U.S. Pat. Nos. 6,653,104; 7,312,318; the Examples section of each incorporated herein by reference). The CD74 antigen is highly expressed on B-cell lymphomas (including multiple myeloma) and leukemias, certain T-cell lymphomas, melanomas, colonic, lung, and renal cancers, glioblastomas, and certain other cancers (Ong et al., *Immunology* 98:296-302 (1999)). A review of the use of CD74 antibodies in cancer is contained in Stein et al., *Clin Cancer Res.* 2007 Sep. 15; 13(18 Pt 2):55565-5563s, incorporated herein by reference.

The diseases that are preferably treated with anti-CD74 antibodies include, but are not limited to, non-Hodgkin's lymphoma, Hodgkin's disease, melanoma, lung, renal, colonic cancers, glioblastome multiforme, histiocytomas, myeloid leukemias, and multiple myeloma. Continual expression of the CD74 antigen for short periods of time on the surface of target cells, followed by internalization of the antigen, and re-expression of the antigen, enables the targeting LL1 antibody to be internalized along with any chemotherapeutic moiety it carries. This allows a high, and therapeutic, concentration of LL1-chemotherapeutic drug conjugate to be accumulated inside such cells. Internalized LL1-chemotherapeutic drug conjugates are cycled through lysosomes and endosomes, and the chemotherapeutic moiety is released in an active form within the target cells.

The antibodies discussed above and other known antibodies against disease-associated antigens may be used as CPT-conjugates, more preferably SN-38-conjugates, in the practice of the claimed methods and compositions. In a most preferred embodiment, the drug-conjugated antibody is an anti-Trop-2-SN-38 (e.g., hRS7-SN-38) conjugate.

Bispecific and Multispecific Antibodies

Bispecific antibodies are useful in a number of biomedical applications. For instance, a bispecific antibody with binding sites for a tumor cell surface antigen and for a T-cell surface receptor can direct the lysis of specific tumor cells by T cells. Bispecific antibodies recognizing gliomas and the CD3 epitope on T cells have been successfully used in treating brain tumors in human patients (Nitta, et al. *Lancet.* 1990; 355:368-371). A preferred bispecific antibody is an anti-CD3 X anti-Trop-2 antibody. In alternative embodiments, an anti-CD3 antibody or fragment thereof may be attached to an antibody or fragment against a B-cell associated antigen, such as anti-CD3 X anti-CD19, anti-CD3 X anti-CD20, anti-CD3 X anti-CD22, anti-CD3 X anti-HLA-DR or anti-CD3 X anti-CD74. In certain embodiments, the techniques and compositions for therapeutic agent conjugation disclosed herein may be used with bispecific or multispecific antibodies as the targeting moieties.

Numerous methods to produce bispecific or multispecific antibodies are known, as disclosed, for example, in U.S. Pat. No. 7,405,320, the Examples section of which is incorporated herein by reference. Bispecific antibodies can be produced by the quadroma method, which involves the fusion of two different hybridomas, each producing a monoclonal antibody recognizing a different antigenic site (Milstein and Cuello, *Nature*, 1983; 305:537-540).

Another method for producing bispecific antibodies uses heterobifunctional cross-linkers to chemically tether two different monoclonal antibodies (Staerz, et al. *Nature*, 1985; 314:628-631; Perez, et al. *Nature*, 1985; 316:354-356). Bispecific antibodies can also be produced by reduction of each of two parental monoclonal antibodies to the respective half molecules, which are then mixed and allowed to reoxidize to obtain the hybrid structure (Staerz and Bevan. *Proc Natl Acad Sci USA.* 1986; 83:1453-1457). Another alternative involves chemically cross-linking two or three separately purified Fab' fragments using appropriate linkers. (See, e.g., European Patent Application 0453082).

Other methods include improving the efficiency of generating hybrid hybridomas by gene transfer of distinct selectable markers via retrovirus-derived shuttle vectors into respective parental hybridomas, which are fused subsequently (DeMonte, et al. *Proc Natl Acad Sci USA.* 1990, 87:2941-2945); or transfection of a hybridoma cell line with expression plasmids containing the heavy and light chain genes of a different antibody.

Cognate $V_H$ and $V_L$ domains can be joined with a peptide linker of appropriate composition and length (usually consisting of more than 12 amino acid residues) to form a single-chain Fv (scFv) with binding activity. Methods of manufacturing scFvs are disclosed in U.S. Pat. No. 4,946,778 and U.S. Pat. No. 5,132,405, the Examples section of each of which is incorporated herein by reference. Reduction of the peptide linker length to less than 12 amino acid residues prevents pairing of $V_H$ and $V_L$ domains on the same chain and forces pairing of $V_H$ and $V_L$ domains with complementary domains on other chains, resulting in the formation of functional multimers. Polypeptide chains of $V_H$ and $V_L$ domains that are joined with linkers between 3 and 12 amino acid residues form predominantly dimers (termed diabodies). With linkers between 0 and 2 amino acid residues, trimers (termed triabody) and tetramers (termed tetrabody) are favored, but the exact patterns of oligomerization appear to depend on the composition as well as the orientation of V-domains ($V_H$-linker-$V_L$ or $V_L$-linker-$V_H$), in addition to the linker length.

These techniques for producing multispecific or bispecific antibodies exhibit various difficulties in terms of low yield, necessity for purification, low stability or the labor-intensiveness of the technique. More recently, a technique known as "dock and lock" (DNL®) has been utilized to produce combinations of virtually any desired antibodies, antibody fragments and other effector molecules (see, e.g., U.S. Pat. Nos. 7,521,056; 7,527,787; 7,534,866; 7,550,143; 7,666,400; 7,858,070; 7,871,622; 7,906,121; 7,906,118; 8,163,291; 7,901,680; 7,981,398; 8,003,111 and 8,034,352, the Examples section of each of which incorporated herein by reference). The technique utilizes complementary protein binding domains, referred to as anchoring domains (AD) and dimerization and docking domains (DDD), which bind to each other and allow the assembly of complex structures, ranging from dimers, trimers, tetramers, quintamers and hexamers. These form stable complexes in high yield without requirement for extensive purification. The DNL® technique allows the assembly of monospecific, bispecific or multispecific antibodies. Any of the techniques known in the art for making bispecific or multispecific antibodies may be utilized in the practice of the presently claimed methods.

Antibody Allotypes

Immunogenicity of therapeutic antibodies is associated with increased risk of infusion reactions and decreased duration of therapeutic response (Baert et al., 2003, *N Engl J Med* 348:602-08). The extent to which therapeutic antibodies induce an immune response in the host may be determined in part by the allotype of the antibody (Stickler et al., 2011, *Genes and Immunity* 12:213-21). Antibody allotype is related to amino acid sequence variations at specific locations in the constant region sequences of the antibody. The allotypes of IgG antibodies containing a heavy chain γ-type constant region are designated as Gm allotypes (1976, *J Immunol* 117:1056-59).

For the common IgG1 human antibodies, the most prevalent allotype is G1m1 (Stickler et al., 2011, *Genes and Immunity* 12:213-21). However, the G1m3 allotype also occurs frequently in Caucasians (Id.). It has been reported that G1m1 antibodies contain allotypic sequences that tend to induce an immune response when administered to non-G1m1 (nG1m1) recipients, such as G1m3 patients (Id.). Non-G1m1 allotype antibodies are not as immunogenic when administered to G1m1 patients (Id.).

The human G1m1 allotype comprises the amino acids aspartic acid at Kabat position 356 and leucine at Kabat position 358 in the CH3 sequence of the heavy chain IgG1.

The nG1m1 allotype comprises the amino acids glutamic acid at Kabat position 356 and methionine at Kabat position 358. Both G1m1 and nG1m1 allotypes comprise a glutamic acid residue at Kabat position 357 and the allotypes are sometimes referred to as DEL and EEM allotypes. A non-limiting example of the heavy chain constant region sequences for G1m1 and nG1m1 allotype antibodies is shown for the exemplary antibodies rituximab (SEQ ID NO:8) and veltuzumab (SEQ ID NO:9).

```
Rituximab heavy chain variable region sequence
                                        (SEQ ID NO: 8)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKAEP

KSCDKTHTCPPCPAPELLGGPSVFLEPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPGK

Veltuzumab heavy chain variable region
                                        (SEQ ID NO: 9)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKRVEP

KSCDKTHTCPPCPAPELLGGPSVFLEPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVMHEALHNHYTQKSLSLSPGK
```

Jefferis and Lefranc (2009, mAbs 1:1-7) reviewed sequence variations characteristic of IgG allotypes and their effect on immunogenicity. They reported that the G1m3 allotype is characterized by an arginine residue at Kabat position 214, compared to a lysine residue at Kabat 214 in the G1m17 allotype. The nG1m1,2 allotype was characterized by glutamic acid at Kabat position 356, methionine at Kabat position 358 and alanine at Kabat position 431. The G1m1,2 allotype was characterized by aspartic acid at Kabat position 356, leucine at Kabat position 358 and glycine at Kabat position 431. In addition to heavy chain constant region sequence variants, Jefferis and Lefranc (2009) reported allotypic variants in the kappa light chain constant region, with the Km1 allotype characterized by valine at Kabat position 153 and leucine at Kabat position 191, the Km1,2 allotype by alanine at Kabat position 153 and leucine at Kabat position 191, and the Km3 allotypoe characterized by alanine at Kabat position 153 and valine at Kabat position 191.

With regard to therapeutic antibodies, veltuzumab and rituximab are, respectively, humanized and chimeric IgG1 antibodies against CD20, of use for therapy of a wide variety of hematological malignancies. Table 1 compares the allotype sequences of rituximab vs. veltuzumab. As shown in Table 1, rituximab (G1m17,1) is a DEL allotype IgG1, with an additional sequence variation at Kabat position 214 (heavy chain CH1) of lysine in rituximab vs. arginine in veltuzumab. It has been reported that veltuzumab is less immunogenic in subjects than rituximab (see, e.g., Morchhauser et al., 2009, J Clin Oncol 27:3346-53; Goldenberg et al., 2009, Blood 113:1062-70; Robak & Robak, 2011, BioDrugs 25:13-25), an effect that has been attributed to the difference between humanized and chimeric antibodies. However, the difference in allotypes between the EEM and DEL allotypes likely also accounts for the lower immunogenicity of veltuzumab.

TABLE 1

Allotypes of Rituximab vs. Veltuzumab

| | Complete allotype | Heavy chain position and associated allotypes | | |
|---|---|---|---|---|
| | | 214 (allotype) | 356/358 (allotype) | 431 (allotype) |
| Rituximab | G1m17,1 | K 17 | D/L 1 | A — |
| Veltuzumab | G1m3 | R 3 | E/M — | A — |

In order to reduce the immunogenicity of therapeutic antibodies in individuals of nG1m1 genotype, it is desirable to select the allotype of the antibody to correspond to the G1m3 allotype, characterized by arginine at Kabat 214, and the nG1m1,2 null-allotype, characterized by glutamic acid at Kabat position 356, methionine at Kabat position 358 and alanine at Kabat position 431. Surprisingly, it was found that repeated subcutaneous administration of G1m3 antibodies over a long period of time did not result in a significant immune response. In alternative embodiments, the human IgG4 heavy chain in common with the G1m3 allotype has arginine at Kabat 214, glutamic acid at Kabat 356, methionine at Kabat 359 and alanine at Kabat 431. Since immunogenicity appears to relate at least in part to the residues at those locations, use of the human IgG4 heavy chain constant region sequence for therapeutic antibodies is also a preferred embodiment. Combinations of G1m3 IgG1 antibodies with IgG4 antibodies may also be of use for therapeutic administration.

Conjugation Protocols

Antibodies or fragments thereof may be conjugated to one or more therapeutic or diagnostic agents. The therapeutic agents do not need to be the same but can be different, e.g. a drug and a radioisotope. For example, $^{131}$I can be incorporated into a tyrosine of an antibody or fusion protein and a drug attached to an epsilon amino group of a lysine residue. Therapeutic and diagnostic agents also can be attached, for example to reduced SH groups and/or to carbohydrate side chains. Many methods for making covalent or non-covalent conjugates of therapeutic or diagnostic agents with antibodies or fusion proteins are known in the art and any such known method may be utilized.

A therapeutic or diagnostic agent can be attached at the hinge region of a reduced antibody component via disulfide bond formation. Alternatively, such agents can be attached using a heterobifunctional cross-linker, such as N-succinyl 3-(2-pyridyldithio)propionate (SPDP). Yu et al., Int. J. Cancer 56: 244 (1994). General techniques for such conjugation are well-known in the art. See, for example, Wong, CHEMISTRY OF PROTEIN CONJUGATION AND CROSS-LINKING (CRC Press 1991); Upeslacis et al., "Modification of Antibodies by Chemical Methods," in MONOCLONAL ANTIBODIES: PRINCIPLES AND APPLICATIONS, Birch et al. (eds.), pages 187-230 (Wiley-Liss, Inc. 1995); Price, "Production and Characterization of Synthetic Peptide-Derived Antibodies," in MONOCLONAL ANTIBODIES: PRODUCTION, ENGINEERING AND CLINICAL APPLICATION, Ritter et al. (eds.), pages 60-84 (Cambridge University Press 1995). Alternatively, the therapeutic or diagnostic agent can be conjugated via a carbohydrate moiety in the Fc region of the antibody. The carbohydrate group can be used to increase the loading of the same agent that is bound to a thiol group, or the carbohydrate moiety can be used to bind a different therapeutic or diagnostic agent.

Methods for conjugating peptides to antibody components via an antibody carbohydrate moiety are well-known to those of skill in the art. See, for example, Shih et al., *Int. J. Cancer* 41: 832 (1988); Shih et al., *Int. J. Cancer* 46: 1101 (1990); and Shih et al., U.S. Pat. No. 5,057,313, incorporated herein in their entirety by reference. The general method involves reacting an antibody component having an oxidized carbohydrate portion with a carrier polymer that has at least one free amine function. This reaction results in an initial Schiff base (imine) linkage, which can be stabilized by reduction to a secondary amine to form the final conjugate.

The Fc region may be absent if the antibody used as the antibody component of the immunoconjugate is an antibody fragment. However, it is possible to introduce a carbohydrate moiety into the light chain variable region of a full length antibody or antibody fragment. See, for example, Leung et al., *J. Immunol.* 154: 5919 (1995); Hansen et al., U.S. Pat. No. 5,443,953 (1995), Leung et al., U.S. Pat. No. 6,254,868, incorporated herein by reference in their entirety. The engineered carbohydrate moiety is used to attach the therapeutic or diagnostic agent.

The preferred conjugation protocol is based on a thiol-maleimide, a thiol-vinylsulfone, a thiol-bromoacetamide, or a thiol-iodoacetamide reaction that is facile at neutral or acidic pH. This obviates the need for higher pH conditions for conjugations as, for instance, would be necessitated when using active esters. Further details of exemplary conjugation protocols are described below in the Examples section.

Therapeutic Treatment

In another aspect, the invention relates to a method of treating a subject, comprising administering to a subject a therapeutically effective amount of an antibody-drug conjugate (ADC) as described herein. Diseases that may be treated with the ADCs described herein include, but are not limited to B-cell malignancies (e.g., non-Hodgkin's lymphoma, mantle cell lymphoma, multiple myeloma, Hodgkin's lymphoma, diffuse large B cell lymphoma, Burkitt lymphoma, follicular lymphoma, acute lymphocytic leukemia, chronic lymphocytic leukemia, hairy cell leukemia) using, for example an anti-CD22 antibody such as the hLL2 MAb (epratuzumab, see U.S. Pat. No. 6,183,744), against another CD22 epitope (hRFB4) or antibodies against other B cell antigens, such as CD19, CD20, CD21, CD22, CD23, CD37, CD40, CD40L, CD52, CD74, CD80 or HLA-DR. Other diseases include, but are not limited to, adenocarcinomas of endodermally-derived digestive system epithelia, cancers such as breast cancer and non-small cell lung cancer, and other carcinomas, sarcomas, glial tumors, myeloid leukemias, etc. In particular, antibodies against an antigen, e.g., an oncofetal antigen, produced by or associated with a malignant solid tumor or hematopoietic neoplasm, e.g., a gastrointestinal, stomach, colon, esophageal, liver, lung, breast, pancreatic, liver, prostate, ovarian, testicular, brain, bone, urothelial or lymphatic tumor, a sarcoma or a melanoma, are advantageously used. Such therapeutics can be given once or repeatedly, depending on the disease state and tolerability of the conjugate, and can also be used optionally in combination with other therapeutic modalities, such as surgery, external radiation, radioimmunotherapy, immunotherapy, chemotherapy, antisense therapy, interference RNA therapy, gene therapy, and the like. Each combination will be adapted to the tumor type, stage, patient condition and prior therapy, and other factors considered by the managing physician.

As used herein, the term "subject" refers to any animal (i.e., vertebrates and invertebrates) including, but not limited to mammals, including humans. It is not intended that the term be limited to a particular age or sex. Thus, adult and newborn subjects, as well as fetuses, whether male or female, are encompassed by the term. Doses given herein are for humans, but can be adjusted to the size of other mammals, as well as children, in accordance with weight or square meter size.

In a preferred embodiment, therapeutic conjugates comprising an anti-Trop-2 antibody such as the hRS7 MAb can be used to treat carcinomas such as carcinomas of the esophagus, pancreas, lung, stomach, colon and rectum, urinary bladder, breast, ovary, uterus, kidney and prostate, as disclosed in U.S. Pat. Nos. 7,238,785; 7,517,964 and 8,084,583, the Examples section of which is incorporated herein by reference. An hRS7 antibody is a humanized antibody that comprises light chain complementarity-determining region (CDR) sequences CDR1 (KASQDVSIAVA, SEQ ID NO:1); CDR2 (SASYRYT, SEQ ID NO:2); and CDR3 (QQHYITPLT, SEQ ID NO:3) and heavy chain CDR sequences CDR1 (NYGMN, SEQ ID NO:4); CDR2 (WINTYTGEPTYTDDFKG, SEQ ID NO:5) and CDR3 (GGFGSSYWYFDV, SEQ ID NO:6)

In a preferred embodiment, the antibodies that are used in the treatment of human disease are human or humanized (CDR-grafted) versions of antibodies; although murine and chimeric versions of antibodies can be used. Same species IgG molecules as delivery agents are mostly preferred to minimize immune responses. This is particularly important when considering repeat treatments. For humans, a human or humanized IgG antibody is less likely to generate an anti-IgG immune response from patients. Antibodies such as hLL1 and hLL2 rapidly internalize after binding to internalizing antigen on target cells, which means that the chemotherapeutic drug being carried is rapidly internalized into cells as well. However, antibodies that have slower rates of internalization can also be used to effect selective therapy.

In another preferred embodiment, a therapeutic agent used in combination with the camptothecin conjugate of this invention may comprise one or more isotopes. Radioactive isotopes useful for treating diseased tissue include, but are not limited to—$^{111}$In, $^{177}$Lu, $^{212}$Bi, $^{213}$Bi, $^{211}$At, $^{62}$Cu, $^{67}$Cu, $^{90}$Y, $^{125}$I, $^{131}$I, $^{32}$P, $^{33}$P, $^{47}$Sc, $^{111}$Ag, $^{67}$Ga, $^{142}$Pr, $^{153}$Sm, $^{161}$Tb, $^{166}$Dy, $^{166}$Ho, $^{186}$Re, $^{188}$Re, $^{189}$Re, $^{212}$Pb, $^{223}$Ra, $^{225}$Ac, $^{59}$Fe, $^{75}$Se, $^{77}$As, $^{89}$Sr, $^{99}$Mo, $^{105}$Rh, $^{109}$Pd, $^{143}$Pr, $^{149}$Pm, $^{169}$Er, $^{194}$Ir, $^{198}$Au, $^{227}$Th and $^{211}$Pb. The therapeutic radionuclide preferably has a decay-energy in the range of 20 to 6,000 keV, preferably in the ranges 60 to 200 keV for an Auger emitter, 100-2,500 keV for a beta emitter, and 4,000-6,000 keV for an alpha emitter. Maximum decay energies of useful beta-particle-emitting nuclides are preferably 20-5,000 keV, more preferably 100-4,000 keV, and most preferably 500-2,500 keV. Also preferred are radionuclides that substantially decay with Auger-emitting particles. For example, Co-58, Ga-67, Br-80m, Tc-99m, Rh-103m, Pt-109, In-111, Sb-119, I-125, Ho-161, Os-189m and Ir-192. Decay energies of useful beta-particle-emitting nuclides are preferably <1,000 keV, more preferably <100 keV, and most preferably <70 keV. Also preferred are radionuclides that substantially decay with generation of alpha-particles. Such radionuclides include, but are not limited to: Dy-152, At-211, Bi-212, Ra-223, Rn-219, Po-215, Bi-211, Ac-225, Fr-221, At-217, Bi-213, Th-227 and Fm-255. Decay energies of useful alpha-particle-emitting radionuclides are preferably 2,000-10,000 keV, more preferably 3,000-8,000 keV, and most preferably 4,000-7,000 keV. Additional potential radioisotopes of use include $^{11}$C, $^{13}$N, $^{15}$O, $^{75}$Br, $^{198}$Au, $^{224}$Ac, $^{126}$I, $^{133}$I, $^{77}$Br, $^{113m}$In, $^{95}$Ru, $^{97}$Ru, $^{103}$Ru, $^{105}$Ru, $^{107}$Hg, $^{203}$Hg, $^{121m}$Te, $^{122m}$Te, $^{125m}$Te, $^{165}$Tm, $^{167}$Tm, $^{168}$Tm, $^{197}$Pt, $^{109}$Pd, $^{105}$Rh, $^{142}$Pr, $^{143}$Pr, $^{161}$Tb, $^{166}$Ho, $^{199}$Au, $^{57}$Co, $^{58}$Co, $^{51}$Cr, $^{59}$Fe, $^{75}$Se, $^{201}$Tl, $^{225}$Ac, $^{76}$Br, $^{169}$Yb, and the like.

Radionuclides and other metals may be delivered, for example, using chelating groups attached to an antibody or conjugate. Macrocyclic chelates such as NOTA, DOTA, and TETA are of use with a variety of metals and radiometals, most particularly with radionuclides of gallium, yttrium and copper, respectively. Such metal-chelate complexes can be made very stable by tailoring the ring size to the metal of interest. Other ring-type chelates, such as macrocyclic polyethers for complexing $^{223}$Ra, may be used.

Therapeutic agents of use in combination with the camptothecin conjugates described herein also include, for example, chemotherapeutic drugs such as vinca alkaloids, anthracyclines, epipodophyllotoxins, taxanes, antimetabolites, tyrosine kinase inhibitors, alkylating agents, antibiotics, Cox-2 inhibitors, antimitotics, antiangiogenic and proapoptotic agents, particularly doxorubicin, methotrexate, taxol, other camptothecins, and others from these and other classes of anticancer agents, and the like. Other cancer chemotherapeutic drugs include nitrogen mustards, alkyl sulfonates, nitrosoureas, triazenes, folic acid analogs, pyrimidine analogs, purine analogs, platinum coordination complexes, hormones, and the like. Suitable chemotherapeutic agents are described in REMINGTON'S PHARMACEUTICAL SCIENCES, 19th Ed. (Mack Publishing Co. 1995), and in GOODMAN AND GILMAN'S THE PHARMACOLOGICAL BASIS OF THERAPEUTICS, 7th Ed. (MacMillan Publishing Co. 1985), as well as revised editions of these publications. Other suitable chemotherapeutic agents, such as experimental drugs, are known to those of skill in the art.

Exemplary drugs of use include, but are not limited to, 5-fluorouracil, afatinib, aplidin, azaribine, anastrozole, anthracyclines, axitinib, AVL-101, AVL-291, bendamustine, bleomycin, bortezomib, bosutinib, bryostatin-1, busulfan, calicheamycin, camptothecin, carboplatin, 10-hydroxycamptothecin, carmustine, celebrex, chlorambucil, cisplatin (CDDP), Cox-2 inhibitors, irinotecan (CPT-11), SN-38, carboplatin, cladribine, camptothecans, crizotinib, cyclophosphamide, cytarabine, dacarbazine, dasatinib, dinaciclib, docetaxel, dactinomycin, daunorubicin, doxorubicin, 2-pyrrolinodoxorubicine (2P-DOX), cyano-morpholino doxorubicin, doxorubicin glucuronide, epirubicin glucuronide, erlotinib, estramustine, epidophyllotoxin, erlotinib, entinostat, estrogen receptor binding agents, etoposide (VP16), etoposide glucuronide, etoposide phosphate, exemestane, fingolimod, floxuridine (FUdR), 3',5'-P-dioleoyl-FudR (FUdR-dO), fludarabine, flutamide, farnesyl-protein transferase inhibitors, flavopiridol, fostamatinib, ganetespib, GDC-0834, GS-1101, gefitinib, gemcitabine, hydroxyurea, ibrutinib, idarubicin, idelalisib, ifosfamide, imatinib, L-asparaginase, lapatinib, lenolidamide, leucovorin, LFM-A13, lomustine, mechlorethamine, melphalan, mercaptopurine, 6-mercaptopurine, methotrexate, mitoxantrone, mithramycin, mitomycin, mitotane, navelbine, neratinib, nilotinib, nitrosurea, olaparib, plicomycin, procarbazine, paclitaxel, PCI-32765, pentostatin, PSI-341, raloxifene, semustine, sorafenib, streptozocin, SU11248, sunitinib, tamoxifen, temazolomide (an aqueous form of DTIC), transplatinum, thalidomide, thioguanine, thiotepa, teniposide, topotecan, uracil mustard, vatalanib, vinorelbine, vinblastine, vincristine, vinca alkaloids and ZD1839. Such agents may be part of the conjugates described herein or may alternatively be administered in combination with the described conjugates, either prior to, simultaneously with or after the conjugate. Alternatively, one or more therapeutic naked antibodies as are known in the art may be used in combination with the described conjugates. Exemplary therapeutic naked antibodies are described above.

In preferred embodiments, a therapeutic agent to be used in combination with a DNA-breaking antibody conjugate (e.g., an SN-38-ADC) is a microtubule inhibitor, such as a vinca alkaloid, a taxanes, a maytansinoid or an auristatin. Exemplary known microtubule inhibitors include paclitaxel, vincristine, vinblastine, mertansine, epothilone, docetaxel, discodermolide, combrestatin, podophyllotoxin, CI-980, phenylahistins, steganacins, curacins, 2-methoxy estradiol, E7010, methoxy benzenesuflonamides, vinorelbine, vinflunine, vindesine, dolastatins, spongistatin, rhizoxin, tasidotin, halichondrins, hemiasterlins, cryptophycin 52, MMAE and eribulin mesylate.

In an alternative preferred embodiment, a therapeutic agent to be used in combination with a DNA-breaking ADC, such as an SN-38-antibody conjugate, is a PARP inhibitor, such as olaparib, talazoparib (BMN-673), rucaparib, veliparib, CEP 9722, MK 4827, BGB-290, ABT-888, AG014699, BSI-201, CEP-8983 or 3-aminobenzamide.

In another alternative, a therapeutic agent used in combination with an antibody or immunoconjugate is a Bruton kinase inhibitor, such as such as ibrutinib (PCI-32765), PCI-45292, CC-292 (AVL-292), ONO-4059, GDC-0834, LFM-A13 or RN486.

In yet another alternative, a therapeutic agent used in combination with an antibody or immunoconjugate is a PI3K inhibitor, such as idelalisib, Wortmannin, demethoxyviridin, perifosine, PX-866, IPI-145 (duvelisib), BAY 80-6946, BEZ235, RP6530, TGR1202, SF1126, INK1117, GDC-0941, BKM120, XL147, XL765, Palomid 529, GSK1059615, ZSTK474, PWT33597, IC87114, TG100-115, CAL263, PI-103, GNE477, CUDC-907, AEZS-136 or LY294002.

Therapeutic agents that may be used in concert with the camptothecin conjugates also may comprise toxins conjugated to targeting moieties. Toxins that may be used in this regard include ricin, abrin, ribonuclease (RNase), DNase I, ranpirnase, Staphylococcal enterotoxin-A, pokeweed antiviral protein, gelonin, diphtheria toxin, *Pseudomonas* exotoxin, and *Pseudomonas* endotoxin. (See, e.g., Pastan. et al., *Cell* (1986), 47:641, and Sharkey and Goldenberg, *CA Cancer J Clin*. 2006 July-August; 56(4):226-43.) Additional toxins suitable for use herein are known to those of skill in the art and are disclosed in U.S. Pat. No. 6,077,499.

Yet another class of therapeutic agent may comprise one or more immunomodulators. Immunomodulators of use may be selected from a cytokine, a stem cell growth factor, a lymphotoxin, a hematopoietic factor, a colony stimulating factor (CSF), an interferon (IFN), erythropoietin, thrombopoietin and a combination thereof. Specifically useful are lymphotoxins such as tumor necrosis factor (TNF), hematopoietic factors, such as interleukin (IL), colony stimulating factor, such as granulocyte-colony stimulating factor (G-CSF) or granulocyte macrophage-colony stimulating factor (GM-CSF), interferon, such as interferons-α, -β, -γ or -λ, and stem cell growth factor, such as that designated "S1 factor". Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; prostaglandin, fibroblast growth factor; prolactin; placental lactogen, OB protein; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, -γ and -λ; colony stimulating factors (CSFs) such as macrophage-CSF (M-CSF); interleukins (ILs) such as IL-1, IL-1α, IL-2, IL-3, IL-4, IL-5, IL-6, IL-7, IL-8, IL-9, IL-10, IL-11, IL-12; IL-13, IL-14, IL-15, IL-16, IL-17, IL-18, IL-21, IL-25, LIF, kit-ligand or FLT-3, angiostatin, thrombospondin, endostatin, tumor necrosis factor and lymphotoxin (LT). As used herein, the term cytokine includes proteins from natural sources or from recombinant cell culture and biologically active equivalents of the native sequence cytokines.

Chemokines of use include RANTES, MCAF, MIP1-alpha, MIP1-Beta and IP-10.

The person of ordinary skill will realize that the subject immunoconjugates, comprising a camptothecin conjugated to an antibody or antibody fragment, may be used alone or in combination with one or more other therapeutic agents, such as a second antibody, second antibody fragment, second immunoconjugate, radionuclide, toxin, drug, chemotherapeutic agent, radiation therapy, chemokine, cytokine, immunomodulator, enzyme, hormone, oligonucleotide, RNAi or siRNA. Such additional therapeutic agents may be administered separately, in combination with, or attached to the subject antibody-drug immunoconjugates.

Formulation and Administration

Suitable routes of administration of the conjugates include, without limitation, oral, parenteral, subcutaneous, rectal, transmucosal, intestinal administration, intramuscular, intramedullary, intrathecal, direct intraventricular, intravenous, intravitreal, intraperitoneal, intranasal, or intraocular injections. The preferred routes of administration are parenteral. Alternatively, one may administer the compound in a local rather than systemic manner, for example, via injection of the compound directly into a solid tumor.

Immunoconjugates can be formulated according to known methods to prepare pharmaceutically useful compositions, whereby the immunoconjugate is combined in a mixture with a pharmaceutically suitable excipient. Sterile phosphate-buffered saline is one example of a pharmaceutically suitable excipient. Other suitable excipients are well-known to those in the art. See, for example, Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

In a preferred embodiment, the immunoconjugate is formulated in Good's biological buffer (pH 6-7), using a buffer selected from the group consisting of N-(2-acetamido)-2-aminoethanesulfonic acid (ACES); N-(2-acetamido)iminodiacetic acid (ADA); N,N-bis(2-hydroxyethyl)-2-aminoethanesulfonic acid (BES); 4-(2-hydroxyethyl)piperazine-1-ethanesulfonic acid (HEPES); 2-(N-morpholino)ethanesulfonic acid (MES); 3-(N-morpholino)propanesulfonic acid (MOPS); 3-(N-morpholinyl)-2-hydroxypropanesulfonic acid (MOPSO); and piperazine-N,N'-bis(2-ethanesulfonic acid) [Pipes]. More preferred buffers are MES or MOPS, preferably in the concentration range of 20 to 100 mM, more preferably about 25 mM. Most preferred is 25 mM MES, pH 6.5. The formulation may further comprise 25 mM trehalose and 0.01% v/v polysorbate 80 as excipients, with the final buffer concentration modified to 22.25 mM as a result of added excipients. The preferred method of storage is as a lyophilized formulation of the conjugates, stored in the temperature range of −20° C. to 2° C., with the most preferred storage at 2° C. to 8° C.

The immunoconjugate can be formulated for intravenous administration via, for example, bolus injection, slow infusion or continuous infusion. Preferably, the antibody of the present invention is infused over a period of less than about 4 hours, and more preferably, over a period of less than about 3 hours. For example, the first 25-50 mg could be infused within 30 minutes, preferably even 15 min, and the remainder infused over the next 2-3 hrs. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

Additional pharmaceutical methods may be employed to control the duration of action of the therapeutic conjugate. Control release preparations can be prepared through the use of polymers to complex or adsorb the immunoconjugate. For example, biocompatible polymers include matrices of poly (ethylene-co-vinyl acetate) and matrices of a polyanhydride copolymer of a stearic acid dimer and sebacic acid. Sherwood et al., *Bio/Technology* 10: 1446 (1992). The rate of release of an immunoconjugate from such a matrix depends upon the molecular weight of the immunoconjugate, the amount of immunoconjugate within the matrix, and the size of dispersed particles. Saltzman et al., *Biophys.* 1 55: 163 (1989); Sherwood et al., supra. Other solid dosage forms are described in Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

Generally, the dosage of an administered immunoconjugate for humans will vary depending upon such factors as the patient's age, weight, height, sex, general medical condition and previous medical history. It may be desirable to provide the recipient with a dosage of immunoconjugate that is in the range of from about 1 mg/kg to 24 mg/kg as a single intravenous infusion, although a lower or higher dosage also may be administered as circumstances dictate. A dosage of 1-20 mg/kg for a 70 kg patient, for example, is 70-1,400 mg, or 41-824 mg/m$^2$ for a 1.7-m patient. The dosage may be repeated as needed, for example, once per week for 4-10 weeks, once per week for 8 weeks, or once per week for 4 weeks. It may also be given less frequently, such as every other week for several months, or monthly or quarterly for many months, as needed in a maintenance therapy. Preferred dosages may include, but are not limited to, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 22 mg/kg and 24 mg/kg. Any amount in the range of 1 to 24 mg/kg may be used. The dosage is preferably administered multiple times, once or twice a week. A minimum dosage schedule of 4 weeks, more preferably 8 weeks, more preferably 16 weeks or longer may be used. The schedule of administration may comprise administration once or twice a week, on a cycle selected from the group consisting of: (i) weekly; (ii) every other week; (iii) one week of therapy followed by two, three or four weeks off; (iv) two weeks of therapy followed by one, two, three or four weeks off; (v) three weeks of therapy followed by one, two, three, four or five week off; (vi) four weeks of therapy followed by one, two, three, four or five week off; (vii) five weeks of therapy followed by one, two, three, four or five week off; and (viii) monthly. The cycle may be repeated 4, 6, 8, 10, 12, 16 or 20 times or more.

Alternatively, an immunoconjugate may be administered as one dosage every 2 or 3 weeks, repeated for a total of at least 3 dosages. Or, twice per week for 4-6 weeks. If the dosage is lowered to approximately 200-300 mg/m$^2$ (340 mg per dosage for a 1.7-m patient, or 4.9 mg/kg for a 70 kg patient), it may be administered once or even twice weekly for 4 to 10 weeks. Alternatively, the dosage schedule may be decreased, namely every 2 or 3 weeks for 2-3 months. It has been determined, however, that even higher doses, such as 12 mg/kg once weekly or once every 2-3 weeks can be administered by slow i.v. infusion, for repeated dosing cycles. The dosing schedule can optionally be repeated at other intervals and dosage may be given through various parenteral routes, with appropriate adjustment of the dose and schedule.

In preferred embodiments, the immunoconjugates are of use for therapy of cancer. Examples of cancers include, but are not limited to, carcinoma, lymphoma, glioblastoma, melanoma, sarcoma, and leukemia, myeloma, or lymphoid malignancies. More particular examples of such cancers are noted below and include: squamous cell cancer (e.g., epithelial squamous cell cancer), Ewing sarcoma, Wilms tumor, astrocytomas, lung cancer including small-cell lung cancer, non-small cell lung cancer, adenocarcinoma of the lung and squamous carcinoma of the lung, cancer of the peritoneum, gastric or stomach cancer including gastrointestinal cancer, pancreatic cancer, glioblastoma multiforme, cervical cancer, ovarian cancer, liver cancer, bladder cancer, hepatoma, hepatocellular carcinoma, neuroendocrine tumors, medullary thyroid cancer, differentiated thyroid carcinoma, breast cancer, ovarian cancer, colon cancer, rectal cancer, endometrial cancer or uterine carcinoma, salivary gland carcinoma, kidney or renal cancer, prostate cancer, vulvar cancer, anal carcinoma, penile carcinoma, as well as head-and-neck cancer. The term "cancer" includes primary malignant cells or tumors (e.g., those whose cells have not migrated to sites in the subject's body other than the site of the original malignancy or tumor) and secondary malignant cells or tumors (e.g., those arising from metastasis, the migration of malignant cells or tumor cells to secondary sites that are different from the site of the original tumor).

Other examples of cancers or malignancies include, but are not limited to: Acute Childhood Lymphoblastic Leukemia, Acute Lymphoblastic Leukemia, Acute Lymphocytic Leukemia, Acute Myeloid Leukemia, Adrenocortical Carcinoma, Adult (Primary) Hepatocellular Cancer, Adult (Primary) Liver Cancer, Adult Acute Lymphocytic Leukemia, Adult Acute Myeloid Leukemia, Adult Hodgkin's Lymphoma, Adult Lymphocytic Leukemia, Adult Non-Hodgkin's Lymphoma, Adult Primary Liver Cancer, Adult Soft Tissue Sarcoma, AIDS-Related Lymphoma, AIDS-Related Malignancies, Anal Cancer, Astrocytoma, Bile Duct Cancer, Bladder Cancer, Bone Cancer, Brain Stem Glioma, Brain Tumors, Breast Cancer, Cancer of the Renal Pelvis and Ureter, Central Nervous System (Primary) Lymphoma, Central Nervous System Lymphoma, Cerebellar Astrocytoma, Cerebral Astrocytoma, Cervical Cancer, Childhood (Primary) Hepatocellular Cancer, Childhood (Primary) Liver Cancer, Childhood Acute Lymphoblastic Leukemia, Childhood Acute Myeloid Leukemia, Childhood Brain Stem Glioma, Childhood Cerebellar Astrocytoma, Childhood Cerebral Astrocytoma, Childhood Extracranial Germ Cell Tumors, Childhood Hodgkin's Disease, Childhood Hodgkin's Lymphoma, Childhood Hypothalamic and Visual Pathway Glioma, Childhood Lymphoblastic Leukemia, Childhood Medulloblastoma, Childhood Non-Hodgkin's Lymphoma, Childhood Pineal and Supratentorial Primitive Neuroectodermal Tumors, Childhood Primary Liver Cancer, Childhood Rhabdomyosarcoma, Childhood Soft Tissue Sarcoma, Childhood Visual Pathway and Hypothalamic Glioma, Chronic Lymphocytic Leukemia, Chronic Myelogenous Leukemia, Colon Cancer, Cutaneous T-Cell Lymphoma, Endocrine Pancreas Islet Cell Carcinoma, Endometrial Cancer, Ependymoma, Epithelial Cancer, Esophageal Cancer, Ewing's Sarcoma and Related Tumors, Exocrine Pancreatic Cancer, Extracranial Germ Cell Tumor, Extragonadal Germ Cell Tumor, Extrahepatic Bile Duct Cancer, Eye Cancer, Female Breast Cancer, Gaucher's Disease, Gallbladder Cancer, Gastric Cancer, Gastrointestinal Carcinoid Tumor, Gastrointestinal Tumors, Germ Cell Tumors, Gestational Trophoblastic Tumor, Hairy Cell Leukemia, Head and Neck Cancer, Hepatocellular Cancer, Hodgkin's Lymphoma, Hypergammaglobulinemia, Hypopharyngeal Cancer, Intestinal Cancers, Intraocular Melanoma, Islet Cell Carcinoma, Islet Cell Pancreatic Cancer, Kaposi's Sarcoma, Kidney Cancer, Laryngeal Cancer, Lip and Oral Cavity Cancer, Liver Cancer, Lung Cancer, Lymphoproliferative Disorders, Macroglobulinemia, Male Breast Cancer, Malignant Mesothelioma, Malignant Thymoma, Medulloblastoma, Melanoma, Mesothelioma, Metastatic Occult Primary Squamous Neck Cancer, Metastatic Primary Squamous Neck Cancer, Metastatic Squamous Neck Cancer, Multiple Myeloma, Multiple Myeloma/Plasma Cell Neoplasm, Myelodysplastic Syndrome, Myelogenous Leukemia, Myeloid Leukemia, Myeloproliferative Disorders, Nasal Cavity and Paranasal Sinus Cancer, Nasopharyngeal Cancer, Neuroblastoma, Non-Hodgkin's Lymphoma, Nonmelanoma Skin Cancer, Non-Small Cell Lung Cancer, Occult Primary Metastatic Squamous Neck Cancer, Oropharyngeal Cancer, Osteo-/Malignant Fibrous Sarcoma, Osteosarcoma/Malignant Fibrous Histiocytoma, Osteosarcoma/Malignant Fibrous Histiocytoma of Bone, Ovarian Epithelial Cancer, Ovarian Germ Cell Tumor, Ovarian Low Malignant Potential Tumor, Pancreatic Cancer, Paraproteinemias, Polycythemia vera, Parathyroid Cancer, Penile Cancer, Pheochromocytoma, Pituitary Tumor, Primary Central Nervous System Lymphoma, Primary Liver Cancer, Prostate Cancer, Rectal Cancer, Renal Cell Cancer, Renal Pelvis and Ureter Cancer, Retinoblastoma, Rhabdomyosarcoma, Salivary Gland Cancer, Sarcoidosis Sarcomas, Sezary Syndrome, Skin Cancer, Small Cell Lung Cancer, Small Intestine Cancer, Soft Tissue Sarcoma, Squamous Neck Cancer, Stomach Cancer, Supratentorial Primitive Neuroectodermal and Pineal Tumors, T-Cell Lymphoma, Testicular Cancer, Thymoma, Thyroid Cancer, Transitional Cell Cancer of the Renal Pelvis and Ureter, Transitional Renal Pelvis and Ureter Cancer, Trophoblastic Tumors, Ureter and Renal Pelvis Cell Cancer, Urethral Cancer, Uterine Cancer, Uterine Sarcoma, Vaginal Cancer, Visual Pathway and Hypothalamic Glioma, Vulvar Cancer, Waldenstrom's macroglobulinemia, Wilms' tumor, and any other hyperproliferative disease, besides neoplasia, located in an organ system listed above.

The methods and compositions described and claimed herein may be used to treat malignant or premalignant conditions and to prevent progression to a neoplastic or malignant state, including but not limited to those disorders described above. Such uses are indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, Basic Pathology, 2d Ed., W. B. Saunders Co., Philadelphia, pp. 68-79 (1976)).

Dysplasia is frequently a forerunner of cancer, and is found mainly in the epithelia. It is the most disorderly form of non-neoplastic cell growth, involving a loss in individual cell uniformity and in the architectural orientation of cells. Dysplasia characteristically occurs where there exists chronic irritation or inflammation. Dysplastic disorders which can be treated include, but are not limited to, anhidrotic ectodermal dysplasia, anterofacial dysplasia, asphyxiating thoracic dysplasia, atriodigital dysplasia, bronchopulmonary dysplasia, cerebral dysplasia, cervical dysplasia, chondroectodermal dysplasia, cleidocranial dysplasia, congenital ectodermal dysplasia, craniodiaphysial dysplasia, craniocarpotarsal dysplasia, craniometaphysial dysplasia, dentin dysplasia, diaphysial dysplasia, ectodermal dysplasia, enamel dysplasia, encephalo-ophthalmic dysplasia, dysplasia epiphysialis hemimelia, dysplasia epiphysialis multiplex, dysplasia epiphysialis punctata, epithelial dysplasia, faciodigitogenital dysplasia, familial fibrous dysplasia of jaws, familial white folded dysplasia, fibromuscular dysplasia, fibrous dysplasia of bone, florid osseous dysplasia, hereditary renal-retinal dysplasia, hidrotic ectodermal dysplasia, hypohidrotic ectodermal dysplasia, lymphopenic thymic dysplasia, mammary dysplasia, mandibulofacial dysplasia, metaphysial dysplasia, Mondini dysplasia, monostotic fibrous dysplasia, mucoepithelial dysplasia, multiple epiphysial dysplasia, oculoauriculovertebral dysplasia, oculodentodigital dysplasia, oculovertebral dysplasia, odontogenic dysplasia, opthalmomandibulomelic dysplasia, periapical cemental dysplasia, polyostotic fibrous dysplasia, pseudoachondroplastic spondyloepiphysial dysplasia, retinal dysplasia, septo-optic dysplasia, spondyloepiphysial dysplasia, and ventriculoradial dysplasia.

Additional pre-neoplastic disorders which can be treated include, but are not limited to, benign dysproliferative disorders (e.g., benign tumors, fibrocystic conditions, tissue hypertrophy, intestinal polyps or adenomas, and esophageal dysplasia), leukoplakia, keratoses, Bowen's disease, Farmer's Skin, solar cheilitis, and solar keratosis.

In preferred embodiments, the method of the invention is used to inhibit growth, progression, and/or metastasis of cancers, in particular those listed above.

Additional hyperproliferative diseases, disorders, and/or conditions include, but are not limited to, progression, and/or metastases of malignancies and related disorders such as leukemia (including acute leukemias; e.g., acute lymphocytic leukemia, acute myelocytic leukemia [including myeloblastic, promyelocytic, myelomonocytic, monocytic, and erythroleukemia]) and chronic leukemias (e.g., chronic myelocytic [granulocytic] leukemia and chronic lymphocytic leukemia), polycythemia vera, lymphomas (e.g., Hodgkin's disease and non-Hodgkin's disease), multiple myeloma, Waldenström's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, emangioblastoma, acoustic neuroma, oligodendroglioma, meningioma, melanoma, neuroblastoma, and retinoblastoma.

Autoimmune diseases that may be treated with immunoconjugates may include acute and chronic immune thrombocytopenias, dermatomyositis, Sydenham's chorea, myasthenia gravis, systemic lupus erythematosus, lupus nephritis, rheumatic fever, polyglandular syndromes, bullous pemphigoid, diabetes mellitus, Henoch-Schonlein purpura, poststreptococcal nephritis, erythema nodosum, Takayasu's arteritis, ANCA-associated vasculitides, Addison's disease, rheumatoid arthritis, multiple sclerosis, sarcoidosis, ulcerative colitis, erythema multiforme, IgA nephropathy, polyarteritis nodosa, ankylosing spondylitis, Goodpasture's syndrome, thromboangitis obliterans, Sjogren's syndrome, primary biliary cirrhosis, Hashimoto's thyroiditis, thyrotoxicosis, scleroderma, chronic active hepatitis, polymyositis/dermatomyositis, polychondritis, bullous pemphigoid, pemphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis, psoriasis or fibrosing alveolitis.

Kits

Various embodiments may concern kits containing components suitable for treating cancer in a patient. Exemplary kits may contain at least one drug-conjugated antibody as described herein. If the composition containing components for administration is not formulated for delivery via the alimentary canal, such as by oral delivery, a device capable of delivering the kit components through some other route may be included. One type of device, for applications such as parenteral delivery, is a syringe that is used to inject the composition into the body of a subject. Inhalation devices may also be used.

The kit components may be packaged together or separated into two or more containers. In some embodiments, the containers may be vials that contain sterile, lyophilized formulations of a composition that are suitable for reconstitution. A kit may also contain one or more buffers suitable for reconstitution and/or dilution of other reagents. Other containers that may be used include, but are not limited to, a pouch, tray, box, tube, or the like. Kit components may be packaged and maintained sterilely within the containers. Another component that can be included is instructions to a person using a kit for its use.

EXAMPLES

Various embodiments of the present invention are illustrated by the following examples, without limiting the scope thereof.

Example 1

Clinical Trial of Sacituzumab Govitecan (IMMU-132) for Metastatic Urothelial Cancer Patients with metastatic, platinum-resistant urothelial carcinoma (PRUC) have no FDA-approved therapies. The response rates to second-line chemotherapy have generally been <20%, with a median overall survival of <1 year. We report herein our experience with 6 heavily pretreated patients with advanced PRUC (ClinicalTrials identifier NCT01631552) with the novel antibody-drug conjugate, sacituzumab govitecan (IMMU-132). This antibody-drug conjugate comprises the active metabolite of irinotecan, SN-38, conjugated to an anti-Trop-2 antibody (hRS7).

Trop-2 is widely expressed in ≤83% of urothelial carcinomas. Of the 6 patients, 3 had a clinically significant response (progression-free survival, 6.7 to 8.2 months; overall survival, 7.5+ to 11.4+ months). Sacituzumab govitecan was well tolerated. Because of these results, a phase II trial has been initiated. The present report demonstrates the utility of anti-Trop-2 antibody-drug conjugates, such as sacituzumab govitecan, as a novel therapeutic strategy for the treatment of PRUC.

Introduction

Urothelial bladder carcinoma (UC) is the sixth most frequent form of cancer (e.g., Sharma et al., 2009, Am Fam Physician 80:717-23). Cisplatin-based combination chemotherapy is the only known treatment that has demonstrated a survival benefit for patients with advanced disease (Logothetis et al., 1990, J Clin Oncol 8:1050-55; Loehrer et al., 1992, J Clin Oncol 10:1066-73). However, only a small subset will attain long-term survival. For those participating in clinical trials, the median overall survival has been 15 months and the 5-year survival has been only 15% (von der Maase et al., 2005, J Clin Oncol 23:4602-8). After progression within 6 to 12 months of platinum-based chemotherapy (platinum-resistant urothelial carcinoma [PRUC]), whether delivered in the perioperative or advanced setting, survival has been only 4 to 9 months for subjects eligible for enrollment in clinical trials. No second-line chemotherapy agents have been approved in the United States, and only vinflunine is available in Europe (Bellmunt et al., 2009, J Clin Oncol 27:4454-61). Developing effective second-line therapies for advanced urothelial cancer represents an important unmet medical need (Faltas et al., 2015, Expert Opin Ther Targets 19:515-25).

Antibody-drug conjugates (ADCs) targeting cell-surface antigens represent an attractive therapeutic strategy for chemotherapy-refractory tumors, including PRUC (Cardillo et al., 2015, Bioconjug Chem 26:919-31). Sacituzumab govitecan (IMMU-132) is a second-generation ADC comprising a humanized anti-Trop-2 monoclonal antibody (hRS7) conjugated with the active metabolite of irinotecan, SN-38 (Goldenberg et al., 2015, Oncotarget 6:22496-5120). It has demonstrated acceptable toxicity and excellent therapeutic activity in several solid tumors, both preclinically and clinically (Cardillo et al., 2015, Bioconjug Chem 26:919-31; Starodub et al., 2015, Clin Cancer Res 21:3870-78), and is a rational choice for targeting UC. Trop-2 (TACSTD2) protein is known to be expressed in normal urothelium (Stepan et al., 2011, J Histochem Cytochem 59:701-10) and in ≤83% of urothelial carcinomas (Faltas et al., 2016, Clin Genitourin Cancer 14:e75-9). A phase II clinical trial with irinotecan in patients with PRUC demonstrated an overall response rate of only 5% (95% confidence interval, 1%-17%), including a complete response lasting 33 months and overall survival of 5.4 months (Beer et al., 2008, Clin Genitourin Cancer 6:36-9).\ Irinotecan has also been used in combination with other drugs (Chaudhary et al., 2014, Am J Clin Oncol 37:188-93).

As part of an extended trial evaluating sacituzumab govitecan (ClinicalTrials identifier, NCT01631552), we initially studied 6 patients with PRUC, 3 of whom achieved clinically significant responses. The present Example describes this clinical experience, which demonstrates that this ADC is an attractive candidate for treatment of PRUC.

Materials and Methods

The humanized RS7 (hRS7) anti-Trop-2 antibody was produced as described in U.S. Pat. No. 7,238,785, the Figures and Examples section of which are incorporated herein by reference. SN-38 attached to a CL2A linker was produced and conjugated to hRS7 (anti-Trop-2) according to U.S. Pat. No. 7,999,083 (Example 10 and 12 of which are incorporated herein by reference). The conjugation protocol resulted in a ratio of between about 6 to 8 SN-38 molecules attached per antibody molecule.

Patients were eligible for the clinical trial with IMMU-132 if they had advanced PRUC, an Eastern Cooperative Oncology Group performance status of 0 to 1, and intact organ function (Starodub et al., 2015, Clin Cancer Res 21:3870-78). All the patients provided informed consent. All experimental procedures were performed in accordance with approved guidelines. Sacituzumab govitecan was administered intravenously on days 1 and 8 of 21-day cycles that were repeated until dose-limiting toxicity or progression developed. Response was assessed using the Response Evaluation Criteria in Solid Tumors, version 1.1. When available, immunohistochemical staining of archival tumor biopsy specimens obtained from treated patients was performed as described previously (Starodub et al., 2015, Clin Cancer Res 21:3870-78).

Results

The median patient age was 72.5 years (range, 42-80 years). All patients had metastatic disease and had been previously treated with platinum-containing regimens and other lines of therapy (median number of previous therapies, 3; Table 2). Of the 6 patients, 5 were in the poor or intermediate-risk groups according to the prognostic model for patients with UC receiving salvage systemic therapy (Sonpavde et al., 2015, J Clin Oncol 33 (abstract 311). All 6 patients with PRUC were available for the response assessment. Two achieved a partial response, with the best responder having a 38% reduction in target lesions, including liver metastases (FIG. 1). One patient had stable disease, with a 28% reduction in target lesions, and 3 patients had progressive disease, including 1 patient who was considered to have progressive disease using the Response Evaluation Criteria in Solid Tumors, version 1.1, because of a new lesion, despite a 12% reduction in his target lesions with treatment (Table 2). For the 3 patients with a clinically significant response, the progression-free survival was 6.7 to 8.2 months and overall survival was 7.5+ to 11.4+ months.

Sacituzumab govitecan was generally well tolerated. Two patients experienced grade 3 toxicities (flank pain and bacteremia). No grade 4 nonhematologic toxicities were observed. Immunohistochemical analysis of archival PRUC tumor tissue from patients treated with sacituzumab govitecan showed significant cell surface expression of Trop-2 protein (FIG. 2).

TABLE 2

Baseline Characteristics and Clinical Outcomes

| Pt. No | Sex | Age (Years) | Primary UC Site | Metastatic Sites | Previous Treatment | Hb (g/dL) | LDH (IU/L) | Albumin (g/dL) | Sacituzumab Govitecan Dose (mg/kg) | Sacituzumab Govitecan Cycles (n) | Best Response (%) | PFS (mo) | OS (mo) |
|---|---|---|---|---|---|---|---|---|---|---|---|---|---|
| 1 | M | 42 | Bladder | Bone | Gemcitabine + carboplatin Gemcitabine + cisplatin Docetaxel | 13 | 134 | 3.8 | 12 | 4 | PD (−30) | 1.5 | 10.8 |
| 2 | M | 80 | Renal pelvis | Liver, lung, mediastinal lymph nodes | Gemcitabine + carboplatin | 12.7 | 210 | 4 | 10 | 6 | PD (−30) | 1.9 | 1.9+ |
| 3 | M | 71 | Bladder | Pelvic, para-aortic, RPLNs | Paclitaxel, ifosfamide, cisplatin Docetaxel | 11.1 | 218 | 3.9 | 8 | 4 | PD (−12) | 1.8 | 1.8+ |
| 4 | M | 66 | Renal pelvis | Lung, para-aortic lymph nodes, psoas muscle | Gemcitabine + cisplatin | 9.6 | 148 | 3.6 | 8 | 13 | SD (−28) | 6.7 | 11.4+ |
| 5 | M | 74 | Bladder | SCV, mediastinal, RPLNs | BCG Gemcitabine + cisplatin Investigational (DN24-02) | 13.5 | 156 | 4.4 | 11 | 12+ | PR (−33) | 7.5+ | 7.5+ |
| 6 | M | 75 | Ureter | Liver, lung, pelvic lymph nodes, peritoneum | Gemcitabine + cisplatin (adjuvant) Gemcitabine + carboplatin Docetaxel + icrucumab | 9.3 | 187 | 2.6 | 8 | 25 | PR (−38) | 8.2 | 10.5 |

Abbreviations: BCG = bacille Calmette-Guérin; Hb = hemoglobin; LDH = lactate dehydrogenase; M = male; OS = overall survival; PD = progressive disease; PFS = progression-free survival; PR = partial response; Pt. No. = patient number; RECIST 1.1 = Response Evaluation Criteria in Solid Tumors, version 1.1; RPLNs = retroperitoneal lymph nodes; SCV = supraclavicular; SD = stable disease; UC = urothelial carcinoma.

Discussion

Although the vinca alkaloid vinflunine is available in Europe because of results from a phase III trial comparing it with the best supportive care in the second-line setting, its efficacy was marginal, with no overall survival advantage (Bellmunt et al., 2009, J Clin Oncol 27:4454-61). The overall response rate for patients treated with second-line therapy, such as vinflunine or other agents, including the taxanes and pemetrexed, has usually been <20%, with a median overall survival of only 4 to 9 months (Bellmunt et al., 2009, J Clin Oncol 27:4454-61; Sweeney et al., 2006, J Clin Oncol 24:3451-57; Galsky et al., 2007, Invest New Drugs 25:265-70). A recently presented positive phase II randomized trial of docetaxel with or without ramucirumab or icrucumab demonstrated a response rate of 5% and a progression-free survival of 10.4 weeks in the docetaxel-alone control arm (Petrylak et al., 2012, J Clin Oncol 30 (Abstract TPS4675). A large institutional review of the frequently prescribed second-line agent, pemetrexed, showed an objective response rate of 5% (95% confidence interval, 1%-9%) and a median progression-free survival of 2.4 months (Bambury et al., 2015, Oncologist 20:50-15). Thus, at present, patients with PRUC have limited therapeutic options.

In this first group of patients with PRUC enrolled in a phase I/II trial, sacituzumab govitecan showed an early signal of significant clinical activity in this heavily pre-treated cohort. As previously observed in UC cell lines and patient-derived PRUC tumors, we detected high levels of Trop-2 protein expression in tumor biopsies from patients treated with sacituzumab govitecan (FIG. 2). Our sample size did not permit a correlation between the Trop-2 expression levels and clinical response. However, the activity observed in this small subset of patients with PRUC, with good overall tolerability, is consistent with preclinical results indicating that the ADC selectively delivers a significant proportion of the potent drug to the tumor cells rather than to normal cells (Sharkey et al., 2015, Clin Cancer Res 21:3870-78). The data presented above demonstrate the safety and efficacy of IMMU-132 for metastatic urothelial cancer.

Example 2

Further Studies on IMMU-132 in Metastatic Urothelial Cancer

Following Example 1, further studies were performed in patients with mUC pre-treated with platinum-containing chemotherapy. Such patients have limited therapeutic options, with checkpoint-inhibitor immunotherapy (IO) responses in a minority of patients. We provide further evidence of the safety and activity of sacituzumab govitecan (IMMU-132) as therapy for chemotherapy-pretreated mUC pts (ClinicalTrials.gov, NCT01631552).

Method

We enrolled 32 pts with mUC and ECOG PS 0-1 who failed ≥1 prior standard therapy (median=3; range, 1-5). IMMU-132 was administered at 8 or 10 mg/kg on days 1 and 8 every 21 days, continued until disease progression (PD) or unacceptable toxicity. Response-evaluable pts received ≥2 doses, and had ≥1 post-baseline response assessment.

Results

Twenty-five pts [median age 68 yrs (range: 50-91), 24 males] were assessable for safety and response; 23 had prior platinum-containing therapy; 46% had ≥2 prior therapies; 4 also had IO agents. Sites of metastases included liver (N=4; 16%), lungs (N=7; 28%), bone (N=4; 16%), and lymph nodes (N=16; 64%). Pts received a median of 7 cycles (range, 2-23) of IMMU-132. ORR was 36% (9/25) [1 complete (CR) and 8 partial responses (PR)]; 44% (11/25) had stable disease (SD). Further, pts with 1 line of prior chemotherapy had an ORR of 53.8% (7/13), and 16.7% for those with 2 to 5 prior therapy lines. Median PFS for all patients is 7.2 mos (95% CI, 4.9-10.7); median survival is not reached yet. Of the 4 pts with progression after prior IO, there were 1 PR and 2 SDs with IMMU-132. Duration of response for CR/PR pts is currently 5.1 mos (95% CI, 4.1-12.9) and 10/11 pts (5 with ≥20% tumor reduction) had stable disease >4 mos. Grade 4 neutropenia (16%) lasted <7 days, and non-hematological grade 3 AEs included fatigue (12%) and hypophosphatemia (8%). No treatment-related deaths were observed. Analysis of Trop-2 expression revealed 1+ to 3+ positive staining in 95% of 19 archival patient specimens.

Conclusion

With an ORR of 36% and a median PFS of 7.2 months in a heavily pretreated population, these interim results show the efficacy and tolerability of IMMU-132 as $2^{nd}$ line or later therapy for platinum- or IO-pretreated mUC pts.

Example 3

Clinical Trials with IMMU-132 Anti-Trop-2 ADC in a Variety of Trop-2+ Cancers

Summary

The present Example reports results from a phase I clinical trial and ongoing phase II extension with IMMU-132, an ADC of the internalizing, humanized, hRS7 anti-Trop-2 antibody conjugated by a pH-sensitive linker to SN-38 (mean drug-antibody ratio=7.6). Trop-2 is a type I transmembrane, calcium-transducing, protein expressed at high density (~1×10$^5$), frequency, and specificity by many human carcinomas, with limited normal tissue expression. Preclinical studies in nude mice bearing Capan-1 human pancreatic tumor xenografts have revealed IMMU-132 is capable of delivering as much as 120-fold more SN-38 to tumor than derived from a maximally tolerated irinotecan therapy.

The results shown were obtained during the course of an initial Phase I trial of 25 patients who had failed multiple prior therapies (some including topoisomerase-I/II inhibiting drugs), and an ongoing Phase II extension now reporting on 69 patients, including in colorectal (CRC), small-cell and non-small cell lung (SCLC, NSCLC, respectively), triple-negative breast (TNBC), pancreatic (PDC), esophageal, and other cancers.

As discussed in detail below, Trop-2 was not detected in serum, but was strongly expressed (≥2$^+$ immunohistochemical staining) in most archived tumors. In a 3+3 trial design, IMMU-132 was given on days 1 and 8 in repeated 21-day cycles, starting at 8 mg/kg/dose, then 12 and 18 mg/kg before dose-limiting neutropenia. To optimize cumulative treatment with minimal delays, phase II is focusing on 8 and 10 mg/kg (n=30 and 14, respectively). In 49 patients reporting related AE at this time, neutropenia ≥Grade 3 occurred in 28% (4% Grade 4). Most common non-hematological toxicities initially in these patients have been fatigue (55%; ≥G3=9%), nausea (53%; ≥G3=0%), diarrhea (47%; ≥G3=9%), alopecia (40%), and vomiting (32%; ≥G3=2%); alopecia also occurred frequently. Homozygous UGT1A1*28/*28 was found in 6 patients, 2 of whom had more severe hematological and GI toxicities.

In the Phase I and the expansion phase, there are now 48 patients (excluding PDC) who are assessable by RECIST/CT for best response. Seven (15%) of the patients had a partial response (PR), including patients with CRC (N=1), TNBC (N=2), SCLC (N=2), NSCLC (N=1), and esophageal cancers (N=1), and another 27 patients (56%) had stable disease (SD), for a total of 38 patients (79%) with disease response; 8 of 13 CT-assessable PDC patients (62%) had SD, with a median time to progression (TTP) of 12.7 wks compared to 8.0 weeks in their last prior therapy. The TTP for the remaining 48 patients was 12.6+ wks (range 6.0 to 51.4 wks). Plasma CEA and CA19-9 correlated with responses who had elevated titers of these antigens in their blood. No anti-hRS7 or anti-SN-38 antibodies were detected despite dosing over months.

The conjugate cleared from the serum within 3 days, consistent with in vivo animal studies where 50% of the SN-38 was released daily, with >95% of the SN-38 in the serum being bound to the IgG in a non-glucoronidated form, and at concentrations as much as 100-fold higher than SN-38 reported in patients given irinotecan. These results show that the hRS7-SN-38-containing ADC is therapeutically active in metastatic solid cancers, with manageable diarrhea and neutropenia.

Pharmacokinetics

Two ELISA methods were used to measure the clearance of the IgG (capture with anti-hRS7 idiotype antibody) and the intact conjugate (capture with anti-SN-38 IgG/probe with anti-hRS7 idiotype antibody). SN-38 was measured by HPLC. Total IMMU-132 fraction (intact conjugate) cleared more quickly than the IgG (not shown), reflecting known gradual release of SN-38 from the conjugate. HPLC determination of SN-38 (Unbound and TOTAL) showed >95% the SN-38 in the serum was bound to the IgG. Low concentrations of SN-38G suggest SN-38 bound to the IgG is protected from glucoronidation. Comparison of ELISA for conjugate and SN-38 HPLC revealed both overlap, suggesting the ELISA is a surrogate for monitoring SN-38 clearance.

A summary of the dosing regiment and patient pool is provided in Table 3.

TABLE 3

Clinical Trial Parameters

| | |
|---|---|
| Dosing regimen | Once weekly for 2 weeks administered every 21 days for up to 8 cycles. In the initial enrollment, the planned dose was delayed and reduced if ≥Grade 2 treatment-related toxicity; protocol was amended to dose delay and reduction only in the event of ≥Grade 3 toxicity. |
| Dose level cohorts | 8, 12, 18 mg/kg; later reduced to an intermediate dose level of 10 mg/kg. |
| Cohort size | Standard Phase I [3 + 3] design; expansion includes ~15 patients in select cancers. |
| DLT | Grade 4 ANC ≥ 7 d; ≥Grade 3 febrile neutropenia of any duration; G4 Plt ≥ 5 d; G4 Hgb; Grade 4 N/V/D any duration/GS N/V/D for >48 h; G3 infusion-related reactions; related ≥G3 non-hematological toxicity. |
| Maximum Acceptable Dose (MAD) | Maximum dose where ≥2/6 patients tolerate $1^{st}$ 21-d cycle w/o delay or reduction or ≥G3 toxicity. |
| Patients | Metastatic colorectal, pancreas, gastric, esophageal, lung (NSCLC, SCLC), triple-negative breast (TNBC), prostate, ovarian, renal, urinary bladder, head/neck, hepatocellular. Refractory/relapsed after standard treatment regimens for metastatic cancer. Prior irinotecan-containing therapy NOT required for enrollment. No bulky lesion >5 cm. Must be 4 weeks beyond any major surgery, and 2 weeks beyond radiation or chemotherapy regimen. Gilbert's disease or known CNS metastatic disease are excluded. |

Clinical Trial Status

A total of 69 patients (including 25 patients in Phase I) with diverse metastatic cancers having a median of 3 prior therapies were reported. Eight patients had clinical progression and withdrew before CT assessment. Thirteen CT-assessable pancreatic cancer patients were separately reported. The median TTP (time to progression) in PDC patients was 11.9 wks (range 2 to 21.4 wks) compared to median 8 wks TTP for the preceding last therapy.

Figure 3:
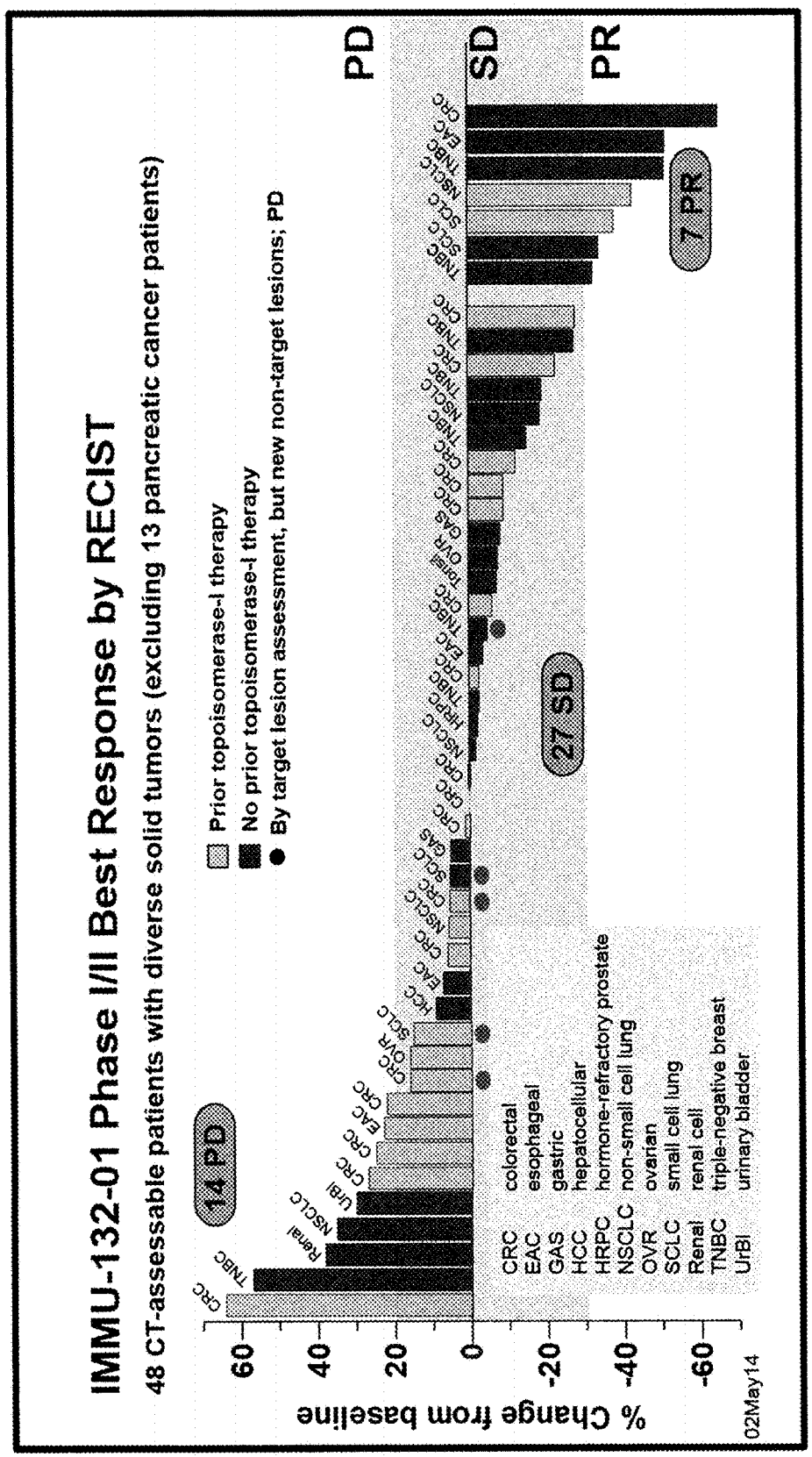
FIG. 3. IMMU-132 phase I/II data for best response by RECIST criteria.

A total of 48 patients with diverse cancers had at least 1 CT-assessment from which Best Response (FIG. 3) and Time to Progression (TTP; not shown) were determined. To summarize the Best Response data, of 8 assessable patients with TNBC (triple-negative breast cancer), there were 2 PR (partial response), 4 SD (stable disease) and 2 PD (progressive disease) for a total response [PR+SD] of 6/8 (75%). For SCLC (small cell lung cancer), of 4 assessable patients there were 2 PR, 0 SD and 2 PD for a total response of 2/4 (50%). For CRC (colorectal cancer), of 18 assessable patients there were 1 PR, 11 SD and 6 PD for a total response of 12/18 (67%). For esophageal cancer, of 4 assessable patients there were 1 PR, 2 SD and 1 PD for a total response of 3/4 (75%). For NSCLC (non-small cell lung cancer), of 5 assessable patients there were 1 PR, 3 SD and 1 PD for a total response of 4/5 (80%). Over all patients treated, of 48 assessable patients there were 7 PR, 27 SD and 14 PD for a total response of 34/48 (71%). These results demonstrate that the anti-TROP-2 ADC (hRS7-SN-38) showed significant clinical efficacy against a wide range of solid tumors in human patients.

The reported side effects of therapy (adverse events) are summarized in Table 4. As apparent from the data of Table 4, the therapeutic efficacy of hRS7-SN-38 was achieved at dosages of ADC showing an acceptably low level of adverse side effects.

TABLE 4

Related Adverse Events Listing for IMMU-132-01
Criteria: Total ≥10% or ≥Grade 3

| | N = 47 patients | | |
|---|---|---|---|
| | TOTAL | Grade 3 | Grade 4 |
| Fatigue | 55% | 4 (9%) | 0 |
| Nausea | 53% | 0 | 0 |
| Diarrhea | 47% | 4 (9%) | 0 |
| Neutropenia | 43% | 11 (24%) | 2 (4%) |
| Alopecia | 40% | — | — |
| Vomiting | 32% | 1 (2%) | 0 |
| Anemia | 13% | 2 (4%) | 0 |
| Dysgeusia | 15% | 0 | 0 |
| Pyrexia | 13% | 0 | 0 |
| Abdominal pain | 11% | 0 | 0 |
| Hypokalemia | 11% | 1 (2%) | 0 |
| WBC Decrease | 6% | 1 (2%) | 0 |
| Febrile Neutropenia | 6% | 1 (2%) | 2 (4%) |
| Deep vein thrombosis | 2% | 1 (2%) | 0 |

Grading by CTCAE v 4.0

The study reported in Table 4 has continued, with 261 patients enrolled to date. The results (not shown) have generally followed along the lines indicated in Table 4, with only neutropenia showing an incidence of Grade 3 or higher adverse events of over 10% of the patients tested. For all other adverse events, the incidence of Grade 3 or higher responses was less than 10%. This distinguishes the instant immunoconjugates from the great majority of ADCs and in certain embodiments, the claimed methods and compositions relate to anti-Trop-2 ADCs that show efficacy in diverse solid tumors, with an incidence of Grade 3 or higher adverse events of less than 10% of patients for all adverse events other than neutropenia. In a follow-up study, in a total of 421 samples from 121 patients with baseline and at least one follow-up sample available, no anti-hRS7 or anti-SN-38 antibody response has been detected, despite repeated cycles of treatment.

Exemplary partial responses to the anti-Trop-2 ADC were confirmed by CT data (not shown). As an exemplary PR in CRC, a 62 year-old woman first diagnosed with CRC underwent a primary hemicolectomy. Four months later, she had a hepatic resection for liver metastases and received 7 mos of treatment with FOLFOX and 1 mo SFU. She presented with multiple lesions primarily in the liver (3+ Trop-2 by immunohistology), entering the hRS7-SN-38 trial at a starting dose of 8 mg/kg about 1 year after initial diagnosis. On her first CT assessment, a PR was achieved, with a 37% reduction in target lesions (not shown). The patient continued treatment, achieving a maximum reduction of 65% decrease after 10 months of treatment (not shown) with decrease in CEA from 781 ng/mL to 26.5 ng/mL), before progressing 3 months later.

As an exemplary PR in NSCLC, a 65 year-old male was diagnosed with stage IIIB NSCLC (sq. cell). Initial treatment of caboplatin/etoposide (3 mo) in concert with 7000 cGy XRT resulted in a response lasting 10 mo. He was then started on Tarceva maintenance therapy, which he continued until he was considered for IMMU-132 trial, in addition to undergoing a lumbar laminectomy. He received first dose of IMMU-132 after 5 months of Tarceva, presenting at the time with a 5.6 cm lesion in the right lung with abundant pleural effusion. He had just completed his $6^{th}$ dose two months later when the first CT showed the primary target lesion reduced to 3.2 cm (not shown).

As an exemplary PR in SCLC, a 65 year-old woman was diagnosed with poorly differentiated SCLC. After receiving carboplatin/etoposide (Topoisomerase-II inhibitor) that ended after 2 months with no response, followed with topotecan (Topoisomerase-I inhibitor) that ended after 2 months, also with no response, she received local XRT (3000 cGy) that ended 1 month later. However, by the following month progression had continued. The patient started with IMMU-132 the next month (12 mg/kg; reduced to 6.8 mg/kg; Trop-2 expression 3+), and after two months of IMMU-132, a 38% reduction in target lesions, including a substantial reduction in the main lung lesion occurred (not shown). The patient progressed 3 months later after receiving 12 doses.

These results are significant in that they demonstrate that the anti-Trop-2 ADC was efficacious, even in patients who had failed or progressed after multiple previous therapies. In conclusion, at the dosages used, the primary toxicity was a manageable neutropenia, with few Grade 3 toxicities. IMMU-132 showed evidence of activity (PR and durable SD) in relapsed/refractory patients with triple-negative breast cancer, small cell lung cancer, non-small cell lung cancer, colorectal cancer and esophageal cancer, including patients with a previous history of relapsing on topoisomerase-I inhibitor therapy. These results show efficacy of the anti-Trop-2 ADC in a wide range of cancers that are resistant to existing therapies.

Example 4

Treatment of Patients with Advanced, Metastatic Pancreatic Cancer with Anti-Trop-2 ADC Summary Trop-2 is a type-I transmembrane, calcium-transducing protein expressed at high density, frequency, and specificity in many epithelial cancers, including pancreatic ductal adenocarcinoma, with limited normal tissue expression. All 29 pancreatic tumor microarray specimens tested were Trop-2-positive by immunohistochemistry, and human pancreatic cancer cell lines were found to express 115k-891k Trop-2 copies on the cell membrane.

We reported above the results from the IMMU-132 Phase I study enrolling patients with 13 different tumor types using a 3+3 design. The Phase I dose-limiting toxicity was neutropenia. Over 80% of 24 assessable patients in this study had long-term stable disease, with partial responses (RECIST) observed in patients with colorectal (CRC), triple-negative breast (TNBC), small-cell and non-small cell lung (SCLC, NSCLC), and esophageal (EAC) cancers. The present Example reports the results from the IMMU-132 Phase I/II study cohort of patients with metastatic PDC. Patients with PDC who failed a median of 2 prior therapies (range 1-5) were given IMMU-132 on days 1 and 8 in repeated 21-day cycles.

In the subgroup of PDC patients (N=15), 14 received prior gemcitabine-containing regimens. Initial toxicity data from 9 patients found neutropenia [3 of 9≥G3, 33%; and 1 case of G4 febrile neutropenia), which resulted in dose delays or dose reductions. Two patients had Grade 3 diarrhea; no patient had Grade 3-4 nausea or vomiting. Alopecia (Grades 1-2) occurred in 5 of 9 patients. Best response was assessable in 13 of 14 patients, with 8 stable disease for 8 to 21.4 wks (median 12.7 wks; 11.9 wks all 14 patients). One patient who is continuing treatment has not yet had their first CT assessment. Five had progressive disease by RECIST; 1 withdrew after just 1 dose due to clinical progression and was not assessable. Serum CA19-9 titers decreased in 3 of the patients with stable disease by 23 to 72%. Despite multiple administrations, none of the patients developed an antibody response to IMMU-132 or SN-38. Peak and trough serum samples showed that IMMU-132 cleared more quickly than the IgG, which is expected based on the known local release of SN-38 within the tumor cell. Concentrations of SN-38-bound to IgG in peak samples from one patient given 12 mg/kg of IMMU-132 showed levels of 4000 ng/mL, which is 40-times higher than the SN-38 titers reported in patients given irinotecan therapy.

We conclude that IMMU-132 is active (long-term stable disease) in 62% (8/13) of PDC patients who failed multiple prior therapies, with manageable neutropenia and little GI toxicity. Advanced PDC patients can be given repeated treatment cycles (>6) of 8-10 mg/kg IMMU-132 on days 1 and 8 of a 21-day cycle, with some dose adjustments or growth factor support for neutropenia in subsequent treatment cycles. These results agree with the findings in patients with advanced CRC, TNBC, SCLC, NSCLC, EAC who have shown partial responses and long-term stable disease with IMMU-132 administration. In summary, monotherapy IMMU-132 is a novel, efficacious treatment regimen for patients with PDC, including those with tumors that were previously resistant to other therapeutic regimens for PDC.

Methods and Results

Trop-2 expression—The expression of Trop-2 on the surface of various cancer cell lines was determined by flow cytometry using QUANTBRITE® PE beads. The results for number of Trop-2 molecules detected in the different cell lines was: BxPC-3 pancreatic cancer (891,000); NCI-N87 gastric cancer (383,000); MDA-MB-468 breast cancer (341,000); SK-MES-1 squamous cell lung cancer (27,000); Capan-1 pancreatic cancer (115,000); AGS gastric cancer (78,000) COLO 205 colon cancer (52,000). Trop-2 expression was also observed in 29 of 29 (100%) tissue microarrays of pancreatic adenocarcinoma (not shown).

SN-38 accumulation—SN-38 accumulation was determined in nude mice bearing Capan-1 human pancreatic cancer xenografts (~0.06-0.27 g). Mice were injected IV with irinotecan 40 mg/kg (773 µg; Total SN-38 equivalents=448 µg). This dose is MTD in mice. Human dose equivalent=3.25 mg/kg or ~126 mg/m². Or mice were injected IV with IMMU-132 1.0 mg (SN-38:antibody ratio=7.6; SN-38 equivalents=20 µg). This dose is well below the MTD in mice. Human equivalent dose ~4 mg/kg IMMU-132 (~80 µg/kg SN-38 equivalents). Necropsies were performed on 3 animals per interval, in irinotecan injected mice at 5 min, 1, 2, 6 and 24 hours or in IMMU-132 injected mice at 1, 6, 24, 48 and 72 h. Tissues were extracted and analyzed by reversed-phase HPLC analysis for SN-38, SN-38G, and irinotecan. Extracts from IMMU-132-treated animals also were acid hydrolyzed to release SN-38 from the conjugate (i.e., SN-38 (TOTAL]). The results (not shown) demonstrate that the IMMU-132 ADC has the potential to deliver 120 times more SN-38 to the tumor compared to irinotecan, even though 22-fold less SN-38 equivalents were administered with the ADC.

IMMU-132 clinical protocol—The protocol used in the phase I/II study was as indicated in Table 5 below.

TABLE 5

Clinical Protocol Using IMMU-132: OVERVIEW

| | |
|---|---|
| Dosing regimen | Once weekly for 2 weeks administered every 21 days for up to 8 cycles. Patients with objective responses are allowed to continue beyond 8 cycles. In the initial enrollment, the planned dose was delayed and reduced if ≥Grade 2 treatment-related toxicity; protocol was amended later in study to dose delay and reduction only in the event of ≥Grade 3 toxicity. The development of severe toxicities due to treatment requires dose reduction by 25% of the assigned dose for $1^{st}$ occurrence, 50% for $2^{nd}$ occurrence, and treatment discontinued entirely in the event of a $3^{rd}$ occurrence. |
| Dose level cohorts | 8, 12, 18 mg/kg; later reduced to an intermediate dose level of 10 mg/kg. |
| Cohort size | Standard Phase I [3 + 3] design; expansion includes 15 patients in select cancers. |
| DLT | Grade 4 ANC ≥ 7 d; ≥Grade 3 febrile neutropenia of any duration; Grade 4 Platelets ≥ 5 d; Grade 4 Hgb; Grade 4 N/V/D of any duration or any Grade 3 N/V/D for >48 h; Grade 3 infusion-related reactions; ≥Grade 3 non-heme toxicity at least possibly due to study drug. |
| Maximum Acceptable Dose (MAD) | Maximum dose where ≥2/6 patients tolerate the full 21-d treatment cycle without dose delay or reduction or ≥Grade 3 toxicity. |
| Patients | Metastatic colorectal, pancreas, gastric, esophageal, lung (NSCLC, SCLC), triple-negative breast, prostate, ovarian, renal, urinary bladder, head and neck, hepatocellular. Refractory/relapsed after standard treatment regimens for metastatic cancer. Prior irinotecan-containing therapy NOT required for enrollment. No bulky lesion >5 cm. Must be 4 weeks beyond any major surgery, and 2 weeks beyond radiation or chemotherapy regimen. Gilbert's disease or known CNS metastatic disease are excluded. |

Patients were administered IMMU-132 according to the protocol summarized above. An exemplary case study is as follows. A 34 y/o white male initially diagnosed with metastatic pancreatic cancer (liver) had progressed on multiple chemotherapy regimens, including gemcitabine/Erlotinib/FG-3019, FOLFIRINOX and GTX prior to introduction of IMMU-132 (8 mg/kg dose given days 1 and 8 of a 21 day cycle). The patient received the drug for 4 mo with good symptomatic tolerance, an improvement in pain, a 72% maximum decline in CA19-9 (from 15885 U/mL to 4418 U/mL) and stable disease by CT RECIST criteria along with evidence of tumor necrosis. Therapy had to be suspended due to a liver abscess; the patient expired ~6 weeks later, 6 mo following therapy initiation.

A study of 14 advanced PDC patients who relapsed after a median of 2 prior therapies showed CT-confirmed antitumor activity consisting of 8/13 (62%) with stable disease. Median duration of TTP for 13 CT assessable pts was 12.7 weeks compared to 8.0 weeks estimated from last prior therapy. This ADC, with a known drug of nanomolar toxicity, conjugated to an antibody targeting Trop-2 prevalent on many epithelial cancers, by a linker affording cleavage at the tumor site, represents a new efficacious strategy in pancreatic cancer therapy with ADCs. In comparison to the present standard of care for pancreatic cancer patients, the extension of time to progression in pancreatic cancer patients, particularly in those resistant to multiple prior therapies, was surprising and could not have been predicted.

Example 5

Further Results from Phase I/II Clinical Studies

Triple-Negative Breast Cancer (TNBC)

Figure 4:
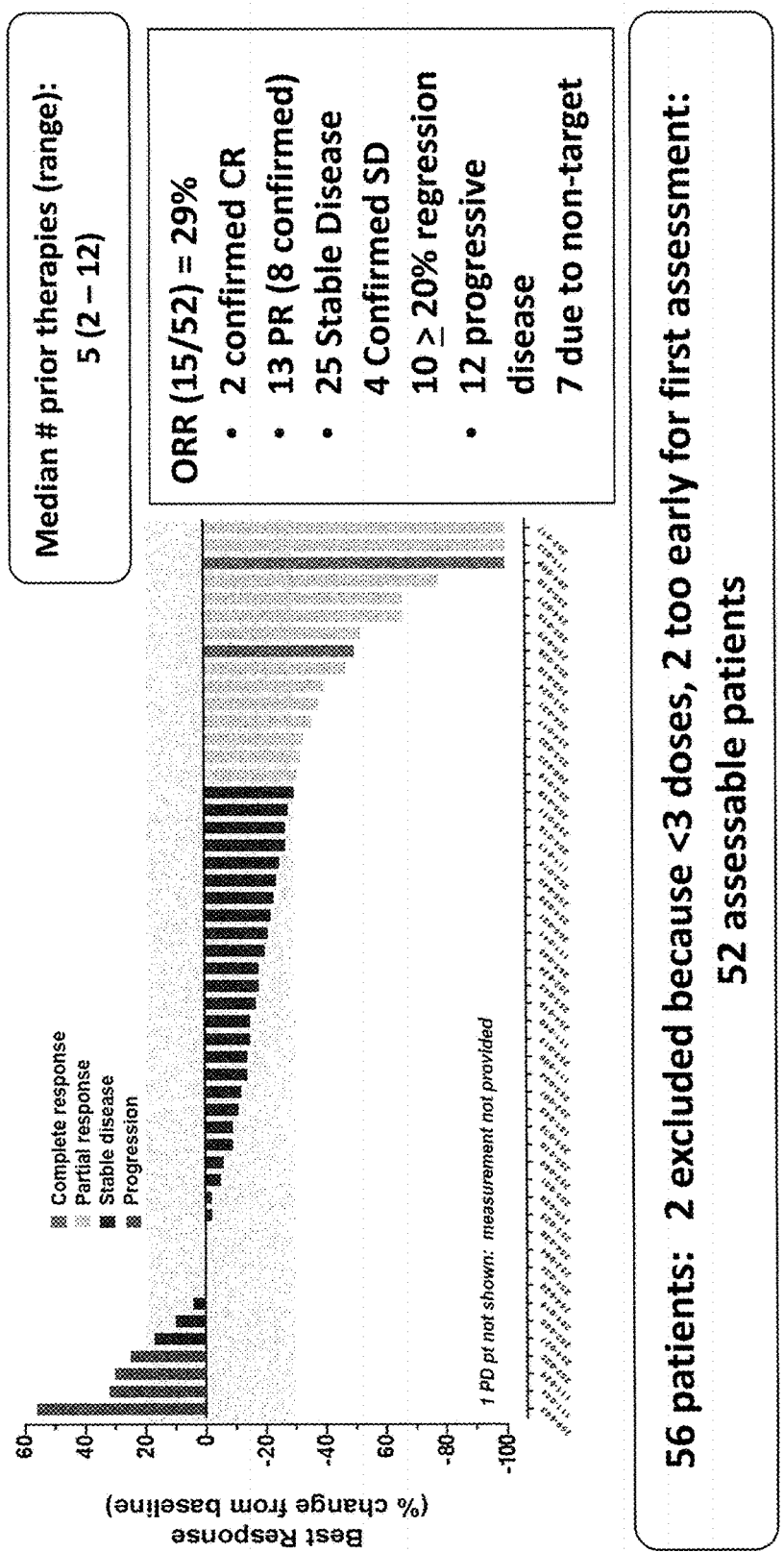
FIG. 4. Responses in 52 human TNBC patients treated with 10 mg/kg IMMU-132, after failing numerous prior therapies.
Figure 5:
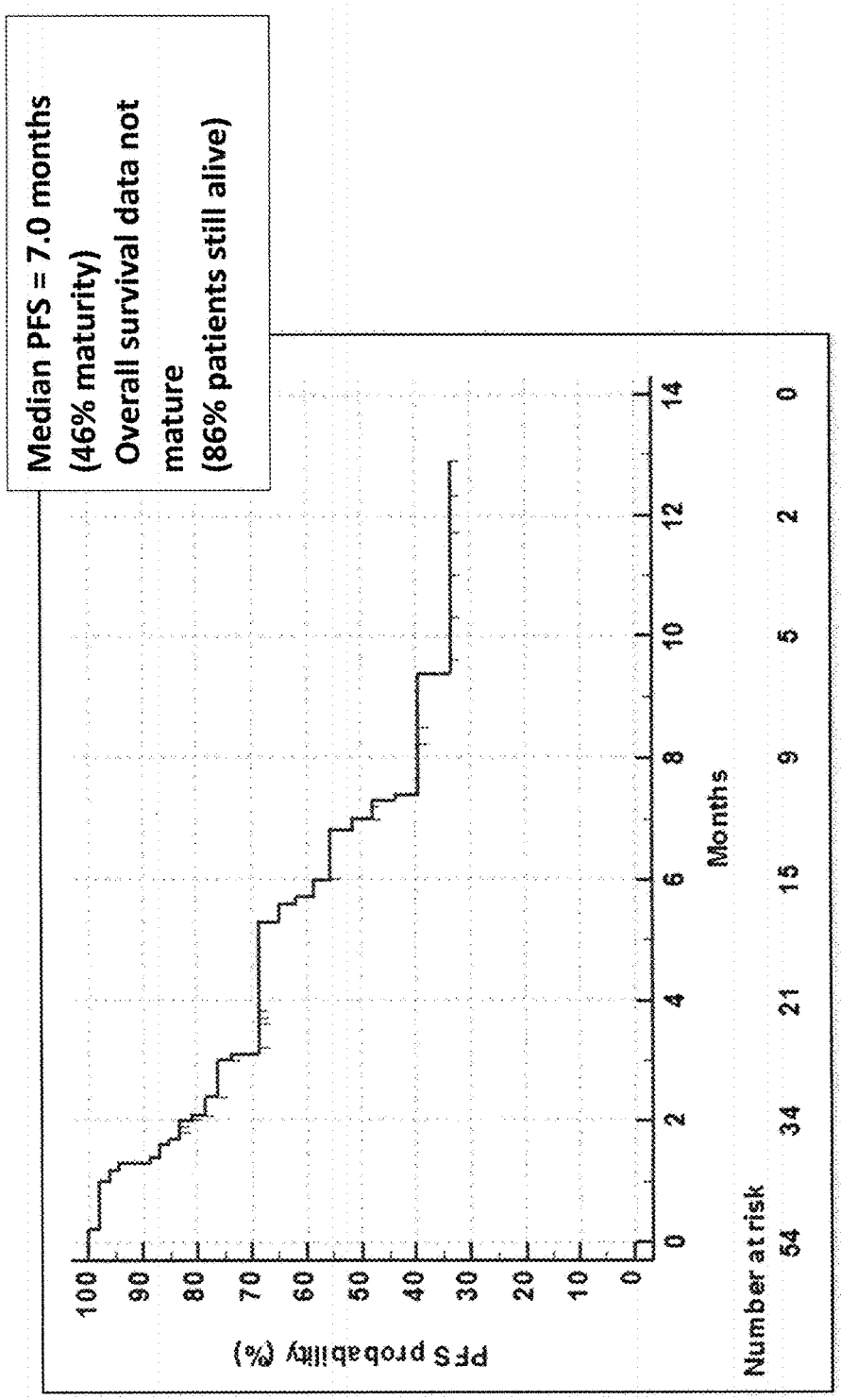
FIG. 5. Progression-free survival in TNBC patients treated with 10 mg/kg IMMU-132.

The phase I/II clinical trial (NCT01631552) discussed in the Examples above has continued, accruing 56 TNBC patients who were treated with 10 mg/kg. The patient population had previously been extensively treated before initiating IMMU-132 therapy, with at least 2 prior lines of therapy including taxane treatment. Previous treatments included cyclophosphamide, doxorubicin, carboplatin, gemcitabine, capecitabine, eribulin, cisplatinum, anastrozole, vinorelbine, bevacizumab and tamoxifen. Despite this extensive treatment history TNBC patients responded well to IMMU-132, with 2 confirmed complete responses (CR), 13 partial responses (PR) and 25 stable disease (SD), for an objective response rate of 29% (15/52) (FIG. 4). Adding the incidence of CR plus PR plus SD, treatment in TNBC resulted in a a 71% favorable response rate for IMMU-132 treated patients (not shown). The median time to progression in this heavily pretreated population of TNBC patients was 9.4 months, with a range of 2.9 to 14.2 months to date. However, 72% of patients in the study were still ongoing treatment. The progression-free survival in this group of patients is shown in FIG. 5.

Metastatic NSCLC

Figure 6:
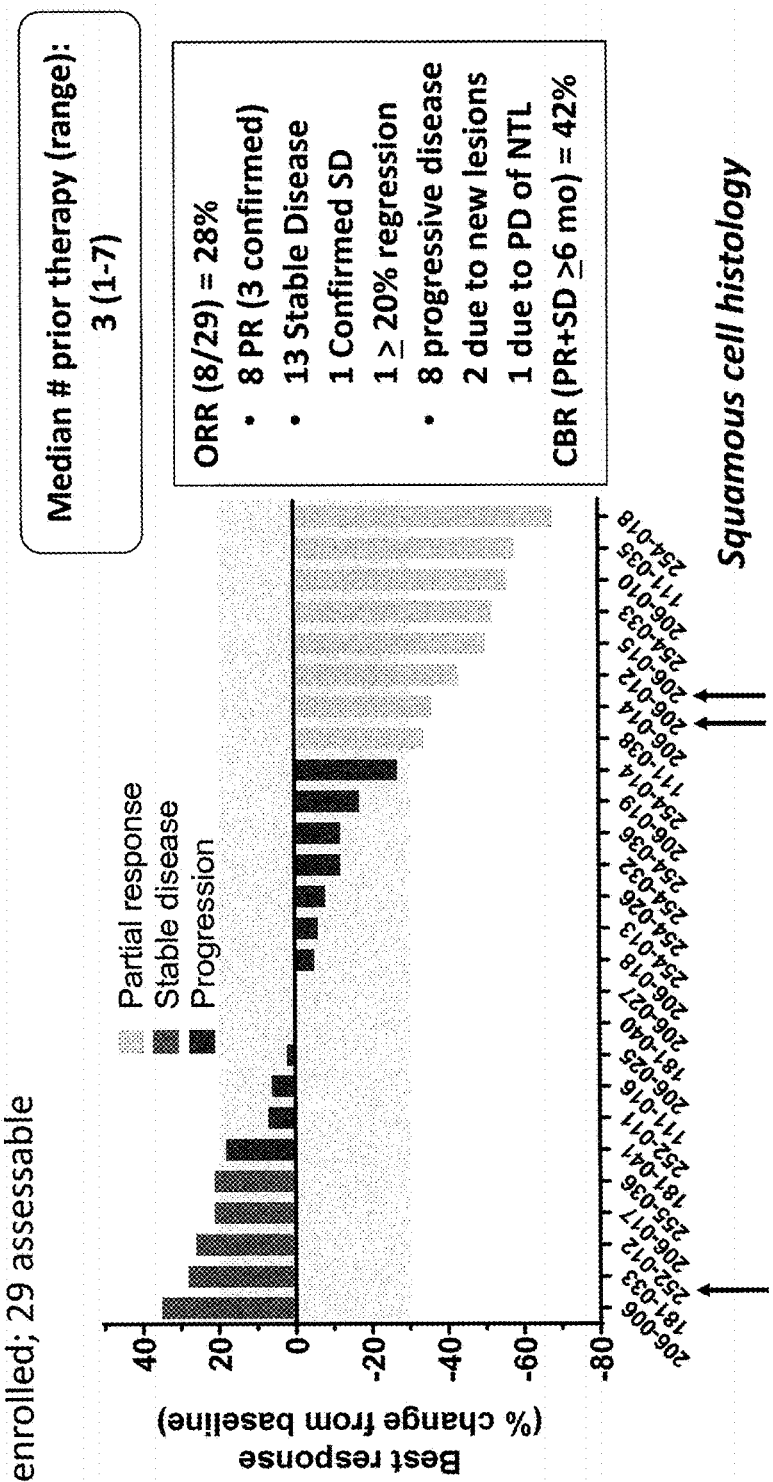
FIG. 6. Best response in 29 assessable human NSCLC patients treated with 8 to 10 mg/kg IMMU-132.
Figure 7:
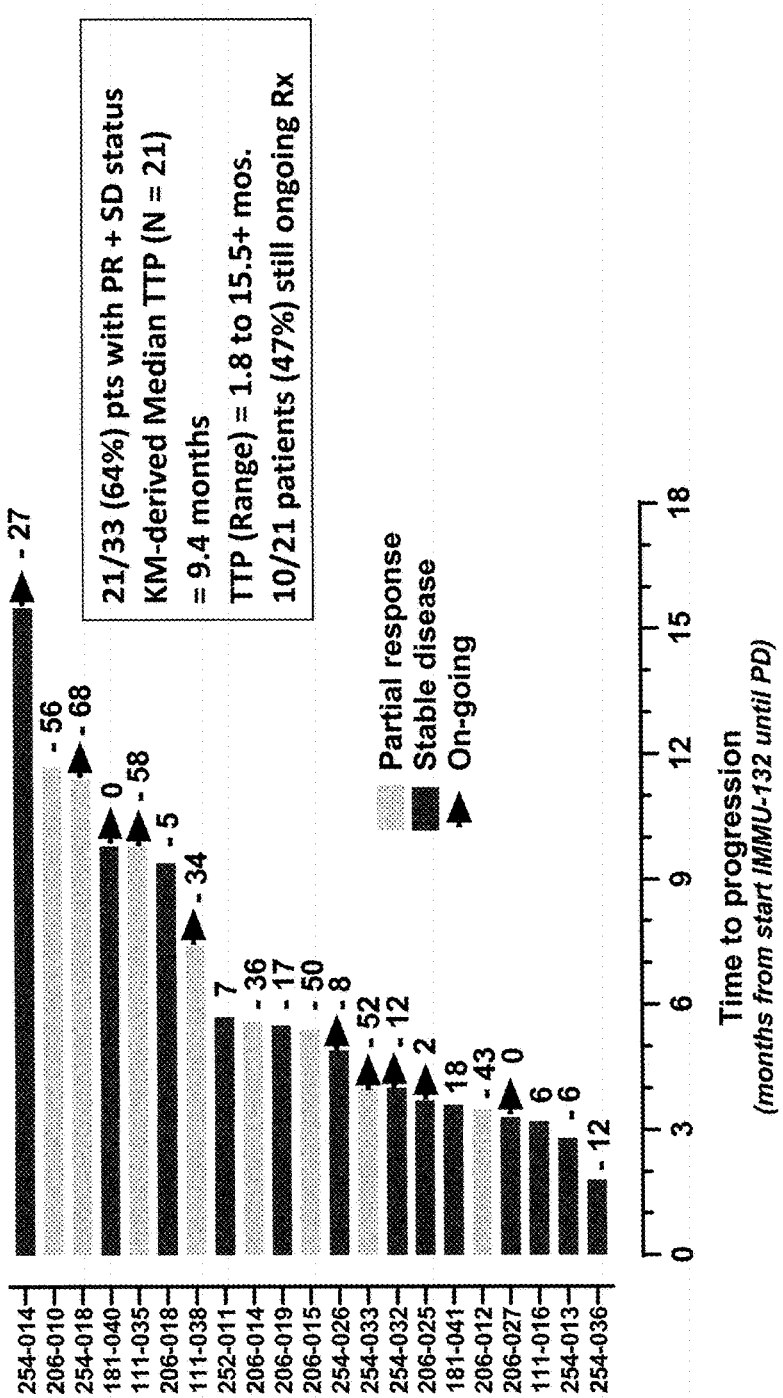
FIG. 7. Time to progression in NSCLC patients treated with 8-10 mg/kg IMMU-132.
Figure 8:
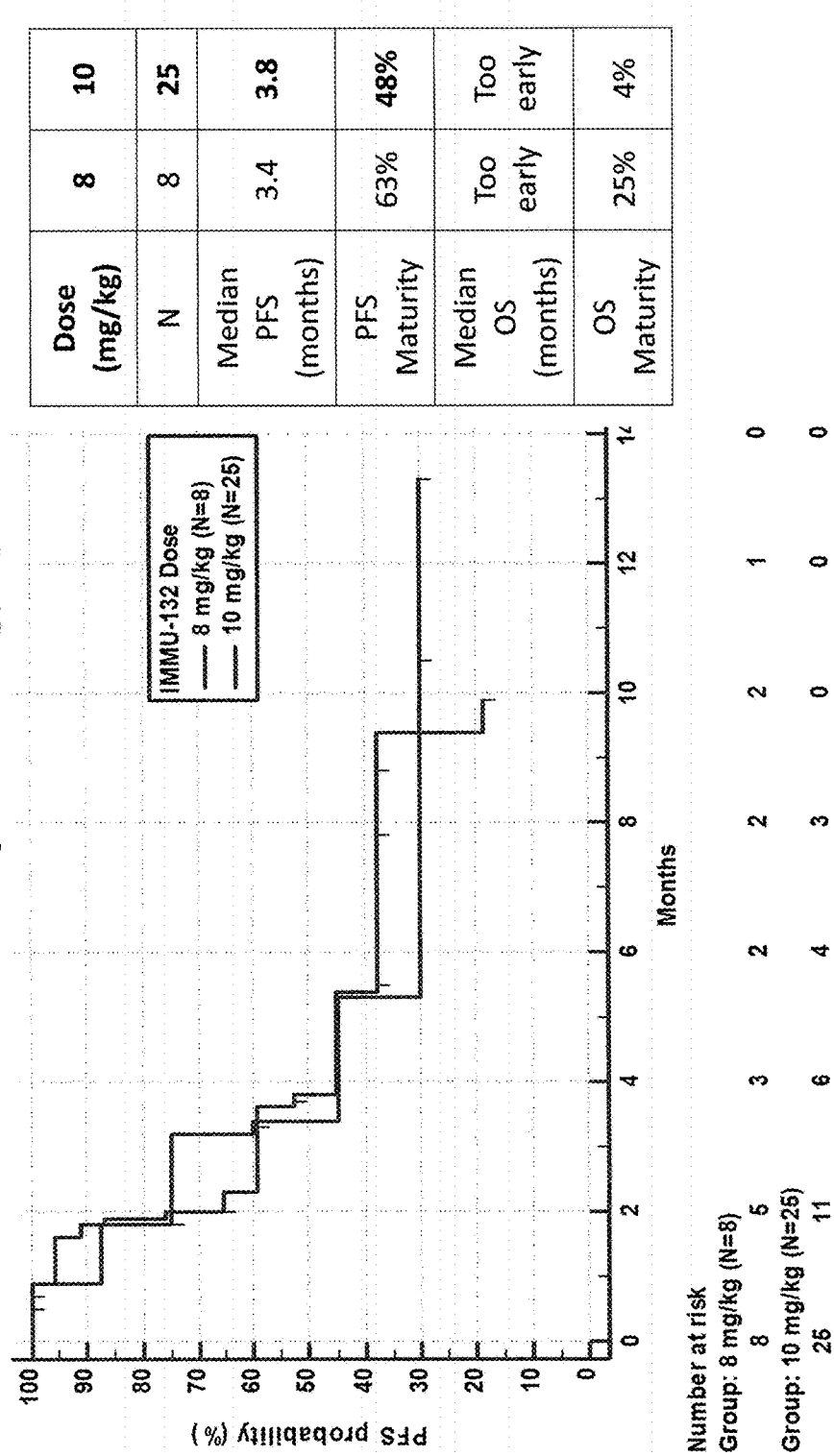
FIG. 8. Progression-free survival in NSCLC patients treated with 8 or 10 mg/kg IMMU-132.

The clinical trial is also ongoing for patients with metastatic non-small cell lung cancer (NSCLC), with 29 assessable patients accrued to date, who were treated with 8 or 10 mg/kg IMMU-132. The best responses by RESIST 1.1 criteria are shown in FIG. 6. Out of 29 patients, there were 8 PR and 13 SD. The time to progression for NSCLC patients is shown in FIG. 7, which shows that 21/33 (64%) of NSCLC patients exhibited PR or SD. The median time to progression was 9/4 months, with a range from 1.8 to 15.5+ months and 47% of patients still undergoing treatment. Progression-free survival in NSCLC patients treated with 8 or 10 mg/kg IMMU-132 is shown in FIG. 8. Median PFS was 3.4 months at 8 mg/kg and 3.8 months at 10 mg/kg.

However, studies are still ongoing and the median progression-free survival numbers are likely to improve.

Metastatic SCLC

Comparable results were obtained in metastatic SCLC patients. Best response by RECIST 1.1 for metastatic SCLC patients treated with 8 or 10 mg/kg IMMU-132 showed 6 PR and 8 SD out of 25 assessable patients (not shown). Time to progression showed a median of 4.9 months, with a range of 1.8 to 15.7+ months and 7 patients still undergoing treatment with IMMU-132 (not shown). The progression free survival showed a median PFS of 2.0 months at 8 mg/kg and 3.6 months at 10 mg/kg (not shown). The median OS was 8.1 months at 8 mg/kg and could not be determined yet for 10 mg/kg.

In summary, the continuing phase I/II clinical trial shows superior efficacy of IMMU-132, when administered at the recited dosages of ADC, in at least TNBC, NSCLC, SCLC and urothelial cancers. The superior therapeutic effect in these heavily pretreated and resistant metastatic cancers occurred without inducing severe toxicities that might preclude clinical use. IMMU-132 showed an acceptable safety profile in heavily pretreated patients with diverse solid cancers, and a median of 2-5 prior therapies. Only neutropenia showed an incidence of greater than 20% of the patient population for Grade 3 or higher adverse reactions. The study further demonstrates that repeated doses of IMMU-132 may be administered to human patients, at therapeutic dosages, without evoking interfering host anti-IMMU-132 antibodies. These results demonstrate the safety and utility of IMMU-132 for treating diverse Trop-2 positive cancers in human patients.

Example 6

Combination Therapy with ADC IMMU-132 and Microtubule Inhibitors or PARP Inhibitors Synthetic lethality is a concept in which a cell harboring one out of two possible gene or protein defects is viable, while a cell containing both defects is nonviable. BRCA1/2 mutations are linked to deficiencies in DNA repair and are associated with TNBC. Other repair mechanisms involve poly(adenosine diphosphoribose) polymerase (PARP), which can be used by cancer cells to overcome loss of BRACA1/2. Treatment of TNBC cells with either IMMU-132 or paclitaxel results in cleavage and deactivation of PARP, whereas the small molecule olaparib directly inhibits PARP. Therefore, the rationale of combining IMMU-132 with either paclitaxel or olaparib to effectively knock-out PARP activity was investigated in TNBC xenografts to ascertain if these combinations will result in synthetic lethality.

The purpose of this study was to determine whether combining an antibody-drug conjugate that induces DNA strand breaks, such as sacituzumab govitecan (also known as IMMU-132, an anti-Trop-2 hRS7-CL2A-SN-38), with microtubule inhibitors (e.g., paclitaxel or eribulin mesylate) or poly(adenosine diphosphoribose) polymerase (PARP) inhibitors (e.g., olaparib) in cancer (e.g., nude mice bearing TNBC xenografts) improves anti-tumor effects. The person of ordinary skill will realize that the unexpected superior effects of the combination of antibody-SN-38 conjugates with PARP or microtubule inhibitors are not limited to the specific exemplary antibody, drug, PARP inhibitor or microtubule inhibitor, but rather are characteristic of the classes of antibodies against tumor-associated antigens (TAAs), drugs that induce DNA strand breaks, PARP inhibitors and microtubule inhibitors.

Experimental Procedures

In a non-limiting example, mice bearing human TNBC (triple negative breast cancer) xenografts (MDA-MB-468 or HCC1806; ~0.3 cm$^3$) were treated with the maximum tolerated dose of paclitaxel (15 mg/kg weekly ×5 wks) and IMMU-132 at either 10 mg/kg or 12.5 mg/kg on days 1, 8, 22, and 29. Mice bearing HCC1806 tumors (~0.28 cm$^3$) were treated for 2 cycles with IMMU-132 (12.5 mg/kg) and 0.5 mg/kg of eribulin mesylate (equivalent to human dose of 1.4 mg/m$^2$) weekly for 2 weeks on a 21-day cycle. Studies examining PARP inhibition used mice bearing MDA-MB-468 tumors (~0.32 cm$^3$) treated with olaparib (50 mg/kg, qd×5 d, ×4 wks; 33% of human dose equaling 800 mg daily) and IMMU-132 (10 mg/kg, twice weekly ×4 wks). Olaparib was administered as i.p. injections daily for 5 days in a row with two day's rest before repeating (qd×5). This was done for four weeks. IMMU-132 was administered i.p. twice weekly for four weeks. Control animals received the non-tumor targeting anti-CD20 ADC hA20-CL2A-SN-38, either alone or in combination with olaparib. The primary endpoint was the median survival time (MST), defined as the time for tumors to progress to 1.0 cm$^3$.

In alternative embodiments, assay for synergistic effects may be determined by in vitro assay. A clonogenic assay may be used to determine survival fraction of cells (Ibrahim et al., 2012, Cancer Discovery 2:1036-47). Briefly, 350-800 cells are plated in 6-well flat bottom cell culture plates in duplicates. Twenty-four hours after plating, cells are washed and fresh medium is added in the presence or absence of increasing doses of ADC and/or PARP or microtubule inhibitor (e.g., olaparib) alone and in combination. Media containing the drug and/or is refreshed on day 4. Colonies are fixed and stained after 7 days of treatment with 1.5 ml of 6.0% glutaraldehyde and 0.5% crystal violet and colonies are counted by standard procedures. The surviving fraction (SF) of cells is calculated as follows:

$$SF = \frac{\text{Number of colonies formed after treatment}}{\text{Number of cells seeded} \times \text{Plating Efficiency}}$$

where $$\text{Plating Efficiency} = \frac{\text{Number of colonies formed in control}}{\text{Number of cells seeded}}$$

The interaction between ADC and PARP or microtubule inhibitor is assessed using the multiple drug effects analysis method of Chou and Talalay (1984, Adv Enzyme Regul 22:27-55). This method quantitatively describes the interaction between two or more drugs, with values less than 1 indicating synergistic interactions, values greater than 1 indicating antagonistic interactions, and values equal to 1 indicating additive interactions.

Results

Mice with MDA-MB-468 tumors given the combination of IMMU-132 and paclitaxel exhibited superior anti-tumor effects (not shown), with >11-fold tumor shrinkage, in comparison to 1.4-fold shrinkage in the IMMU-132 group alone (P=0.0003; area under the curve, AUC) or 11.4-fold increase in tumor size in mice treated with paclitaxel alone (P<0.0001; AUC).

In MDA-MB-468, the combination of 200 μg IMMU-132 plus paclitaxel has superior anti-tumor effects in terms of area under the curve (AUC) when compared to all the other groups (Table 6, P<0.0013). Lowering the amount of IMMU-132 administered with paclitaxel to 100 μg likewise results in significant anti-tumor effects as compared to mice treated with paclitaxel alone, IMMU-132 alone (100 μg), or untreated animals (Table 7, P<0.0328). No further comparisons between growth curves can be made with paclitaxel or untreated control groups since each began to lose mice due to disease progression (i.e., TV>1.0 cm$^3$) as of therapy day 49.

TABLE 6

Area under the curve comparisons between IMMU-132 (200 µg) plus Paclitaxel treated MDA-MB-468 tumor-bearing mice and all other treatment groups.

| Treatments | | Time of Comparison | Tumor Volumes (cm³) on that day (mean ± s.d.) | P-Value (AUC) |
|---|---|---|---|---|
| IMMU-132 (200 µg) plus Paclitaxel versus | IMMU-132 (200 µg) | Up to therapy Day 98 | 0.162 ± 0.144 vs. 0.621 ± 0.324 | 0.0003 |
| | IMMU-132 (100 µg) | Up to therapy Day 70 | 0.050 ± 0.062 vs. 0.634 ± 0.335 | 0.0002 |
| | Paclitaxel | Up to therapy Day 49 | 0.025 ± 0.041 vs. 0.705 ± 0.206 | <0.0001 |
| | IMMU-132 (100 µg) + Paclitaxel | Up to therapy Day 112 | 0.202 ± 0.191 vs. 0.496 ± 0.286 | 0.0013 |
| | Untreated | Up to therapy Day 49 | 0.025 ± 0.041 vs. 0.663 ± 0.349 | <0.0001 |

TABLE 7

Area under the curve comparisons between IMMU-132 (100 µg) plus Paclitaxel treated MDA-MB-468 tumor-bearing mice and all other treatment groups.

| Treatments | | Time of Comparison | Tumor Volumes (cm³) on that day (mean ± s.d.) | P-Value (AUC) |
|---|---|---|---|---|
| IMMU-132 (100 µg) plus Paclitaxel versus | IMMU-132 (200 µg) | Up to therapy Day 98 | 0.663 ± 0.349 vs. 0.621 ± 0.324 | 0.9539 |
| | IMMU-132 (100 µg) | Up to therapy Day 70 | 0.311 ± 0.196 vs. 0.634 ± 0.335 | 0.0328 |
| | Paclitaxel | Up to therapy Day 49 | 0.211 ± 0.155 vs. 0.705 ± 0.206 | <0.0001 |
| | Untreated | Up to therapy Day 49 | 0.211 ± 0.155 vs. 0.663 ± 0.349 | 0.0001 |

Figure 9A:
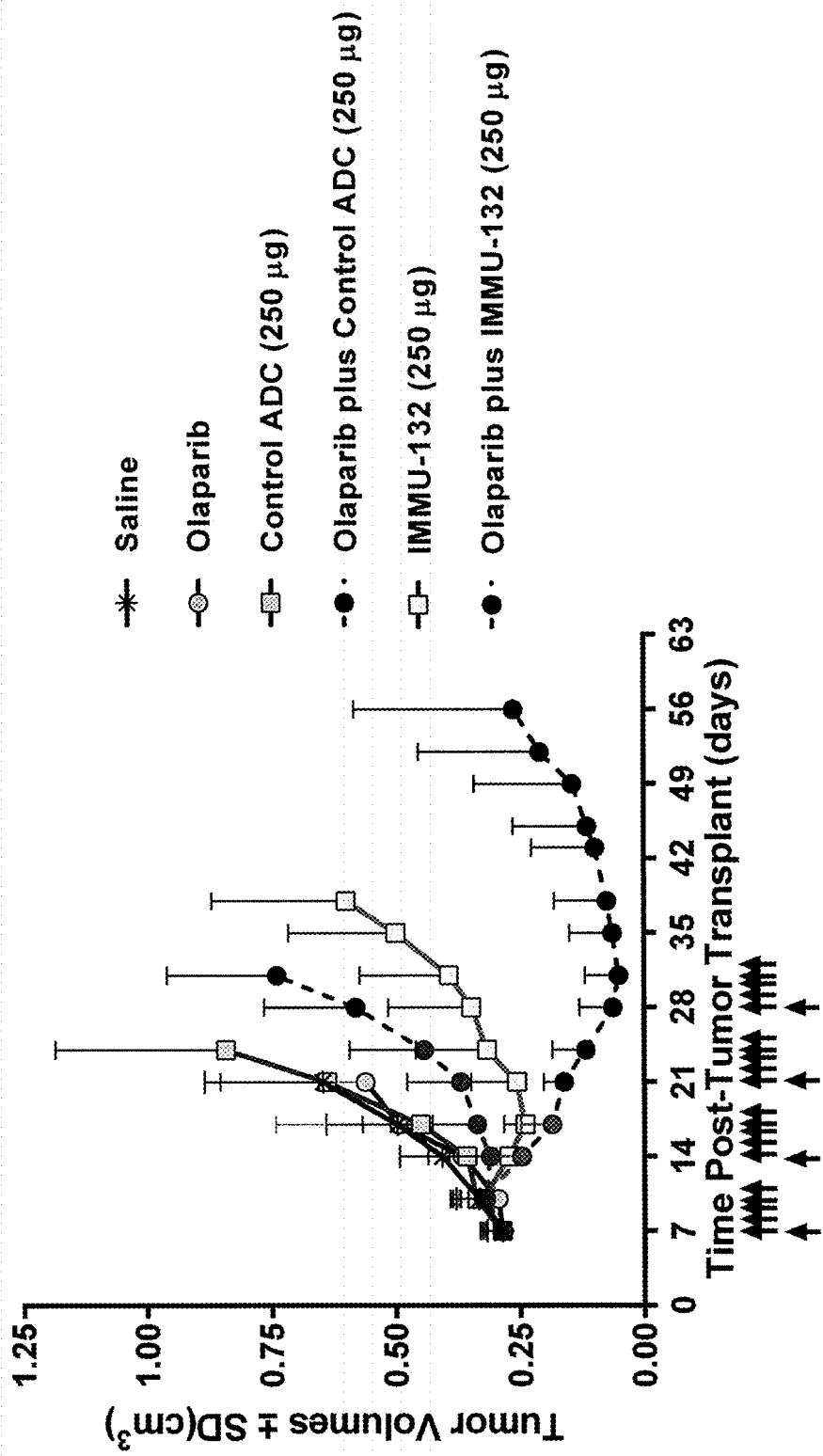
FIG. 9A. Tumor growth inhibition of combined IMMU-132 and Olaparib in TNBC: BRCA1/2 and PTEN defective tumors. Tumor-bearing mice (TV~0.3 cm$^3$) were treated with Olaparib (1 mg; ~50 mg/kg, i.p. on a M-F schedule; red arrows) or IMMU-132 (i.v. weekly, black arrows). A non-tumor-targeting anti-CD20 SN-38-ADC was used as a control. HCC1806 is a BRCA1/2-defective TNBC tumor line. Olaparib alone had no significant anti-tumor effects. IMMU-132 alone significantly inhibited tumor growth compared to all control groups (P<0.0106, AUC). IMMU-132 plus olaparib further improved anti-tumor responses significantly compared to all groups (P<0.0019; AUC). Mice in the combination group have yet to reach median survival (>80.5 days) which is more than 2- and 4-fold longer than IMMU-132 or olaparib monotherapy, respectively (P<0.0083).
Figure 9B:
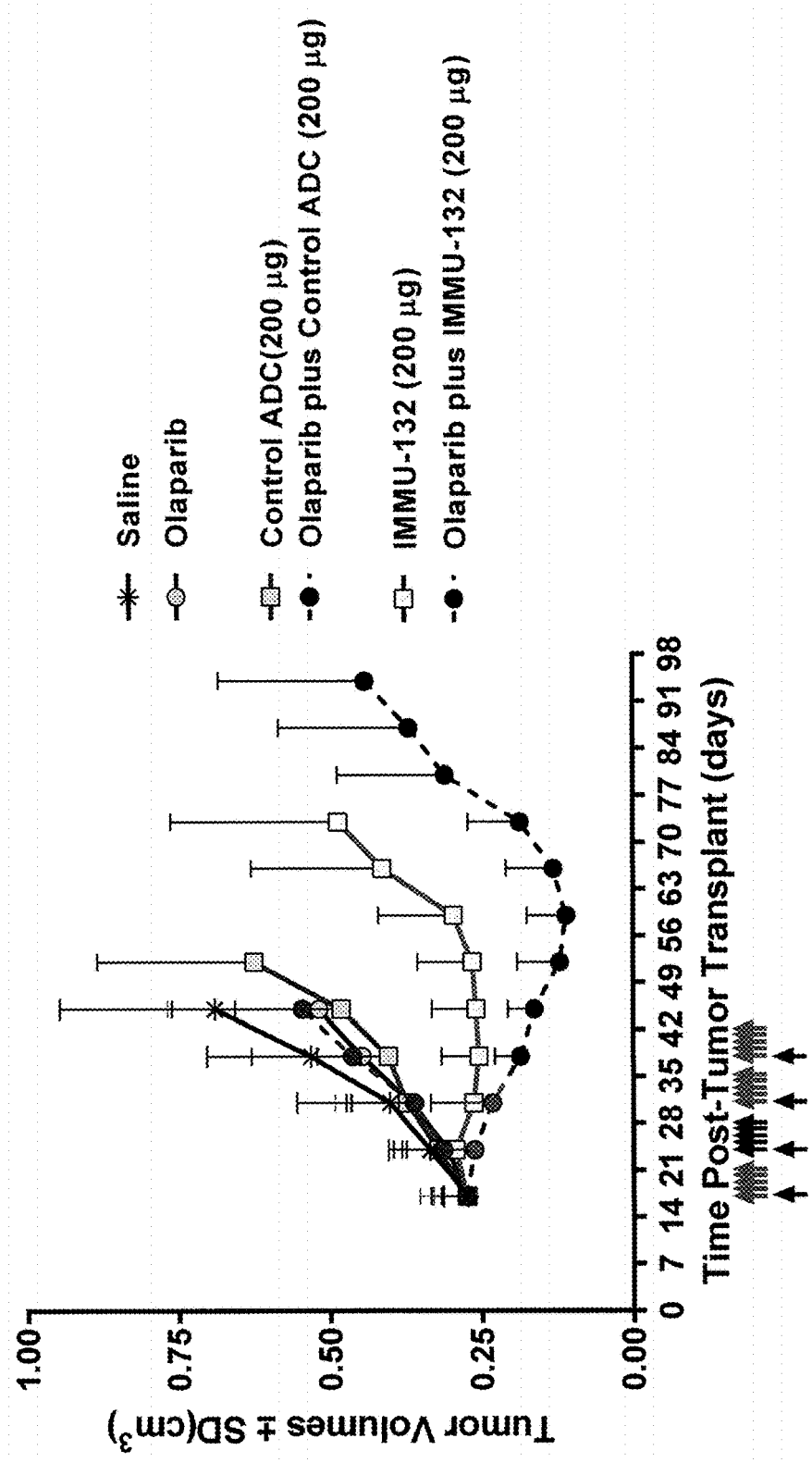
FIG. 9B. Tumor growth inhibition of combined IMMU-132 and Olaparib in TNBC: BRCA1/2 and PTEN defective tumors. Tumor-bearing mice (TV~0.3 cm$^3$) were treated with Olaparib (1 mg; ~50 mg/kg, i.p. on a M-F schedule; light arrows) or IMMU-132 (i.v. weekly, dark arrows). A non-tumor-targeting anti-CD20 SN-38-ADC was used as a control. In the BRCA1/2 w.t., PTEN-defective MDA-MB-468 tumors, IM IU-132 alone had significant anti-tumor effects compared to all control groups (P<0.0098; AUC). However, the combination of IMMU-132 plus olaparib inhibited tumor growth significantly better than either IMMU-132 or olaparib alone (P=0.004; AUC). This translates into a significant survival benefit when compared to all other groups (P<0.045).

In the rapidly-progressing HCC1806 xenografts (FIG. 9A-9B), the combination of IMMU-132 plus paclitaxel proved to have a superior anti-tumor effect when compared to IMMU-132 monotherapy (P=0.0195, $AUC_{17days}$). This is a very aggressive tumor with a median survival time (MST) of only 10 days post-therapy initiation for the untreated control animals (18 days post-tumor cell inoculation). In terms of survival, the combination, which reached its MST of 38 days, provided a significant survival benefit when compared to all other therapies (P<0.017; log-rank). It should be noted that this was achieved at a low dose of only 0.25 mg which would be the human equivalent dose of only 1 mg/kg.

Mice treated with the combination of IMMU-132 plus eribulin mesylate (not shown) exhibited a significantly greater anti-tumor response than all other monotherapy groups (P<0.0432; paired t-test). This resulted in a significant survival benefit for the combination (MST=23 days) when compared to eribulin or IMMU-132 monotherapy (MST=18 and 14 days, respectively; P<0.0044; log-rank).

Likewise, combining IMMU-132 therapy with olaparib was superior to single agent therapy in mice bearing MDA-MB-468 tumors (P<0.0032; AUC). Results are summarized in Table 8. All the IMMU-132 combination treatments were well-tolerated.

TABLE 8

Area under the curve comparisons between IMMU-132 plus Olaparib treated MDA-MB-468 tumor-bearing mice and all other treatment groups.

| Treatments | | Time of Comparison | Tumor Volumes (cm³) on that day (mean ± s.d.) | P-Value (AUC) |
|---|---|---|---|---|
| IMMU-132 plus Olaparib versus | IMMU-132 Alone | Up to therapy Day 49 | 0.030 ± 0.038 vs. 0.088 ± 0.069 | 0.0023 |
| | hA20-SN-38 plus Olaparib | Up to therapy Day 49 | 0.030 ± 0.038 vs. 0.652 ± 0.306 | <0.0001 |
| | hA20-SN-38 Alone | Up to therapy Day 42 | 0.045 ± 0.045 vs. 0.654 ± 0.285 | 0.0002 |
| | Olaparib Alone | Up to therapy Day 28 | 0.083 ± 0.050 vs. 0.649 ± 0.267 | <0.0001 |
| | Saline | Up to therapy Day 28 | 0.083 ± 0.050 vs. 0.697 ± 0.352 | <0.0001 |

Drug-antibody ratio (DAR) determination. Five clinical lots of IMMU-132 were evaluated by hydrophobic interaction HPLC (HIC-HPLC), which resolved three peaks representing species with DARs of 6, 7 and 8, with the greatest fraction comprising a DAR=8 (not shown). IMMU-132 was produced consistently by this manufacturing process, with an overall DAR ($DAR_{AVE}$) of 7.60±0.03 among the five clinical lots. HIC-HPLC results were confirmed by liquid chromatography-mass spectrometry (LC-MS). The analysis showed that >99% of the 8 available sulfhydryl groups were coupled with the CL2A linker, either with or without SN-38 (not shown). There were no unsubstituted (or N-ethylmaleimide capped) heavy or light chains detected. Thus, the difference in DAR among the species results from SN-38 liberation from the linker during manufacturing and not from a lower initial substitution ratio. Once prepared and lyophilized, IMMU-132 has been stable for several years.

Effect of DAR on pharmacokinetics and anti-tumor efficacy in mice. Mice bearing Trop-2$^+$ human gastric carcinoma xenografts (NCI-N87) were given 2 treatments 7 days apart, each with equal protein (0.5 mg) doses of IMMU-132 having DARs of 6.89, 3.28, or 1.64. Animals treated with the ADCs having a DAR of 6.89 had a significantly improved median survival time (MST) compared to mice given ADCs with either 3.38 or 1.64 DARs (MST=39 days vs. 25 and 21 days, respectively; P<0.0014) (not shown). There was no difference between groups treated with the 3.28 or 1.64 DAR conjugates and the saline control group.

To further elucidate the importance of a higher DAR, mice bearing NCI-N87 gastric tumors were administered 0.5 mg IMMU-132 with a DAR of 6.89 twice weekly for two weeks (not shown). Another group received twice the protein (1 mg) dose of an IMMU-132 conjugate with a DAR of 3.28. Although both groups received the same total amount of SN-38 (36 μg) with each dosing scheme, those treated with the 6.89 DAR conjugate inhibited tumor growth significantly more than tumor-bearing animals treated with the 3.28 DAR conjugate (P=0.0227; AUC) (not shown). Additionally, treatment with the lower DAR was not significantly different than the untreated controls. Collectively, these studies indicate that a lower DAR reduces efficacy.

An examination of the pharmacokinetic behavior of conjugates prepared at these different ratios was performed in non-tumor-bearing mice given 0.2 mg of each conjugate, unconjugated hRS7 IgG, or hRS7 IgG that was reduced and then capped with N-ethylmaleimide. Serum was taken at 5 intervals from 0.5 to 168 h and assayed by ELISA for hRS7 IgG. There was no significant difference in the clearance of these conjugates compared to the unconjugated IgG (not shown). Thus, the substitution level did not affect the pharmacokinetics of the conjugates, and equally important, the reduction of the interchain disulfide bonds did not appear to destabilize the antibody.

Mechanism of action of IMMU-132 in TNBC. The apoptotic pathway utilized by IMMU-132 was examined in the TNBC cell line, MDA-MB-468, and in the HER2$^+$ SK-BR-3 cell line, in order to confirm that the ADC functions on the basis of its incorporated SN-38. Cells were exposed to 1 μM SN-38, the SN-38-equivalent of IMMU-132, or protein equivalent of hRS7. Cells were harvested and Western blots were performed. SN-38 alone and IMMU-132 mediated >2-fold up-regulation of $p21^{WAF1/Cip1}$ within 24 h in MDA-MB-468, and by 48 h, the amount of $p21^{WAF1/Cip1}$ in these cells began to decrease (31% and 43% with SN-38 or IMMU-132, respectively) (not shown). Interestingly, in the HER2$^+$ SK-BR-3 tumor line, neither SN-38 nor IMMU-132 mediated the up-regulation of $p21^{WAF1/Cip1}$ above constitutive levels in the first 24 h, but as seen in MDA-MB-468 cells after 48-h exposure to SN-38 or IMMU-132, the amount of $p21^{WAF1/Cip1}$ decreased >57% (not shown). Both SN-38 and IMMU-132 resulted in cleavage of pro-caspase-3 into its active fragments within 24 h, but with the greater degree of active fragments observed after exposure for 48 h. Of note, in both cell lines, IMMU-132 mediated a greater degree of pro-caspase-3 cleavage, with the highest level observed after 48 h when compared to cells exposed to SN-38 (not shown). Finally, SN-38 and IMMU-132 both mediated poly ADP ribose polymerase (PARP) cleavage, starting at 24 h, with near complete cleavage after 48 h (not shown). Taken together, these results confirm that IMMU-132 has a mechanism of action similar to that of free SN-38 when administered in vitro.

Delivery of SN-38 by IMMU-132 vs. irinotecan in a human tumor xenograft model. Constitutive products derived from irinotecan or IMMU-132 were determined in the serum and tumors of mice implanted s.c. with a human pancreatic cancer xenograft (Capan-1) administered irinotecan (773 μg; SN-38 equivalents=448 μg) and IMMU-132 (1.0 mg; SN-38 equivalents=16 μg). Following administration, at 5 intervals 3 animals from each group were euthanized with serum extracted for the products of interest.

Irinotecan cleared very rapidly from serum, with conversion to SN-38 and SN-38G seen within 5 min (not shown). None of the products was detected at 24 h. The AUCs over a 6-h period were 21.0, 2.5, and 2.8 μg/mL·h for irinotecan, SN-38, and SN-38G, respectively (SN-38 conversion in mice=[2.5+2.8)/21=25.2%]). Animals given IMMU-132 had much lower concentrations of free SN-38 in the serum, but it was detected through 48 h (not shown). Free SN-38G was detected only at 1 and 6 h, and was 3- to 7-times lower than free SN-38 (not shown).

In the Capan-1 tumors excised from irinotecan-treated animals, irinotecan levels were high over 6 h, but undetectable a 24 h ($AUC_{5\ min-6\ h}$=48.4 μg/g·h). SN-38 was much lower and detected only through 2 h (i.e., $AUC_{5\ min-2\ h}$=0.4 μg/g·h), with SN-38G values almost 3-fold higher (AUC=1.1 μg/g·h) (not shown). Tumors taken from animals given IMMU-132 did not have any detectable free SN-38 or SN-38G, but instead, all SN-38 in the tumor was bound to IMMU-132. Importantly, since no SN-38G was detected in the tumors, this suggests SN-38 bound to IMMU-132 was not glucuronidated. The AUC for SN-38 bound to IMMU-132 in these tumors was 54.3 μg/g·h, which is 135-fold higher than the amount of SN-38 in the tumors of animals treated with irinotecan over the 2-h period that SN-38 could be detected, even though mice given irinotecan received 28-fold more SN-38 equivalents than administered with IMMU-132 (i.e., 448 vs 16 μg SN-38 equivalents, respectively)

Conclusions

IMMU-132 is a humanized anti-Trop-2 antibody conjugated with 7.6 molecules of SN-38, the active metabolite of irinotecan, a topoisomerase I inhibitor. Clinically, IMMU-132 has shown manageable toxicity and encouraging responses in patients with relapsed/refractory TNBC (ClinicalTrials.gov, NCT01631552). IMMU-132 therapy alone demonstrated significant anti-tumor effects in human TNBC xenografts at a human equivalent dose that is 5-fold less than that being used clinically (i.e., 10 mg/kg). Since preclinical studies indicate IMMU-132 can be combined with two different microtubule-inhibitors or a PARP-inhibitor with significantly enhanced anti-tumor activity, these data support the use of IMMU-132 and other antibody-drug conjugates (ADCs) that cause DNA breaks, in combination with microtubule inhibitors and/or PARP inhibitors in general, as well as other chemotherapeutic agents that target cell division through microtubule inhibition or DNA-repair mechanisms. A preferred ADC class is represented by anti-Trop-2 antibody conjugates in patients with Trop-2 positive cancers, including but not limited to TNBC, metastatic colon cancer, SCLC, NSCLC and urothelial cancer, since this is a target that is expressed in high amounts in a large number of cancers, and is localized on the cell surface and cytoplasmically in the cancer cells.

Synergy was achieved when IMMU-132 was combined with PARP-inhibitors (e.g., olaparib) in TNBC tumor lines that had BRCA1/2 defects, as well as wild-type expression, including one with only a PTEN defect. This suggests that IMMU-132 may synergize with any tumor that has any kind of disruption in DNA homologous recombination pathways. Combined with olaparib, IMMU-132 therapy achieved significant anti-tumor effects above that observed with monotherapy with each, resulting in a significant survival benefit. IMMU-132 combined with microtubule inhibitors, (e.g., paclitaxel or eribulin mesylate) also enhanced efficacy significantly compared to monotherapy with each agent.

Overall, these data evidence the unexpected significant advantage of combination therapy with an antibody-drug conjugate (ADC) that targets cancer cells and induces DNA strand breaks, such as IMMU-132, and microtubule inhibitors or PARP inhibitors. Targeting the PARP DNA repair pathway in BRCA1/2 mutant TNBC tumors by combining IMMU-132 therapy with either paclitaxel or olaparib achieved synthetic lethality in this disease model with no observable toxicity. In an exemplary embodiment, the combination of IMMU-132 and a PARP or microtubule inhibitor is of use to treat Trop-2 positive cancers, such as urothelial cancer. These data provide the rationale for use of IMMU-132 in combination with other chemotherapeutics that likewise target DNA-repair mechanisms in patients with urothelial or similar tumors.

From the foregoing description, one skilled in the art can easily ascertain the essential characteristics of this invention, and without departing from the spirit and scope thereof, can make various changes and modifications of the invention to adapt it to various usage and conditions without undue experimentation. All patents, patent applications and publications cited herein are incorporated by reference.

We claim:

1. A method of treating urothelial cancer comprising administering to a human patient with urothelial cancer an antibody-drug conjugate (ADC) sacituzumab govitecan, wherein the ADC is administered at a dosage of between 6 mg/kg and 12 mg/kg.

2. The method of claim 1, wherein the patient has failed to respond to at least one other therapy, prior to treatment with the ADC.

3. The method of claim 1, wherein the dosage is selected from the group consisting of 6 mg/kg, 8 mg/kg, 9 mg/kg, 10 mg/kg, and 12 mg/kg.

4. The method of claim 1, wherein the treatment results in a reduction in tumor size of at least 15%, at least 20%, at least 30%, or at least 40%.

5. The method of claim 1, wherein the cancer is metastatic.

6. The method of claim 5, further comprising reducing in size or eliminating the metastases.

7. The method of claim 1, wherein the cancer is refractory to other therapies but responds to the ADC.

8. The method of claim 1, wherein the patient has failed to respond to therapy with a camptothecin, prior to treatment with the ADC.

9. The method of claim 8, wherein the camptothecin is selected from the group consisting of irinotecan, topotecan and SN-38.

10. The method of claim 1, wherein the ADC dosage is administered to the human patient once or twice a week on a schedule with a cycle selected from the group consisting of: (i) weekly; (ii) every other week; (iii) one week of therapy followed by two, three or four weeks off; (iv) two weeks of therapy followed by one, two, three or four weeks off; (v) three weeks of therapy followed by one, two, three, four or five weeks off; (vi) four weeks of therapy followed by one, two, three, four or five weeks off; (vii) five weeks of therapy followed by one, two, three, four or five weeks off; and (viii) monthly.

11. The method of claim 10, wherein the cycle is repeated 4, 6, 8, 10, 12, 16 or 20 times.

12. The method of claim 1, wherein the ADC is administered in combination with one or more therapeutic agents selected from the group consisting of an antibody, an antigen-binding antibody fragment, a drug, a toxin, an enzyme, a hormone, an immunomodulators, an antisense oligonucleotide, a photoactive agent, a radioisotope a PARP inhibitor, a microtubule inhibitor, a Bruton kinase inhibitor and a PI3K inhibitor.

13. The method of claim 12, wherein the drug or toxin is selected from the group consisting of 5-fluorouracil, afatinib, aplidin, azaribine, anastrozole, anthracyclines, axitinib, AVL-101, AVL-291, bendamustine, bleomycin, bortezomib, bosutinib, bryostatin-1, busulfan, calicheamycin, camptothecin, carboplatin, 10-hydroxycamptothecin, carmustine, celecoxib, chlorambucil, cisplatin (CDDP), Cox-2 inhibitors, irinotecan (CPT-11), SN-38, carboplatin, cladribine, camptothecans, cyclophosphamide, crizotinib, cytarabine, dacarbazine, dasatinib, dinaciclib, docetaxel, dactinomycin, daunorubicin, doxorubicin, 2-pyrrolinodoxorubicine (2P-DOX), cyano-morpholino doxorubicin, doxorubicin glucuronide, epirubicin glucuronide, erlotinib, estramustine, epipodophyllotoxin, erlotinib, entinostat, estrogen receptor binding agents, etoposide (VP16), etoposide glucuronide, etoposide phosphate, exemestane, fingolimod, flavopiridol, floxuridine (FUdR), 3',5'-O-dioleoyl-FudR (FUdR-dO), fludarabine, flutamide, farnesyl-protein transferase inhibitors, fostamatinib, ganetespib, GDC-0834, GS-1101, gefitinib, gemcitabine, hydroxyurea, ibrutinib, idarubicin, idelalisib, ifosfamide, imatinib, L-asparaginase, lapatinib, lenolidamide, leucovorin, LFM-A13, lomustine, mechlorethamine, melphalan, mercaptopurine, 6-mercaptopurine, methotrexate, mitoxantrone, mithramycin, mitomycin, mitotane, navelbine, neratinib, nilotinib, nitrosurea, olaparib, plicomycin, procarbazine, paclitaxel, PCI-32765, pentostatin, PSI-341, raloxifene, semustine, sorafenib, streptozocin, SU11248, sunitinib, tamoxifen, temazolomide, transplatinum, thalidomide, thioguanine, thiotepa, teniposide, topotecan, uracil mustard, vatalanib, vinorelbine, vinblastine, vincristine, vinca alkaloids and ZD1839.

14. The method of claim 12, wherein the PARP inhibitor is selected from the group consisting of olaparib, talazoparib (BMN-673), rucaparib, veliparib, CEP 9722, MK 4827, BGB-290, ABT-888, AG014699, BSI-201, CEP-8983 and 3-aminobenzamide.

15. The method of claim 12, wherein the PARP inhibitor is olaparib.

16. The method of claim 12, wherein the microtubule inhibitor is selected from the group consisting of a vinca alkaloid, a taxane, a maytansinoid, an auristatin, vincristine, vinblastine, paclitaxel, mertansine, demecolcine, nocodazole, epothilone, docetaxel, disodermolide, colchicine, combrestatin, podophyllotoxin, CI-980, phenylahistins, steganacins, curacins, 2-methoxy estradiol, E7010, methoxy benzenesuflonamides, vinorelbine, vinflunine, vindesine, dolastatins, spongistatin, rhizoxin, tasidotin, halichondrins, hemiasterlins, cryptophycin 52, MMAE and eribulin mesylate.

17. The method of claim 12, wherein the microtubule inhibitor is paclitaxel or eribulin mesylate.

18. The method of claim 12, wherein the Bruton kinase inhibitor is selected from the group consisting of ibrutinib (PCI-32765), PCI-45292, CC-292 (AVL-292), ONO-4059, GDC-0834, LFM-A13 and RN486.

19. The method of claim 12, wherein the Bruton kinase inhibitor is ibrutinib.

20. The method of claim 12, wherein the PI3K inhibitor is selected from the group consisting of idelalisib, Wortmannin, demethoxyviridin, perifosine, PX-866, IPI-145(duvelisib), BAY 80-6946, BEZ235, RP6530, TGR1202, SF1126, INK1117, GDC-0941, BKM120, XL147, XL765, Palomid 529, GSK1059615, ZSTK474, PWT33597, IC87114, TG100-115, CAL263, PI-103, GNE477, CUDC-907, AEZS-136 and LY294002.

21. The method of claim 12, wherein the PI3K inhibitor is idelalisib.

* * * * *

SEQUENCE LISTING

```
<160> NUMBER OF SEQ ID NOS: 9

<210> SEQ ID NO 1
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Lys Ala Ser Gln Asp Val Ser Ile Ala Val Ala
1               5                   10

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ser Ala Ser Tyr Arg Tyr Thr
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gln Gln His Tyr Ile Thr Pro Leu Thr
1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
```

```
                               peptide

<400> SEQUENCE: 4

Asn Tyr Gly Met Asn
1               5

<210> SEQ ID NO 5
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Trp Ile Asn Thr Tyr Thr Gly Glu Pro Thr Tyr Thr Asp Asp Phe Lys
1               5                   10                  15

Gly

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Gly Phe Gly Ser Ser Tyr Trp Tyr Phe Asp Val
1               5                   10

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ala Leu Ala Leu
1

<210> SEQ ID NO 8
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95
```

Lys Ala Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 9
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro

```
              115                 120                 125
Lys Pro Lys Asp Thr Leu Met Ile Ser Arg Thr Pro Glu Val Thr Cys
    130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Glu Glu
225                 230                 235                 240
Met Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330
```